US011318266B2

(12) United States Patent
Holley et al.

(10) Patent No.: US 11,318,266 B2
(45) Date of Patent: May 3, 2022

(54) METHODS AND APPARATUS FOR RESPIRATORY TREATMENT

(71) Applicant: ResMed Pty Ltd, Bella Vista (AU)

(72) Inventors: Liam Holley, Marrickville (AU); Gordon Joseph Malouf, Sydney (AU); Dion Charles Chewe Martin, Sydney (AU); Peter Wlodarczyk, Ashfield (AU); Quangang Yang, Kellyville (AU)

(73) Assignee: ResMed Pty Ltd ( * ) Notice: Subject to any disclaimer, the term of this patent is extended or adjusted under 35 U.S.C. 154(b) by 815 days.

(21) Appl. No.: 15/781,599

(22) PCT Filed: Dec. 9, 2016

(86) PCT No.: PCT/AU2016/051210
§ 371 (c)(1),
(2) Date: Jun. 5, 2018

(87) PCT Pub. No.: WO2017/096428
PCT Pub. Date: Jun. 15, 2017

(65) Prior Publication Data
US 2019/0111226 A1 Apr. 18, 2019

Related U.S. Application Data

(60) Provisional application No. 62/265,700, filed on Dec. 10, 2015.

(51) Int. Cl.
A61M 16/06 (2006.01)
A61M 16/16 (2006.01)
(Continued)

(52) U.S. Cl.
CPC ...... A61M 16/0666 (2013.01); A61M 16/024 (2017.08); A61M 16/0683 (2013.01);
(Continued)

(58) Field of Classification Search
CPC ...... A61M 16/022–26; A61M 16/0057; A61M 16/0666; A61M 16/0672; A61M 16/0069;
(Continued)

(56) References Cited

U.S. PATENT DOCUMENTS 4,944,310 A 7/1990 Sullivan
5,694,923 A 12/1997 Hete et al.
(Continued)

FOREIGN PATENT DOCUMENTS

CA 2926772 A1 4/2015
JP 2007531540 A 11/2007
(Continued)

OTHER PUBLICATIONS

International Search Report for Application No. PCT/AU2016/051210 dated May 18, 2017.
(Continued)

Primary Examiner — Margaret M Luarca
Assistant Examiner — Cana A Gallegos
(74) Attorney, Agent, or Firm — Botos Churchill IP Law LLP

(57) ABSTRACT

Apparatus and methods provide control for generation of a flow of air to a patient's airways for different respiratory therapies. The pressure and a flow rate may be simultaneously controlled so as to provide a pressure therapy and a flow therapy. The system may include one or more flow generators, in which the control of the pressure and flow rate may include altering the output of one or more of the flow generators and/or an optional adjustable vent. The pressure and flow rate may each be held at a constant. One or both of the pressure and flow rate may also vary in accordance with a desired therapy. The air may be provided via a patient interface that includes a vent to atmosphere, which may be the adjustable vent. The vent may be actuated by a controller
(Continued)

to implement the simultaneous control of pressure and flow rate of the air.

37 Claims, 36 Drawing Sheets

(51) Int. Cl.
*A61M 16/00* (2006.01)
*A61M 16/12* (2006.01)
*A61M 16/20* (2006.01)

(52) U.S. Cl.
CPC ......... *A61M 16/16* (2013.01); *A61M 16/0069* (2014.02); *A61M 16/0605* (2014.02); *A61M 16/12* (2013.01); *A61M 16/205* (2014.02); *A61M 2016/0027* (2013.01); *A61M 2016/0036* (2013.01); *A61M 2202/0208* (2013.01); *A61M 2202/0225* (2013.01); *A61M 2205/15* (2013.01); *A61M 2205/3365* (2013.01); *A61M 2205/3584* (2013.01); *A61M 2205/42* (2013.01); *A61M 2205/502* (2013.01); *A61M 2210/0618* (2013.01); *A61M 2210/0625* (2013.01)

(58) Field of Classification Search
CPC .... A61M 2016/0027; A61M 2016/003; A61M 2016/0036; A61M 2205/15; A61M 2205/3331–3344; A61M 2205/3365
See application file for complete search history.

(56) References Cited

U.S. PATENT DOCUMENTS

| | | | |
|---|---|---|---|
| 6,532,959 B1 | 3/2003 | Berthon-Jones | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,752,551 B2 | 6/2014 | Chandran et al. | |
| 2005/0011523 A1* | 1/2005 | Aylsworth | A61M 16/0069 128/207.18 |
| 2007/0062531 A1* | 3/2007 | Fisher | A61M 16/206 128/204.23 |
| 2007/0113856 A1* | 5/2007 | Acker | A61M 16/0666 128/207.14 |
| 2007/0163590 A1* | 7/2007 | Bassin | A61M 16/0069 128/204.23 |
| 2007/0173728 A1* | 7/2007 | Pu | A61B 5/02405 600/484 |
| 2008/0302364 A1 | 12/2008 | Garde | |
| 2009/0241960 A1 | 10/2009 | Tunnell et al. | |
| 2011/0155133 A1 | 6/2011 | Barnes et al. | |
| 2011/0253136 A1 | 10/2011 | Sweeney et al. | |
| 2012/0065533 A1 | 3/2012 | Carrillo et al. | |
| 2012/0304993 A1 | 12/2012 | Nitta et al. | |
| 2012/0305001 A1* | 12/2012 | Tatkov | A61M 16/1095 128/205.25 |
| 2013/0102917 A1 | 4/2013 | Colbaugh et al. | |
| 2014/0069428 A1 | 3/2014 | Sears et al. | |
| 2014/0144438 A1* | 5/2014 | Klasek | A61B 5/0205 128/203.14 |
| 2014/0261415 A1 | 9/2014 | Acker et al. | |
| 2015/0120067 A1 | 4/2015 | Wing et al. | |

FOREIGN PATENT DOCUMENTS

| | | | |
|---|---|---|---|
| WO | 9908738 A1 | 2/1999 | |
| WO | 2005009501 A2 | 2/2005 | |
| WO | WO-2010141983 A1 * | 12/2010 | ........ A61M 16/0006 |
| WO | 2011006199 A1 | 1/2011 | |
| WO | WO-2012012835 A2 * | 2/2012 | ........ A61M 16/0069 |
| WO | 2012032434 A1 | 3/2012 | |
| WO | 2013020167 A1 | 2/2013 | |
| WO | 2013163685 A1 | 11/2013 | |
| WO | 2013040198 A3 | 5/2014 | |
| WO | 2014138803 A1 | 9/2014 | |
| WO | 2014138820 A1 | 9/2014 | |
| WO | 2015145390 A1 | 10/2015 | |
| WO | 2015192186 A1 | 12/2015 | |

OTHER PUBLICATIONS

Japanese Office Action, dated Nov. 17, 2020 for Japanese Patent Application No. 2018-530102.
Extended EP Search Report for EP Application No. 16871824.5 dated Jul. 16, 2019.
EP Search Report dated Aug. 17, 2021 for EP Application No. 21157408.2.

* cited by examiner

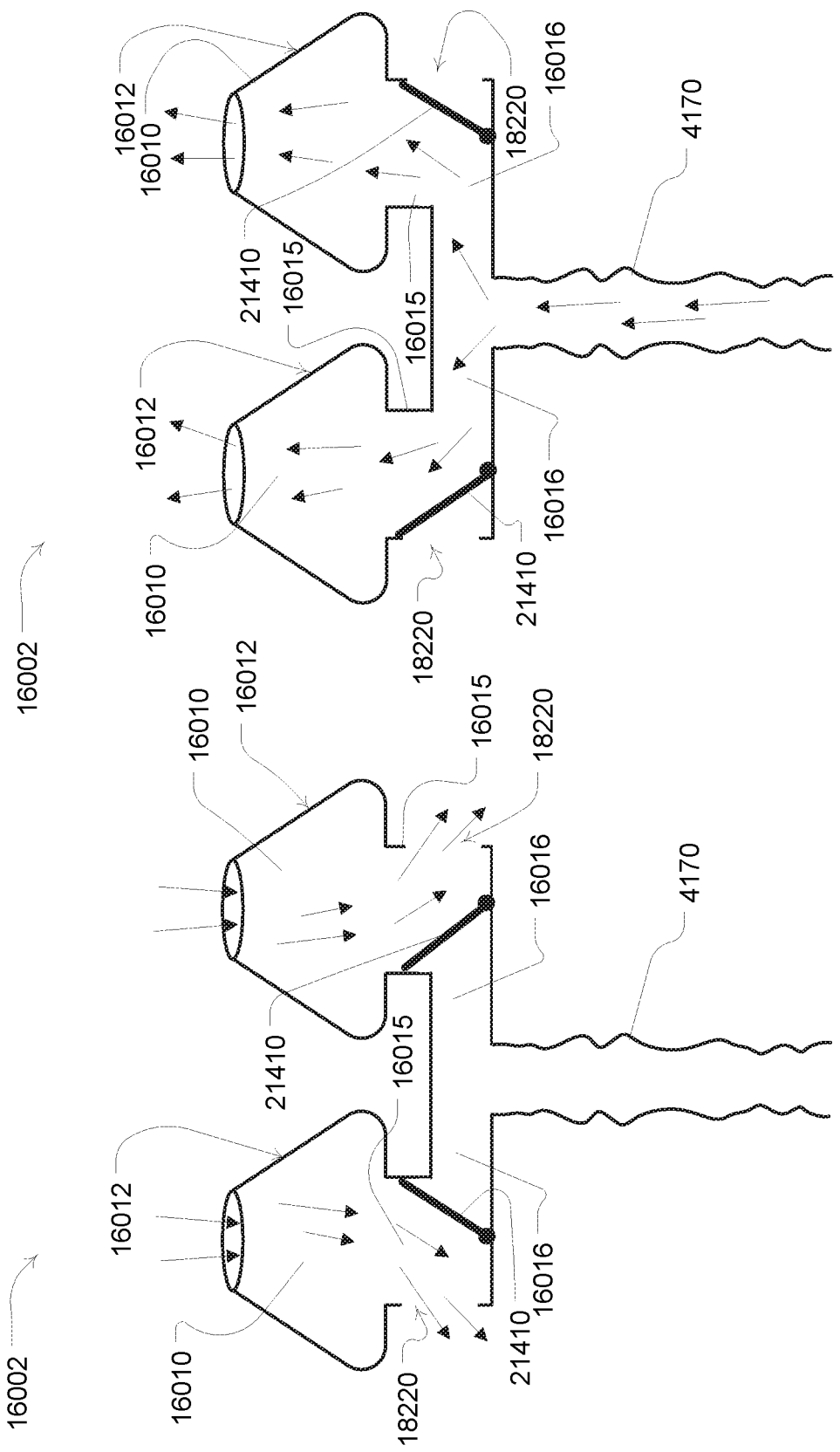

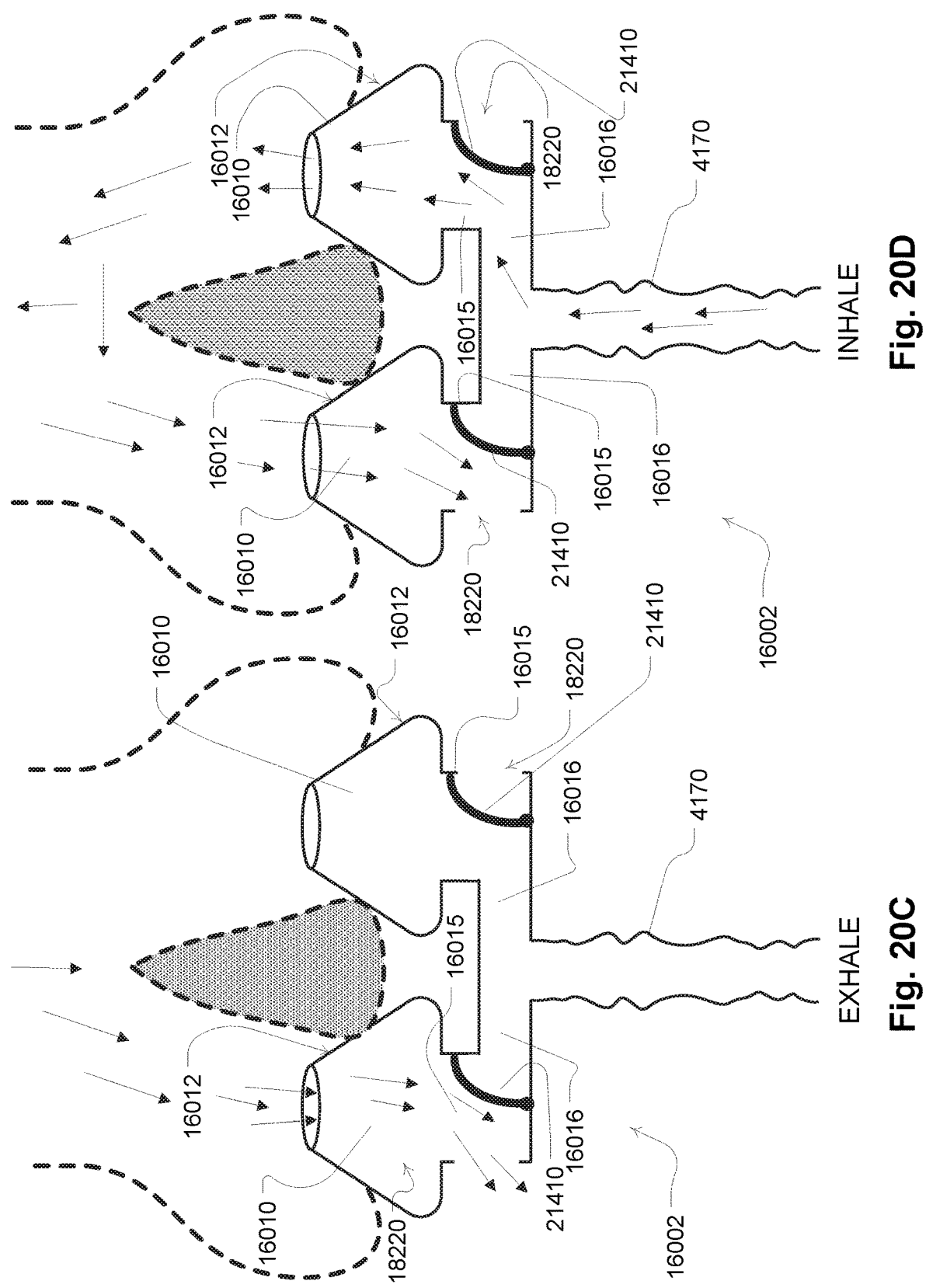

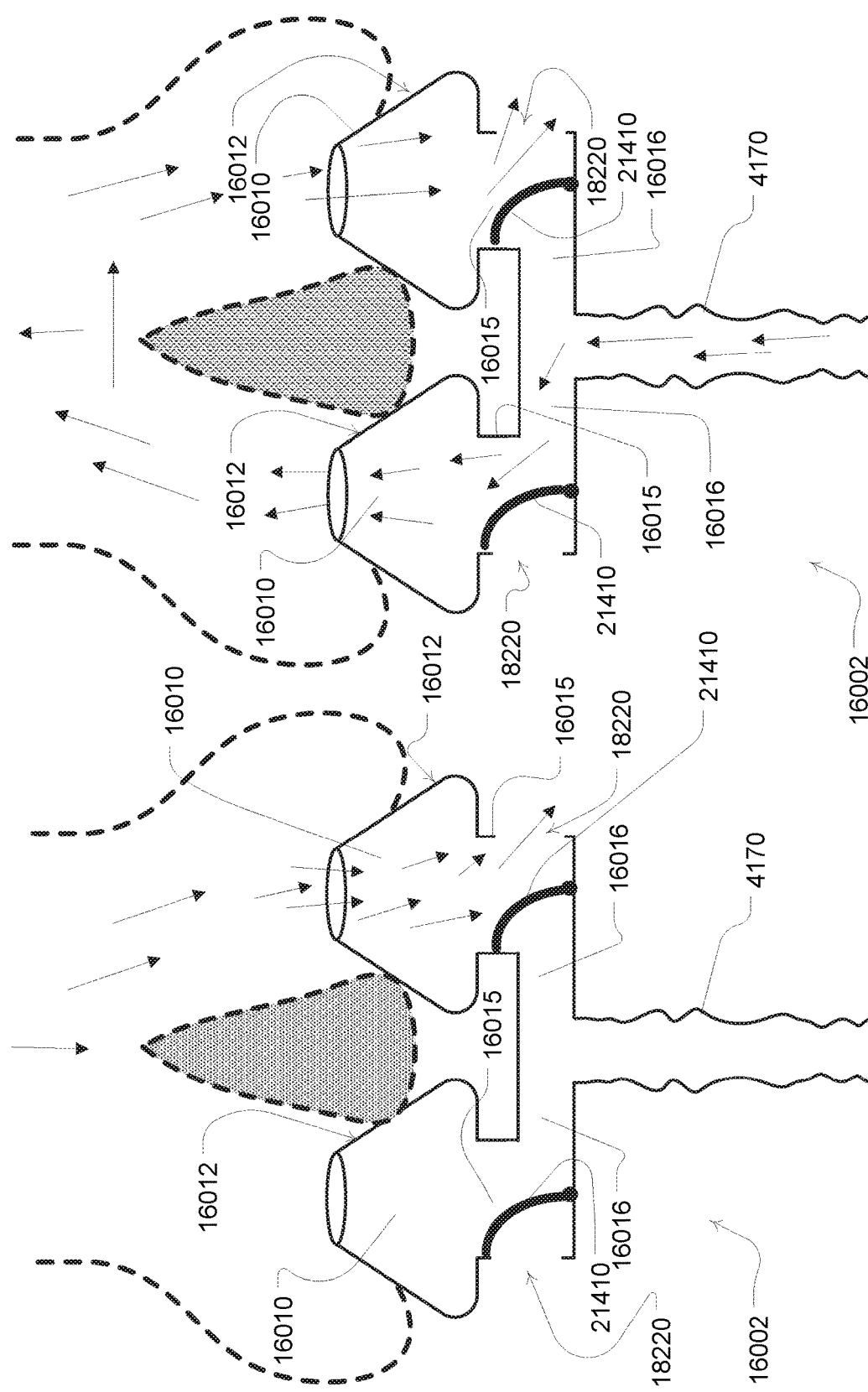

METHODS AND APPARATUS FOR RESPIRATORY TREATMENT

1 CROSS-REFERENCE TO RELATED APPLICATIONS

The present application is a national phase entry under 35 U.S.C. § 371 of International Application No. PCT/AU2016/051210 filed Dec. 9, 2016, published in English, which claims priority from U.S. Provisional Application No. 62/265,700, filed Dec. 10, 2015, all of which are incorporated herein by reference.

2 STATEMENT REGARDING FEDERALLY SPONSORED RESEARCH OR DEVELOPMENT

Not Applicable

3 SEQUENCE LISTING

Not Applicable

4 BACKGROUND OF THE INVENTION

4.1 Field of the Invention

The present technology relates to one or more of the detection, diagnosis, treatment, prevention and amelioration of respiratory-related disorders. In particular, the present technology relates to medical devices or apparatus, and their use and may include devices for directing treatment gas to a patient's respiratory system.

4.2 Description of the Related Art

4.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

4.2.2 Therapies

Nasal Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion by pushing the soft palate and tongue forward and away from the posterior oropharyngeal wall.

Non-invasive ventilation (NIV) provides ventilatory support (pressure support) to a patient through the upper airways to assist the patient in taking a full breath and/or maintain adequate oxygen levels in the body by doing some or all of the work of breathing (e.g., mechanical work of breathing). The ventilatory support is provided via a patient interface. NIV has been used to treat CSR, OHS, COPD, MD and Chest Wall disorders.

Invasive ventilation (IV) provides ventilatory support to patients that are no longer able to effectively breathe themselves and may be provided using a tracheostomy tube.

High Flow therapy (HFT) is the provision of a continuous, heated, humidified flow of air to an entrance to the airway through an unsealed or open interface at flow rates similar to, or greater than peak inspiratory flow. HFT has been used to treat OSA, CSR, COPD and other respiratory disorders. One mechanism of action is that the high flow rate of air at the airway entrance improves ventilation efficiency by flushing, or washing out, expired $CO_2$ from the patient's anatomical deadspace. HFT is thus sometimes referred to as a deadspace therapy (DST).

Another form of flow therapy is supplemental oxygen therapy, whereby air with an elevated percentage of oxygen is supplied to an entrance to the airway through an unsealed interface.

4.2.3 Systems

One known device used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

A treatment system may comprise a Positive Airway Pressure (PAP) device/ventilator, an air circuit, a humidifier, a patient interface, and data management.

4.2.4 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 $cmH_2O$. For other forms of therapy, such as HFT, the patient interface may not include a seal sufficient to facilitate delivery to the airways of a supply of gas at a positive pressure of about 10 cmH2O.

4.2.5 Respiratory Apparatus (PAP Device/Ventilator)

Examples of respiratory apparatuses include ResMed's S9 AutoSet™ PAP device and ResMed's Stellar™ 150 ventilator. Respiratory apparatuses typically comprise a pressure generator, such as a motor-driven blower or a compressed gas reservoir, and are configured to supply a flow of air to the airway of a patient, typically via a patient interface such as those described above. In some cases, the flow of air may be supplied to the airway of the patient at positive pressure. The outlet of the respiratory apparatus is connected via an air circuit to a patient interface such as those described above.

4.2.6 Humidifier

Delivery of a flow of air without humidification may cause drying of airways. Medical humidifiers are used to increase humidity and/or temperature of the flow of air in relation to ambient air when required, typically where the patient may be asleep or resting (e.g. at a hospital). As a result, a medical humidifier is preferably small for bedside placement, and it is preferably configured to only humidify and/or heat the flow of air delivered to the patient without humidifying and/or heating the patient's surroundings.

5 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

Another aspect of the present technology relates to the provision of a dead space therapy comprising a controlled generation a flow of air towards a patient's respiratory cavity for flushing expired gas ($CO_2$) from the patient's anatomical deadspace.

Another aspect of the present technology relates to the provision of a pressure therapy comprising a controlled generation of pressurized air at a patient's respiratory system, (e.g., pressure support therapy to mechanically assist with patient respiration).

Another aspect of the present technology relates to methods of providing such a pressure therapy and such a dead space therapy simultaneously.

Another aspect of the present technology relates to apparatus configured for provision of such a pressure therapy and such a dead space therapy simultaneously or alternatively.

Some versions of the present technology may include a method for controlling a supply of air to a patient's airways for a respiratory therapy. The method may include identifying, by one or more controllers, a predetermined pressure and a predetermined flow rate of the air to be provided to a patient via a patient interface. The method may include determining, with a plurality of sensors, a pressure and a flow rate of the air being provided to the patient via the patient interface. The method may include controlling, by the one or more controllers, a first flow generator and a second flow generator, each flow generator being configured to provide a flow of the air to the patient interface, so as to simultaneously control the pressure and the flow rate of the air at the patient interface to correspond with the predetermined pressure and the predetermined flow rate, respectively.

In some method versions, the controlling the first flow generator and the second flow generator may include adjusting output of at least one of the first flow generator and the second flow generator. The patient interface may include a projection portion configured to conduct a flow of the air into a naris of the patient and a mask portion configured to apply pressure of the air to the patient. The mask portion may be a nasal mask. The mask portion may include nasal pillows. The method may include detecting a continuous mouth leak, and reducing the predetermined pressure upon detecting the continuous mouth leak. The first flow generator may provide the flow of the air through the projection portion of the patient interface and the second flow generator may apply pressure of the air to the mask portion of the patient interface. At least one, or both, of the predetermined pressure and the predetermined flow rate may vary over a period of time corresponding to a breathing cycle of the patient. The predetermined flow rate may be constant for at least some predetermined period of time and/or the predetermined pressure may be constant during the predetermined period of time. The mask portion of the patient interface further may include a vent.

In some versions, the method may include limiting the predetermined flow rate to be less than a maximum flow rate. The maximum flow rate may be a vent flow rate minus a peak expiratory flow rate of the patient. The simultaneously controlling of the pressure and the flow rate may further include controlling an adjustment of the vent. The vent may include an active proximal valve. The simultaneously controlling of the pressure and the flow rate may be performed so as to provide the patient with a positive airway pressure therapy and a deadspace therapy. The positive airway pressure therapy may be a ventilation therapy. The method may include determining, by the one or more controllers, the predetermined pressure and the predetermined flow rate so as restrict the predetermined pressure and the predetermined flow rate to a curve of equal efficacy. The method may include calculating, in a controller of the one or more controllers, a target ventilation based on anatomical deadspace information and a deadspace therapy reduction value. The method may include generating, in a controller of the one or more controllers, a cardiac output estimate by controlling a step change in the predetermined flow rate of the air and determining a change in a measure of ventilation in relation to the step change. The method may include initiating, by the controller of the one or more controllers, the controlling of the step change in the predetermined flow rate of the air in response to a detection of sleep.

Some versions of the present technology may include a system for delivery of a flow of air to a patient's airways. The system may include a first flow generator and a second flow generator, each configured to provide air to a patient via a patient interface. The system may include one or more controllers. The one or more controllers may be configured to determine a pressure and a flow rate of the air being provided to the patient via the patient interface with a plurality of sensors. The one or more controllers may be configured to control the first flow generator and the second flow generator so as to simultaneously control the pressure and the flow rate of the air at the patient interface to correspond with a predetermined pressure and a predetermined flow rate, respectively.

In some versions, the system may include the patient interface, wherein the patient interface may include a projection portion configured to conduct a flow of the air into a naris of the patient and a mask portion configured to apply pressure of the air to the patient. The mask portion may be a nasal mask. The mask portion may be nasal pillows. The first flow generator may conduct the flow of the air through the projection portion and the second flow generator may apply pressure of the air to the mask portion. The plurality of sensors may include a flow rate sensor and a pressure sensor. An output of the first flow generator may be measured by the flow rate sensor and an output of the second flow generator may be measured by the pressure sensor. The one or more controllers may be configured to maintain at least one of the predetermined pressure and the predetermined flow rate at a constant value for at least some period of time. The one or more controllers may be further configured to vary at least one of the predetermined pressure and the predetermined flow rate over a period of time corresponding to a breathing cycle of the patient. The mask portion of the patient interface may include a vent. The one or more controllers may be configured to limit the predetermined flow rate to be less than a maximum flow rate. The one or more controllers may be configured to determine the maximum flow rate by subtracting a peak expiratory flow rate of the patient from a vent flow rate. The vent may be an adjustable vent and the one or more controllers may be configured to control the adjustable vent so as to control the pressure and the flow rate. The adjustable vent may include an active proximal valve. The simultaneous control of the pressure and the flow rate of the air may provide the patient with a positive airway pressure therapy and a deadspace therapy. The positive airway pressure therapy may be a ventilation therapy.

In some versions, the one or more controllers may be configured to determine the predetermined pressure and the predetermined flow rate so as to restrict the predetermined pressure and the predetermined flow rate to a curve of equal efficacy. The one or more controllers may include one controller configured to control the first flow generator and the second flow generator. The one or more controllers may include a first controller configured to control the first flow generator and a second controller configured to control the second flow generator. The first controller may be configured to obtain the flow rate of the air being provided by the second flow generator. The second controller may be configured to obtain the pressure of the air being provided by the first flow generator. In some cases, a controller of the one or more controllers may be configured to compute a target ventilation based on anatomical deadspace information and a deadspace therapy reduction value. A controller of the one or more controllers may be configured to generate a cardiac output estimate by controlling a step change in the predetermined flow rate of the air and determining a change in a measure of ventilation in relation to the step change. The controller of the one or more controllers may be configured to initiate control of the step change in the predetermined flow rate of the air in response to a detection of sleep.

Some versions of the present technology may include a system for delivery of a flow of air to a patient's airways. The system may include a flow generator configured to provide air to a patient via an air circuit and a patient interface. The system may include an adjustable vent. The system may include one or more controllers. The one or more controllers may be configured to determine a pressure and a flow rate of the air being provided to the patient via the patient interface with a plurality of sensors. The one or more controllers may be configured to control the flow generator and the adjustable vent so as to simultaneously control the pressure and the flow rate of the air at the patient interface to correspond with a predetermined pressure and a predetermined flow rate, respectively.

In some versions, the system may include the patient interface. The patient interface may include a projection portion configured to conduct a flow of the air into a naris of a patient and a mask portion configured to apply pressure of the air to the patient. The adjustable vent may be part of the mask portion of the patient interface. The plurality of sensors may include a pressure sensor for determining a measured pressure of the air. The plurality of sensors may include a flow rate sensor for determining a measured flow rate of the air through the projection portion of the patient interface. In some cases, at least one of the pressure sensor and the flow rate sensor may be located at an output of the flow generator. In some cases, at least one of the pressure sensor and the flow rate sensor may be located at the patient interface. The one or more controllers may be configured to maintain at least one, or both, of the predetermined pressure and the predetermined flow rate at a constant value for a period of time. The one or more controllers may be further configured to vary the predetermined pressure in accordance with a breathing cycle of the patient. The simultaneous control of the pressure and the flow rate of the air may provide the patient with a positive airway pressure therapy and a deadspace therapy. The positive airway pressure therapy may be a ventilation therapy. The one or more controllers may be configured to determine the predetermined pressure and the predetermined flow rate to restrict the predetermined pressure and the predetermined flow rate to a curve of equal efficacy.

In some versions, the system may further include a variable resistance in the air circuit, wherein the one or more controllers may be configured to control one or more of the pressure and the flow rate of the air by adjusting the resistance of the variable resistance. In some cases, a controller of the one or more controllers may be configured to compute a target ventilation based on anatomical deadspace information and a deadspace therapy reduction value. A controller of the one or more controllers may be configured to generate a cardiac output estimate by controlling a step change in the predetermined flow rate of the air and determining a change in a measure of ventilation in relation to the step change. The controller of the one or more controllers may be configured to initiate control of the step change in the predetermined flow rate of the air in response to a detection of sleep.

Some versions of the present technology may include a method for controlling a supply of air to a patient's airways for a respiratory therapy. The method may include identifying, by one or more controllers, a predetermined pressure and a predetermined flow rate of the air to be provided to a patient via an air circuit and a patient interface. The method may include determining, with a plurality of sensors, a pressure and a flow rate of the air being provided to the patient via the patient interface. The method may include controlling, by the one or more controllers, a flow generator configured to provide the air to the patient interface, and an adjustable vent so as to simultaneously control the pressure and the flow rate of the air at the patient interface to correspond with the predetermined pressure and the predetermined flow rate, respectively. The patient interface may include a projection portion configured to conduct a flow of the air into a naris of the patient and a mask portion configured to apply pressure of the air to the patient. The flow generator may provide the flow of the air through the projection portion of the patient interface thereby applying pressure of the air to the mask portion of the patient interface. The method may include maintaining, by the one or more controllers, at least one of the predetermined pressure and the predetermined flow rate at a constant value for a period of time. The method may include varying, by the one or more controllers, the predetermined pressure in accordance with a breathing cycle of the patient. The simultaneous control of the pressure and the flow rate of the air may include control of a positive airway pressure therapy and a deadspace therapy. The positive airway pressure therapy may be a ventilation therapy.

In some versions, the method may include determining, by the one or more controllers, the predetermined pressure and the predetermined flow rate so as to restrict the predetermined pressure and the predetermined flow rate to a curve of equal efficacy. The controlling of the adjustable vent comprises adjusting, by the one or more controllers, a venting characteristic of the adjustable vent in synchrony with the patient's breathing cycle so as to maintain the pressure of the air at the patient interface to correspond with the predetermined pressure. The method may include adjusting, by the one or more controllers, a resistance of a variable resistance in the air circuit so as to control one or more of the pressure and the flow rate of the air. The method may include calculating, in the one or more controllers, a target ventilation based on anatomical deadspace information and a deadspace therapy reduction value. The method may include generating, in the one or more controllers, a cardiac output estimate by controlling a step change in the predetermined flow rate of the air and determining a change in a measure of ventilation in relation to the step change. The method may include initiating, by the one or more controllers, the controlling of the step change in the predetermined flow rate of the air in response to a detection of sleep.

In yet another aspect of the present technology, a supply of air to a patient's airways may be controlled in connection with a respiratory therapy. The respiratory therapy may include identifying, by one or more controllers, a predetermined pressure and a predetermined flow rate of air to be provided to a patient via a patient interface; determining, by one or more sensors, a pressure and a flow rate of the air being provided to a patient via a patient interface; and controlling, by the one or more controllers, a first flow generator and a second flow generator, so as to simultaneously control the pressure and the flow rate of the air to correspond with the predetermined pressure and the predetermined flow rate, respectively. Controlling the first flow generator and the second flow generator may include adjusting an output of at least one of the first flow generator and the second flow generator. In addition, the patient interface may include a projection portion configured to conduct a flow of the air into a naris of the patient and a mask portion configured to apply pressure of the air to the patient. The first flow generator may conduct the flow of the air through a projection portion of the patient interface and the second flow generator may apply pressure from the air to a mask portion of the patient interface.

In still another aspect, at least one of the predetermined pressure and the predetermined flow rate may vary over a period of time corresponding to a breathing cycle of the patient. The predetermined flow rate may also be constant for at least some predetermined period of time and the predetermined pressure may be constant during the predetermined period of time.

In another aspect, the patient interface may include a vent, and simultaneously controlling the pressure and the flow rate may include controlling an adjustment of the vent. The vent may include an adjustable proximal valve.

In still another aspect, simultaneously controlling the pressure and the flow rate may be performed so as to provide the patient with a pressure therapy and a deadspace therapy.

In another aspect, a system for delivery of a flow of air to a patient's airways may include a first flow generator and a second flow generator for providing air to a patient respiratory interface and one or more controllers configured to: determine a pressure and a flow rate of the air with a plurality of sensors, and control the first flow generator and the second flow generator so as to simultaneously control the pressure and the flow rate of the air at the patient interface. The patient interface may include a projection portion configured to conduct a flow of the air into a naris of the patient and a mask portion configured to apply pressure of the air to the patient. In addition, the first flow generator may conduct the flow of the air through the projection portion and the second flow generator may apply air pressure to the mask portion. The plurality of sensors may include a flow sensor and a pressure sensor, and an output of the first flow generator may be measured by the flow sensor and an output of the first flow generator may be measured by the pressure sensor. The controllers may be configured to maintain at least one of the pressure and the flow rate at a constant for at least some period of time. The controllers may also be configured so that at least one of the pressure and the flow rate is variable over a period of time. The patient interface may include an adjustable vent and the one or more controllers may be further configured to control the adjustable vent.

In still another aspect, a system for delivery of a flow of air to a patient's airways may include a flow generator for providing air to a patient via a patient interface, an adjustable vent, and one or more controllers. The one or more controllers may be configured to determine a pressure and a flow rate of the air with one or more sensors and control at least one of the flow generator and the adjustable vent so as to simultaneously control and vary the pressure and the flow rate of the air over a breathing cycle of the patient. The patient interface may include a projection portion configured to conduct a flow of the air into a naris of a patient and a mask portion configured to apply pressure of the air to the patient. The adjustable vent may be a part of the mask portion of the patient interface. The system may also include a pressure sensor for determining a measured pressure of the air corresponding to the pressure of the air at the mask portion of the patient interface and a flow sensor for determining a measured flow rate of the air through the projection portion of the patient interface. At least one of the pressure sensor and the flow sensor may be located at an output of the flow generator or at the patient interface. In addition, the controllers may be configured to vary the pressure in accordance with a detected breathing cycle. The flow generator may also include a first flow generator and a second flow generator.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

6 BRIEF DESCRIPTION OF THE DRAWINGS

The present technology is illustrated by way of example, and not by way of limitation, in the figures of the accompanying drawings, in which like reference numerals refer to similar elements including:

6.1 Treatment Systems

FIG. 1A shows a system including a patient 1000 wearing a patient interface 3000, in the form of a nasal pillows, receives a supply of air at positive pressure from a Combination Therapy (CT) device 4000. Air from the CT device is humidified in a humidifier 5000, and passes along an air circuit 4170 to the patient 1000. A bed partner 1100 is also shown.

6.2 Therapy

6.2.1 Respiratory system

Figure 1A:
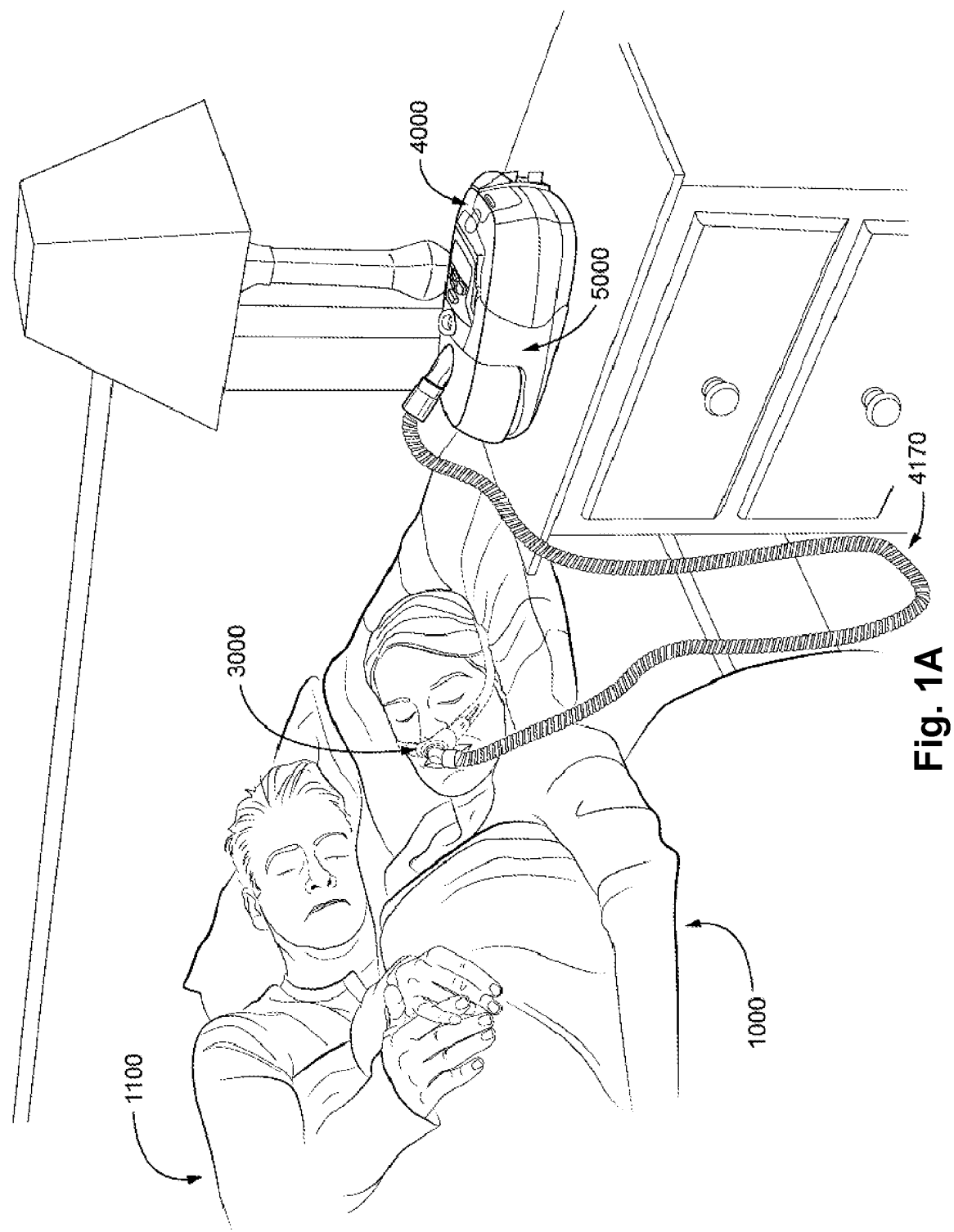
FIG. 1B shows a system including a patient 1000 wearing a patient interface 3000, in the form of a nasal mask, receives a supply of air at positive pressure from a CT device 4000. Air from the CT device is humidified in a humidifier 5000, and passes along an air circuit 4170 to the patient 1000.
FIG. 1C shows a system including a patient 1000 wearing a patient interface 3000, in the form of a full-face mask, receives a supply of air at positive pressure from a CT device 4000. Air from the CT device is humidified in a humidifier 5000, and passes along an air circuit 4170 to the patient 1000.
Figure 1B:
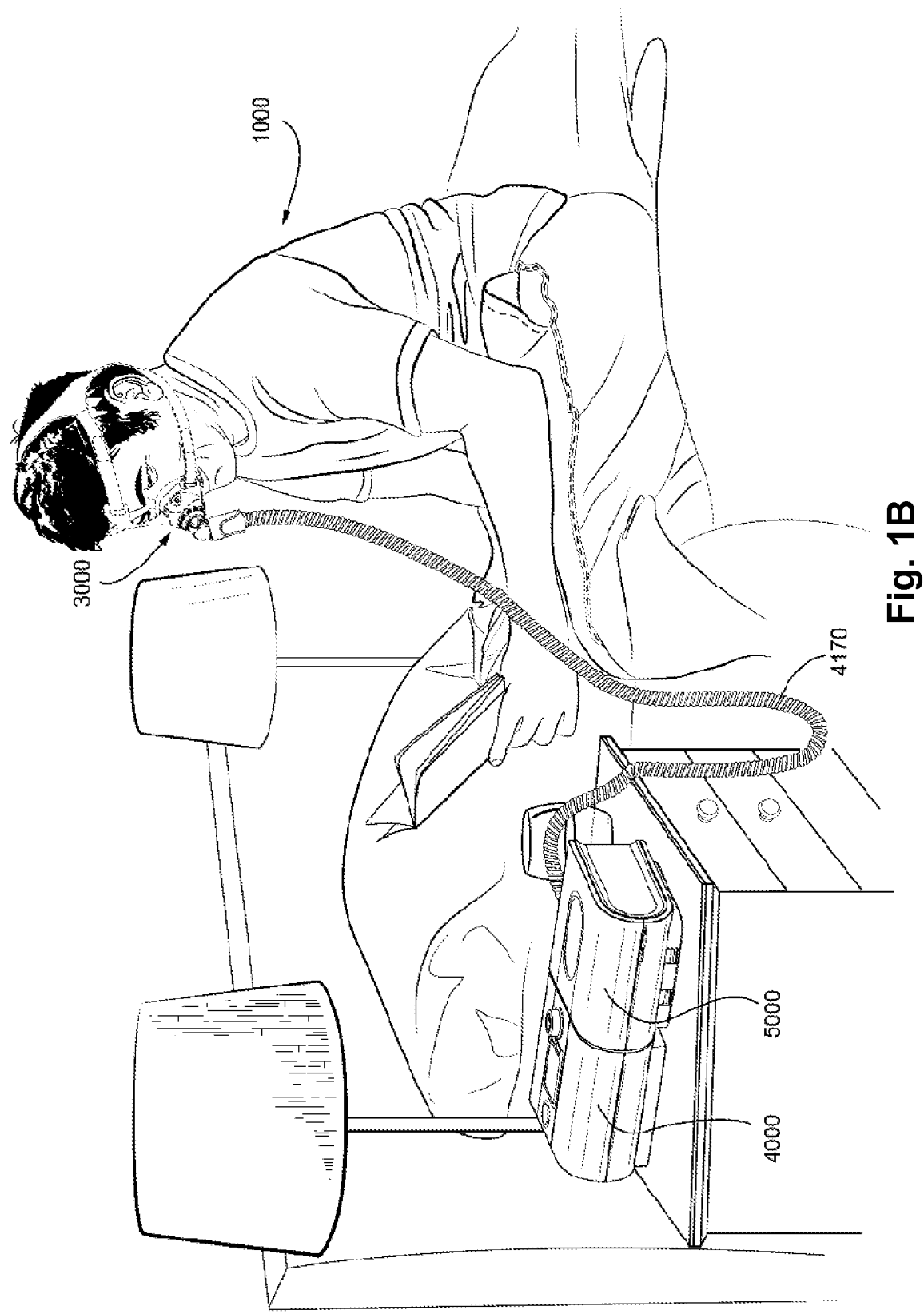
Figure 1C:
Figure 2:
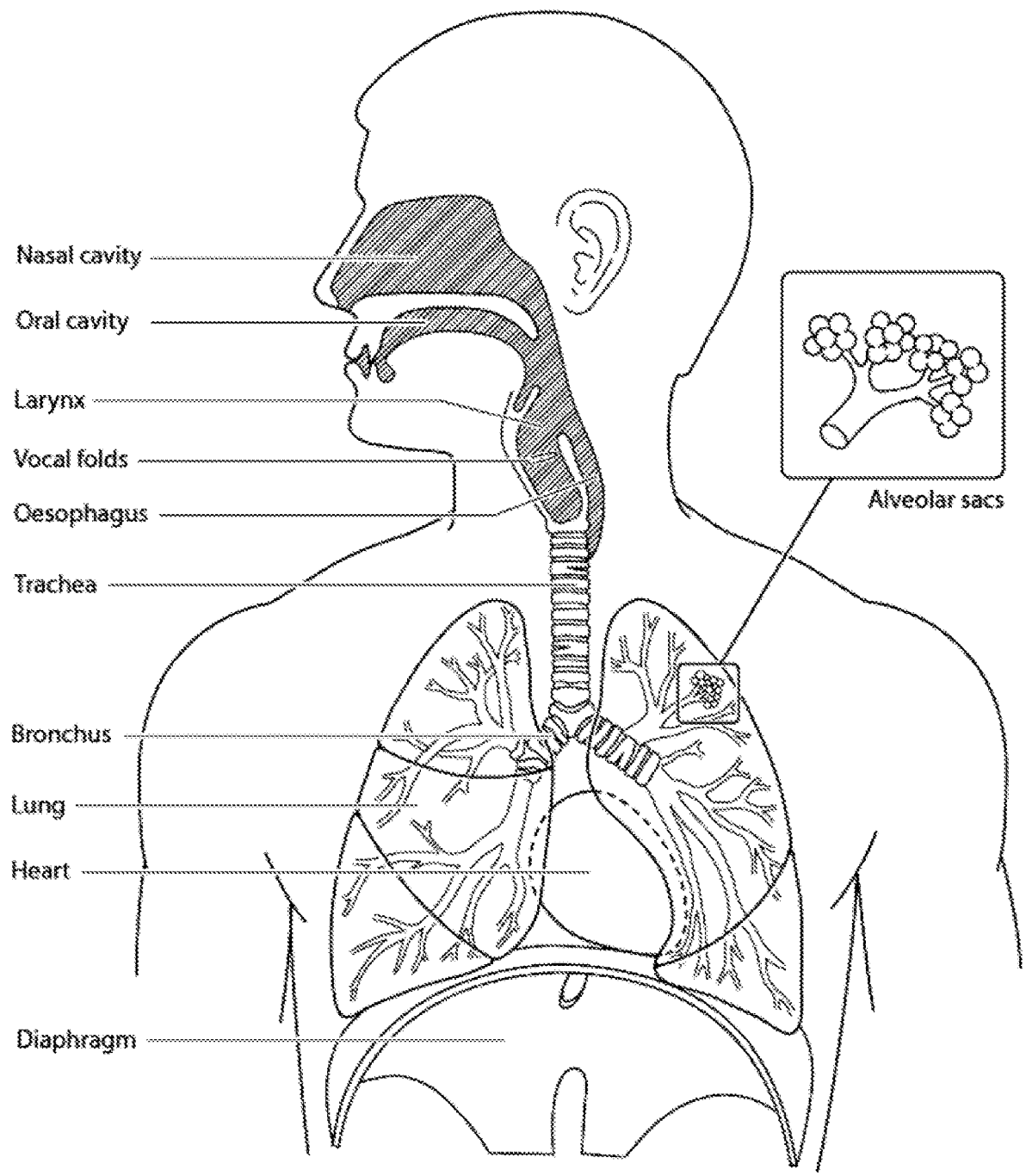

FIG. 2 shows an overview of a human respiratory system including the nasal and oral cavities, the larynx, vocal folds, oesophagus, trachea, bronchus, lung, alveolar sacs, heart and diaphragm.

Figure 3:
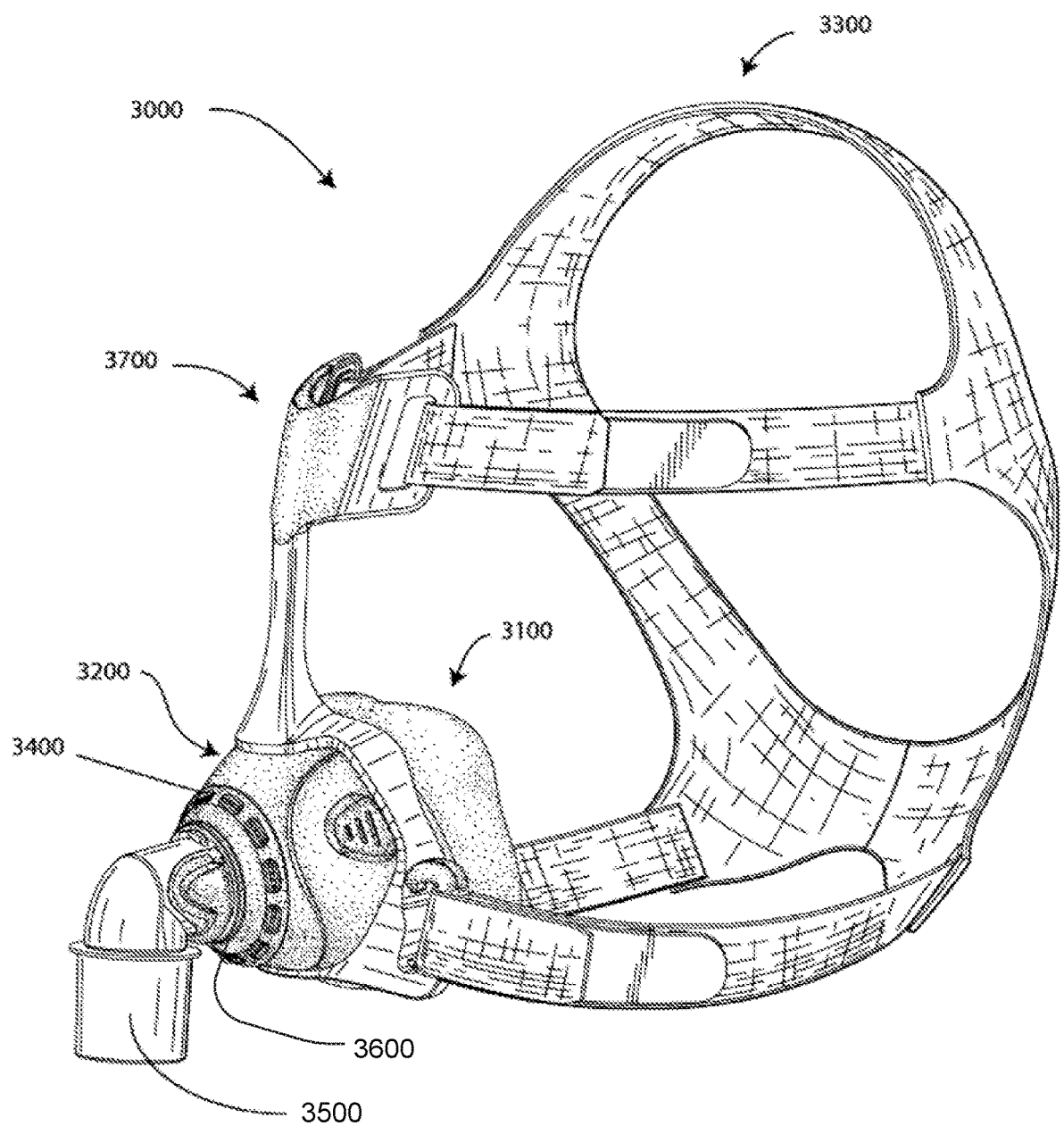

FIG. 3 shows a patient interface in the form of a nasal mask in accordance with one form of the present technology.

6.3 Combination Therapy (CT) Device

Figure 4A:
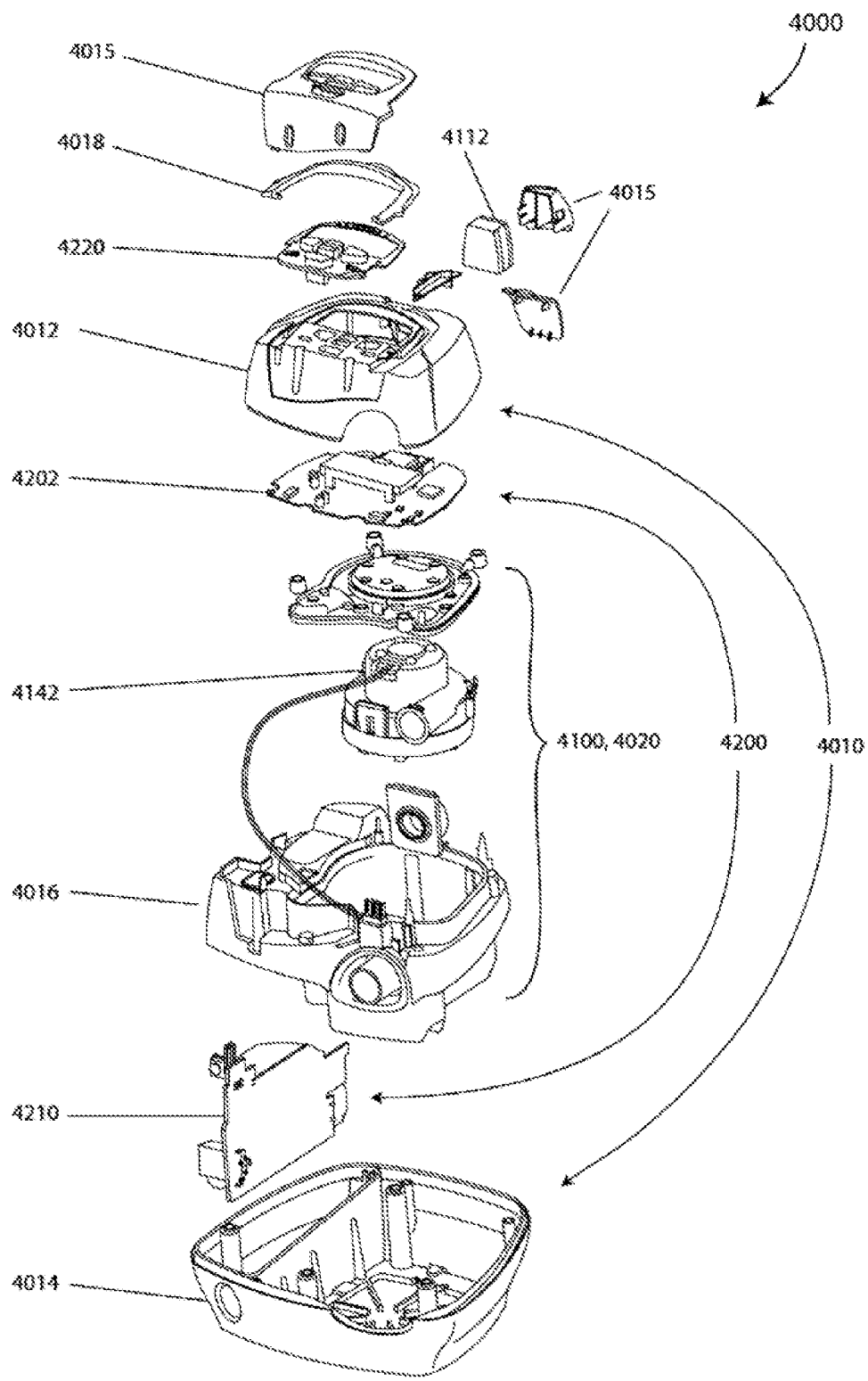

FIG. 4A shows example components of a CT device in accordance with one form of the present technology.

Figure 4B:
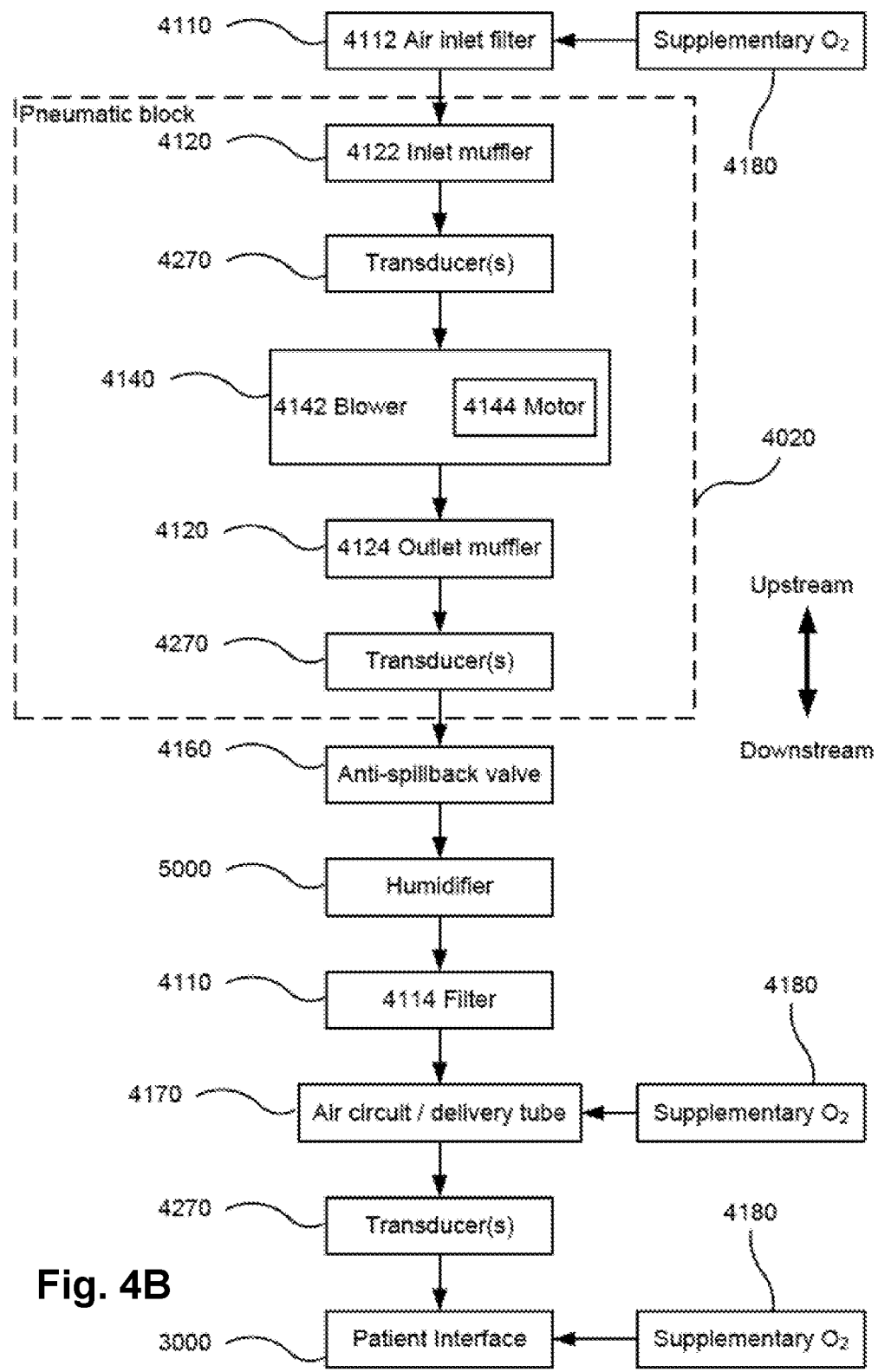

FIG. 4B shows a schematic diagram of either a pressure control or flow control pneumatic circuit of a CT device in accordance with one form of the present technology. The directions of upstream and downstream are indicated.

Figure 4C:
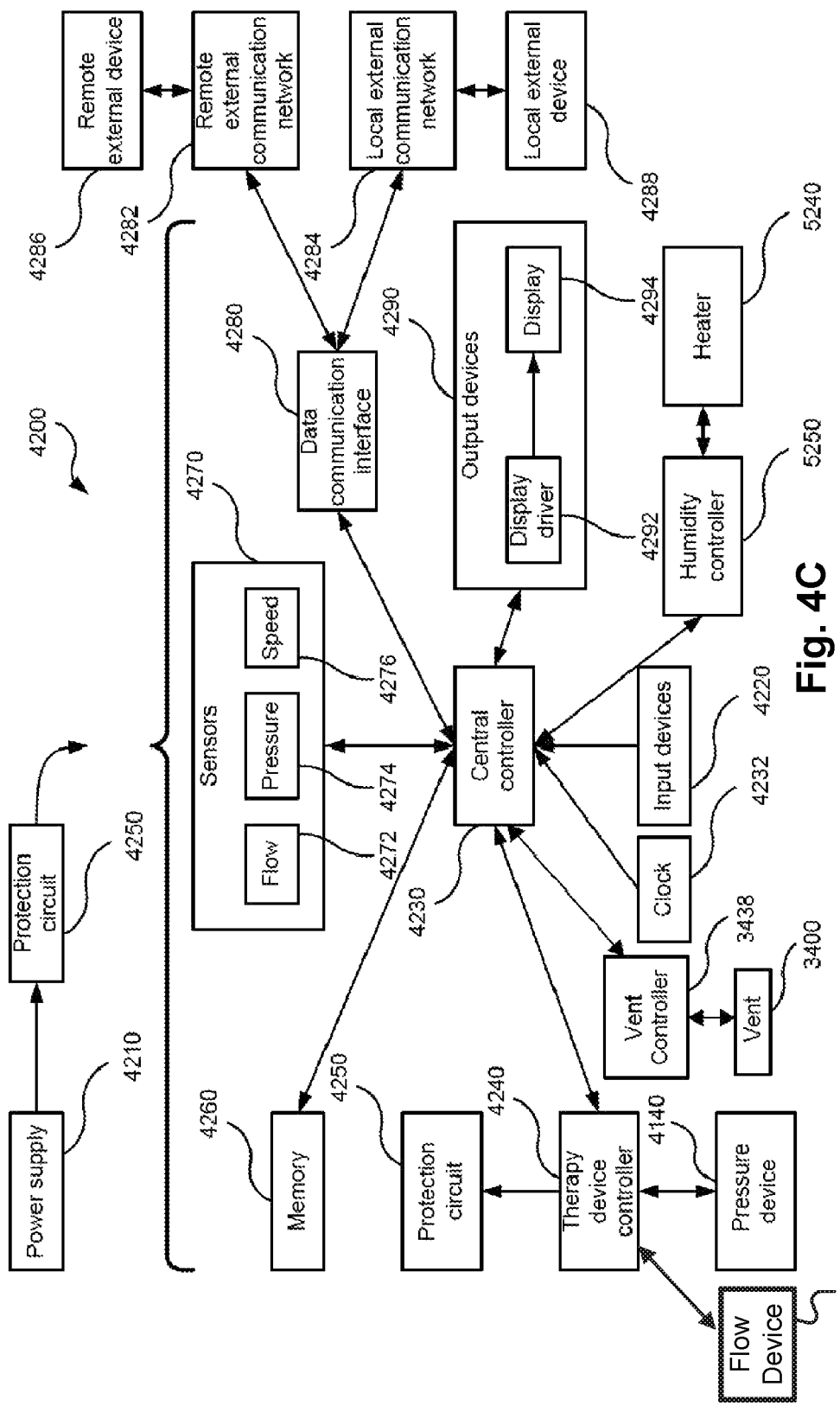

FIG. 4C shows a schematic diagram of the electrical components of a CT device in accordance with one aspect of the present technology.

6.4 Humidifier

Figure 5:
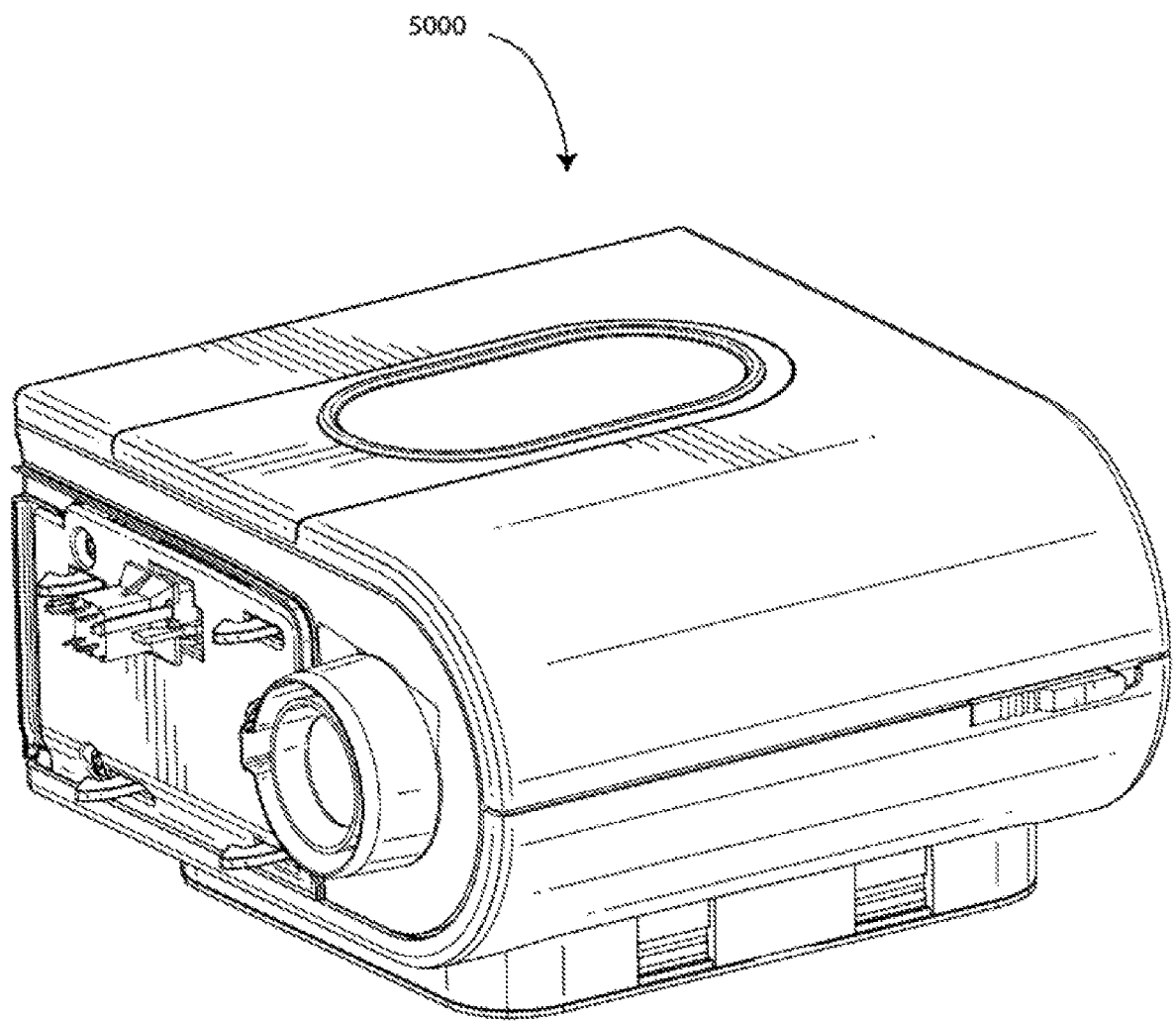

FIG. 5 shows an isometric view of a humidifier suitable for use with a respiratory apparatus.

6.5 Patient Interface

Figure 6:
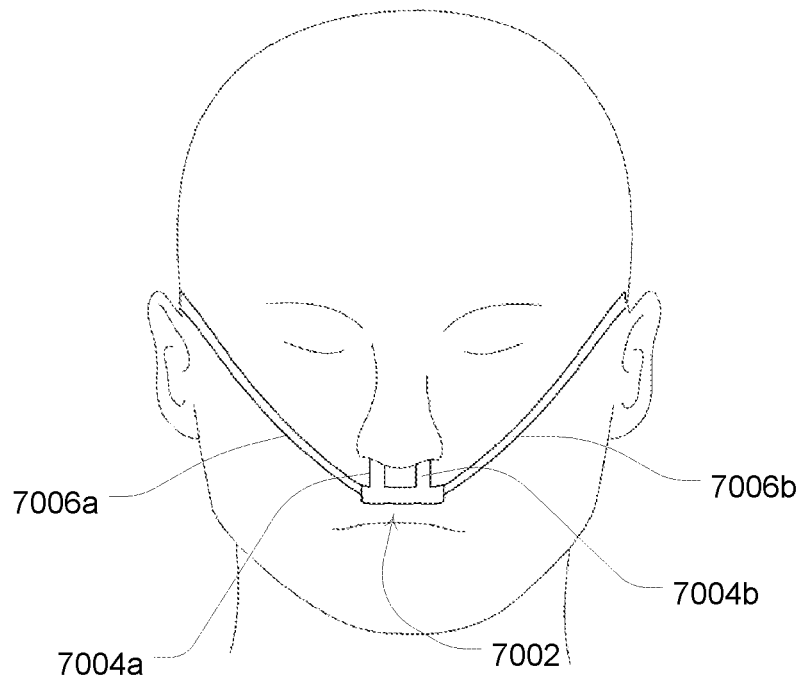
Figure 7:
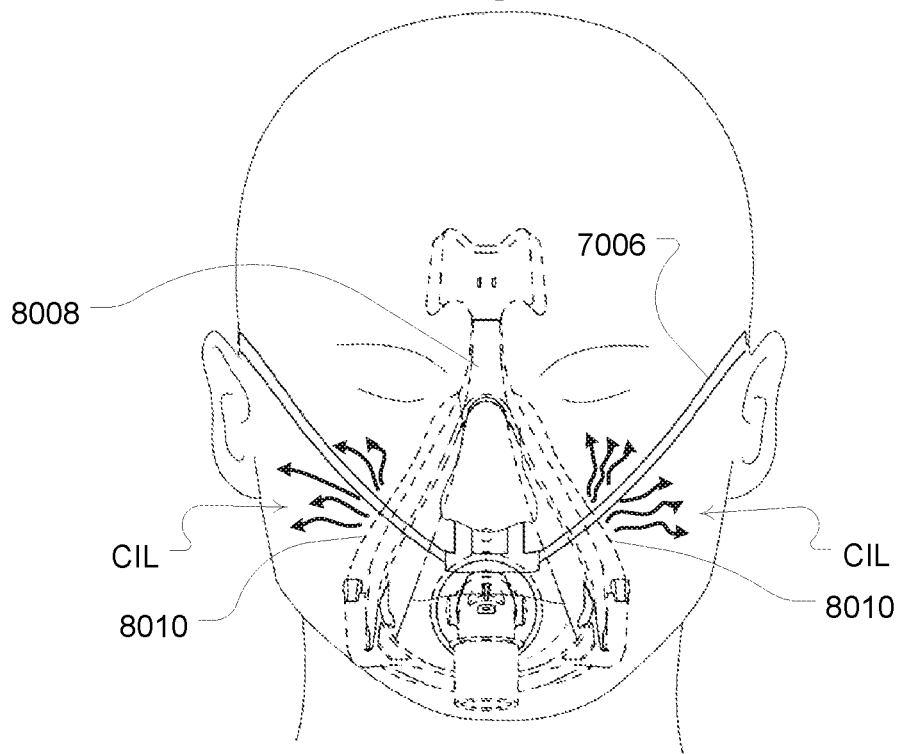
Figure 8:
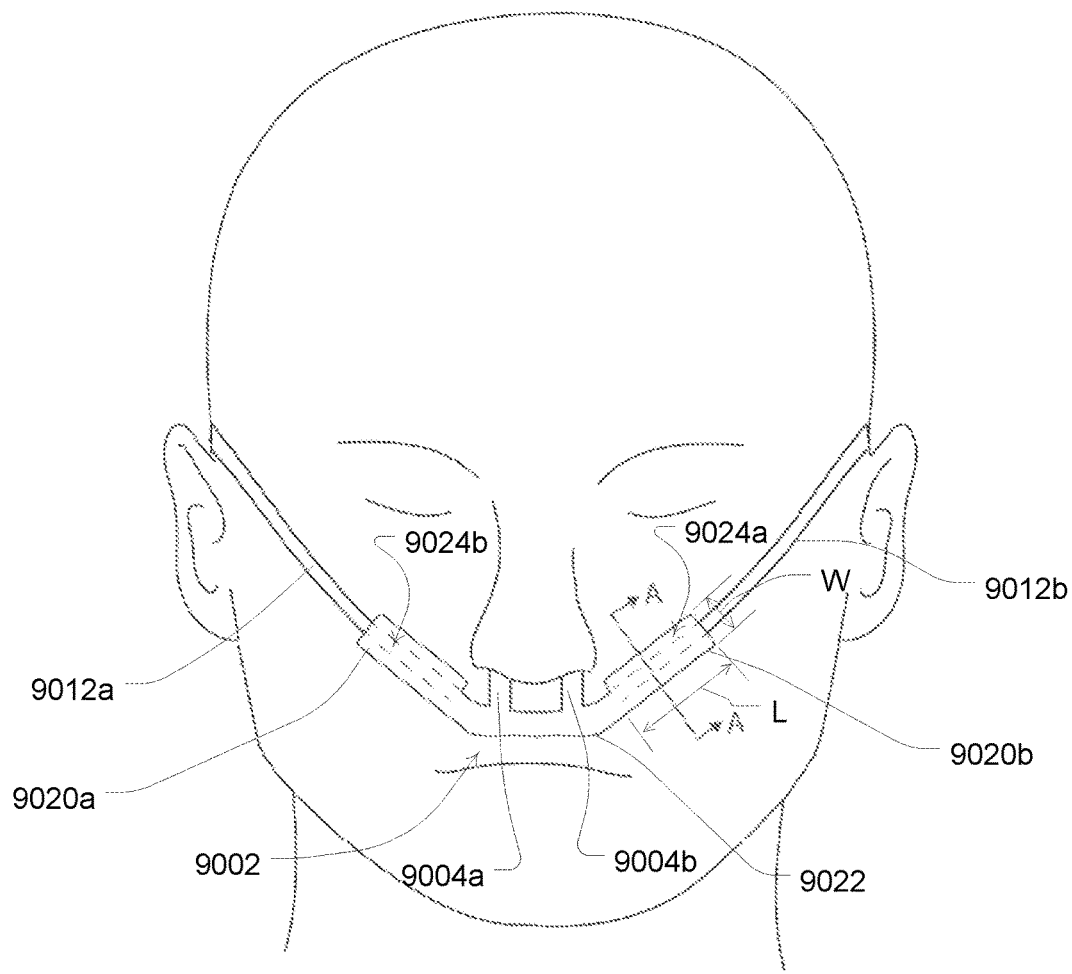
Figure 10A:
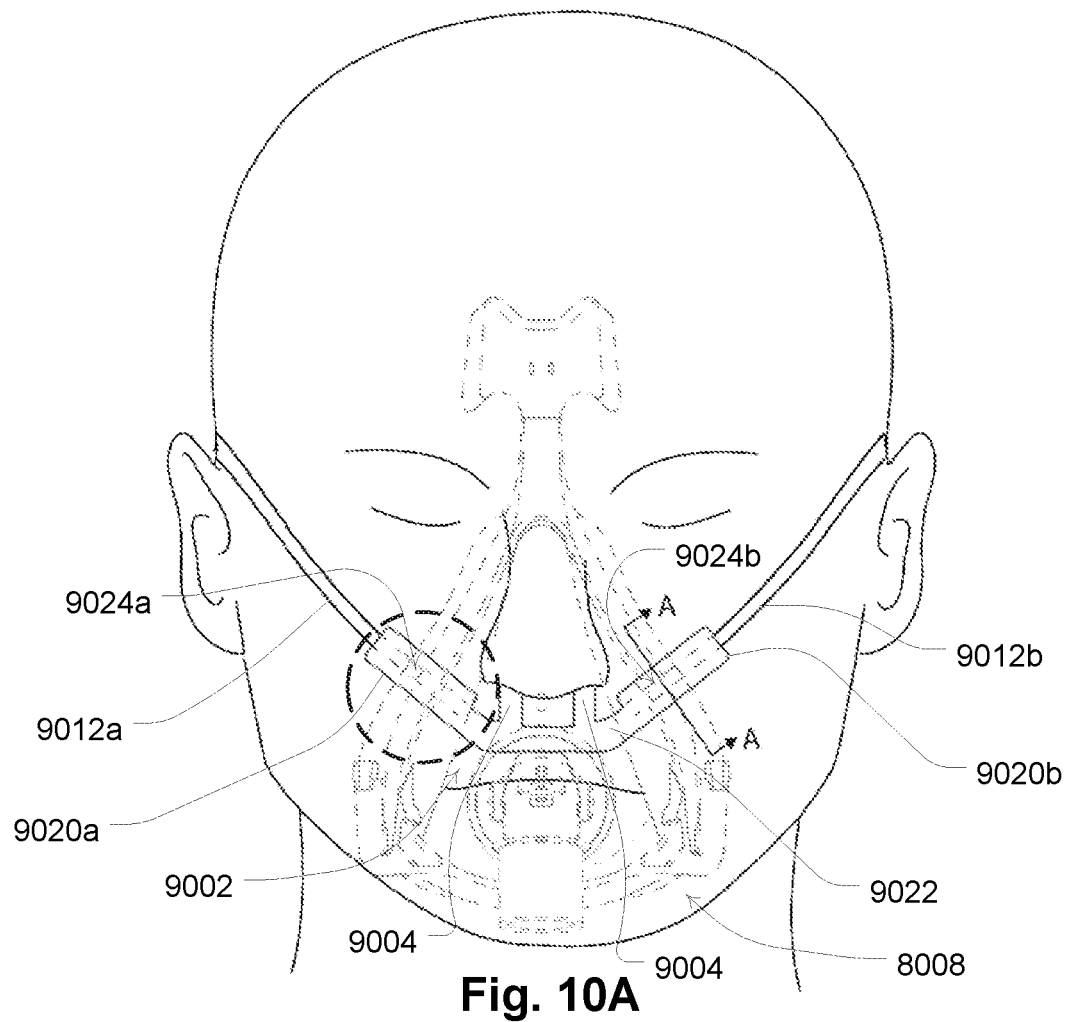
Figure 10B:
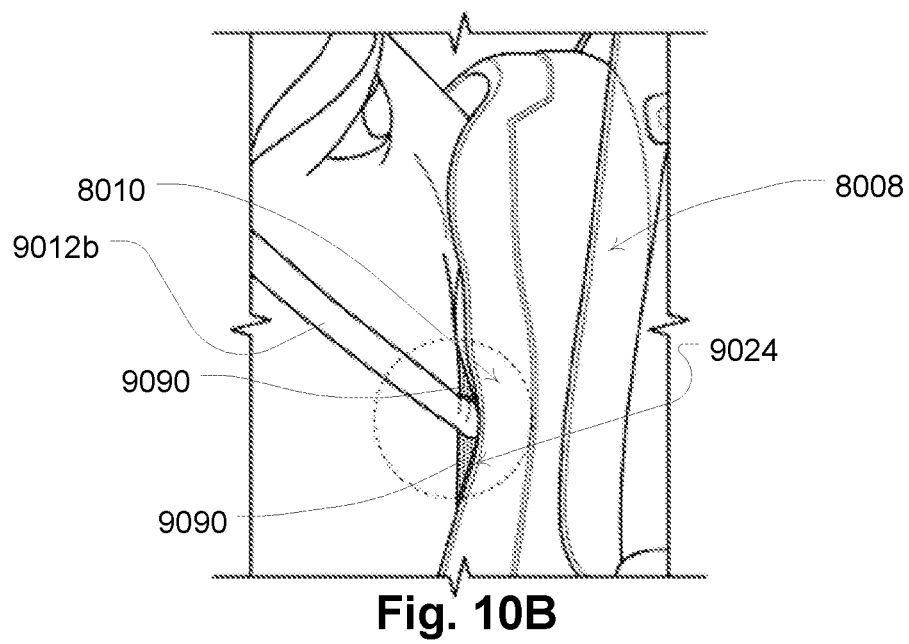
Figure 11:
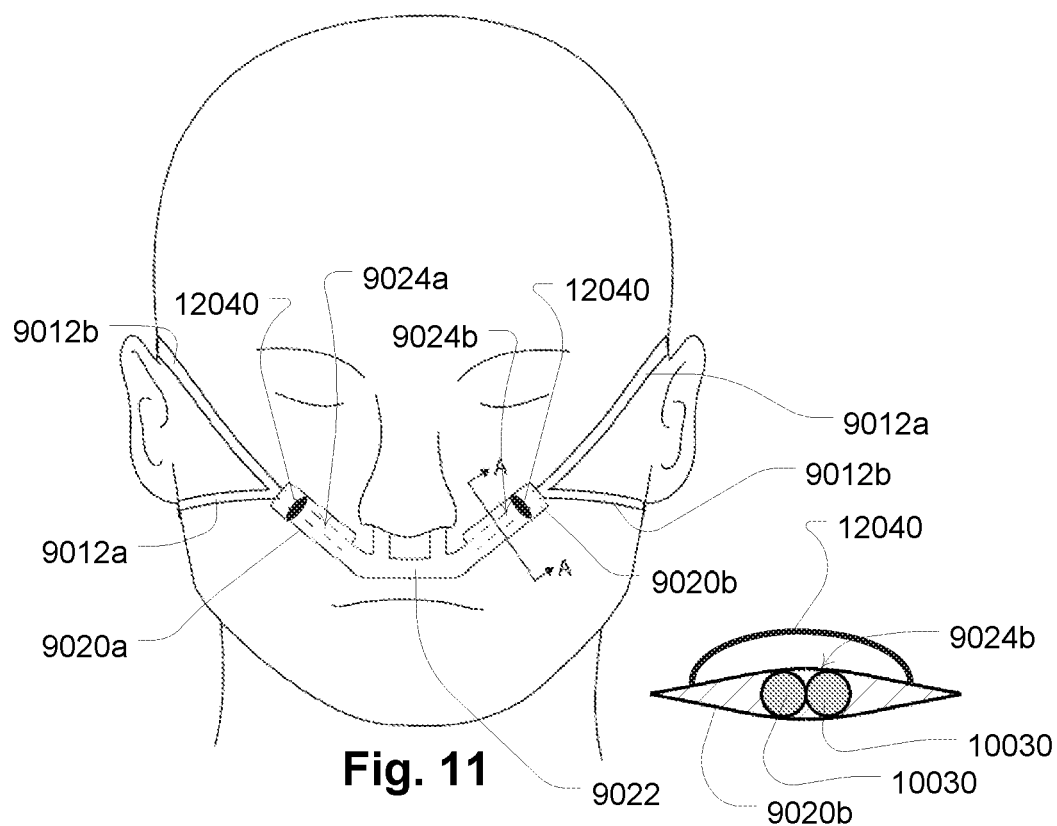
Figure 12:
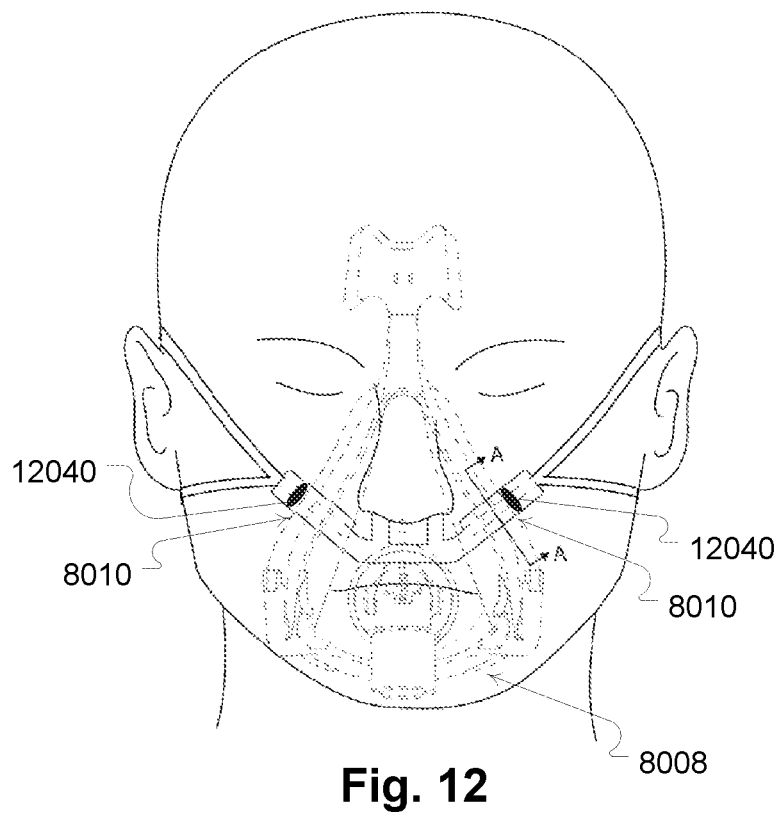
Figure 13:
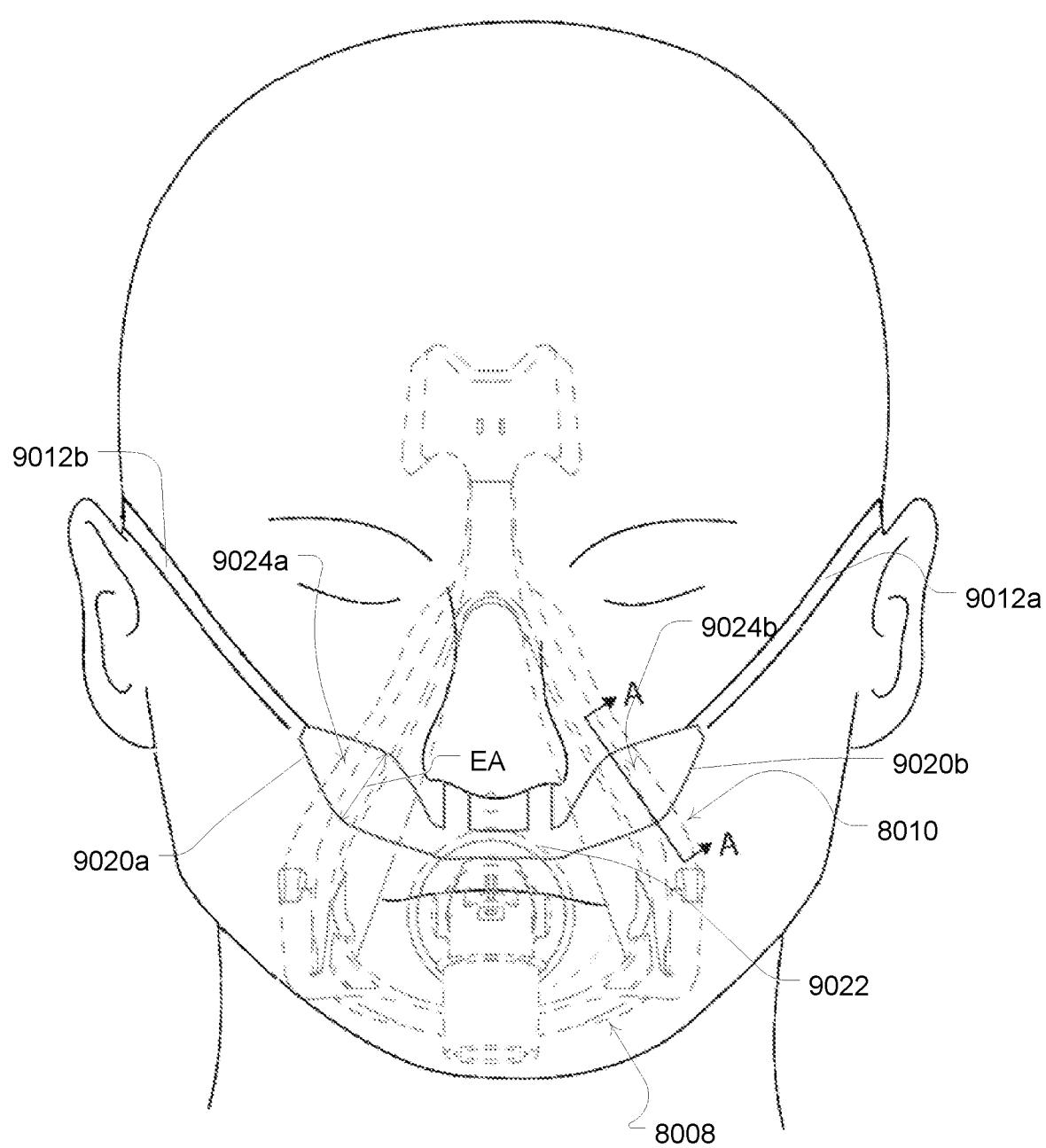
Figure 14A:
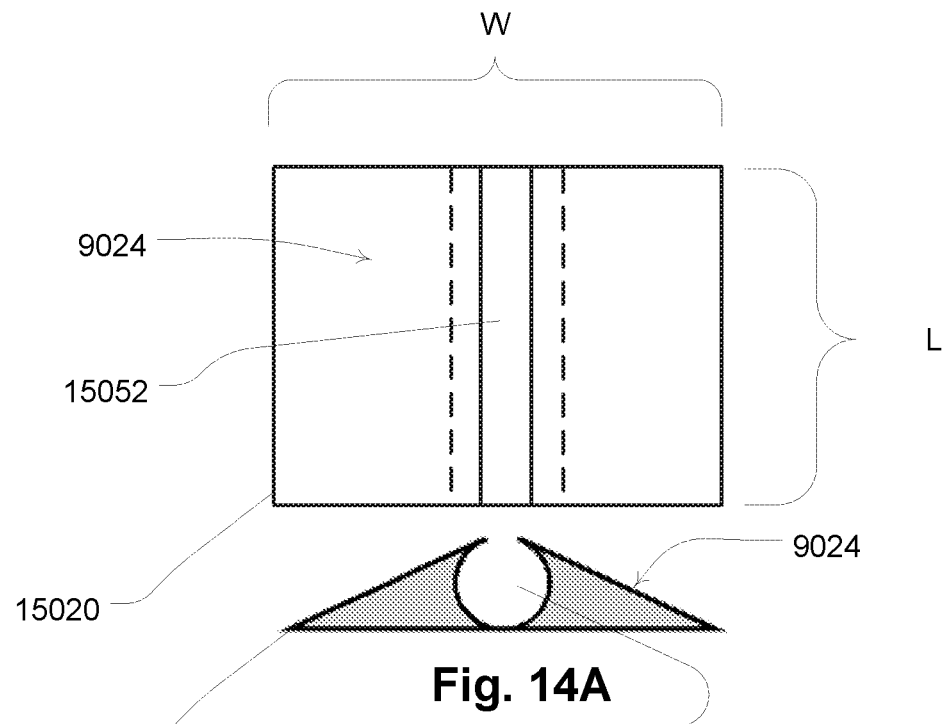
Figure 14B:
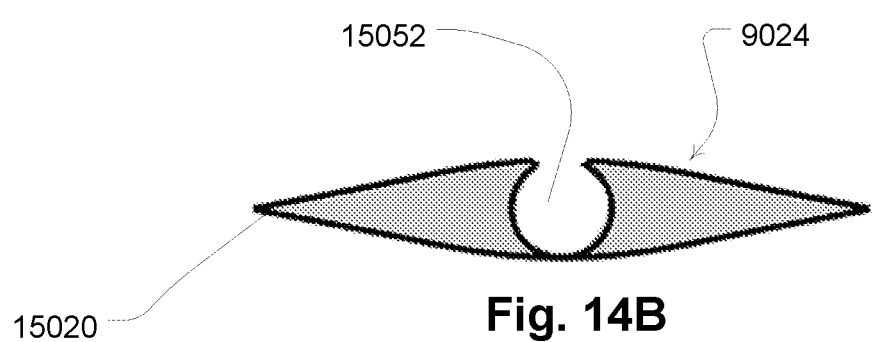
Figure 14C:
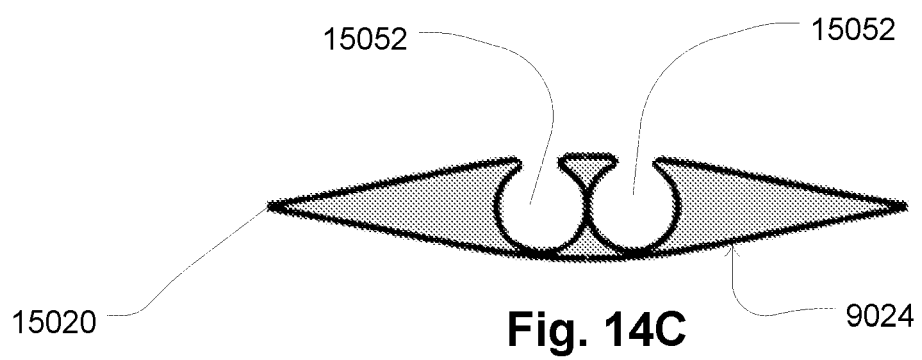
Figure 15A:
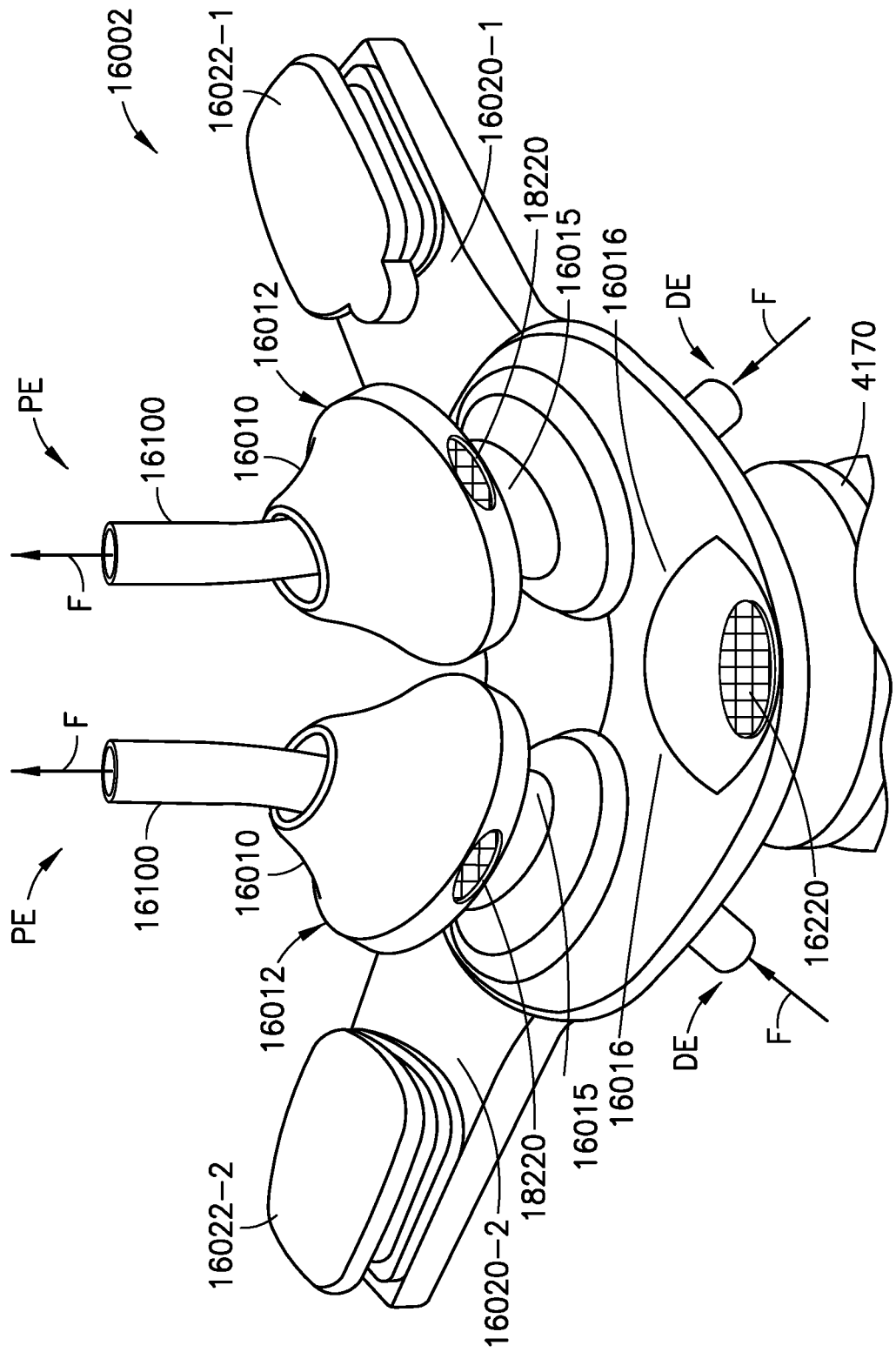
Figure 15B:
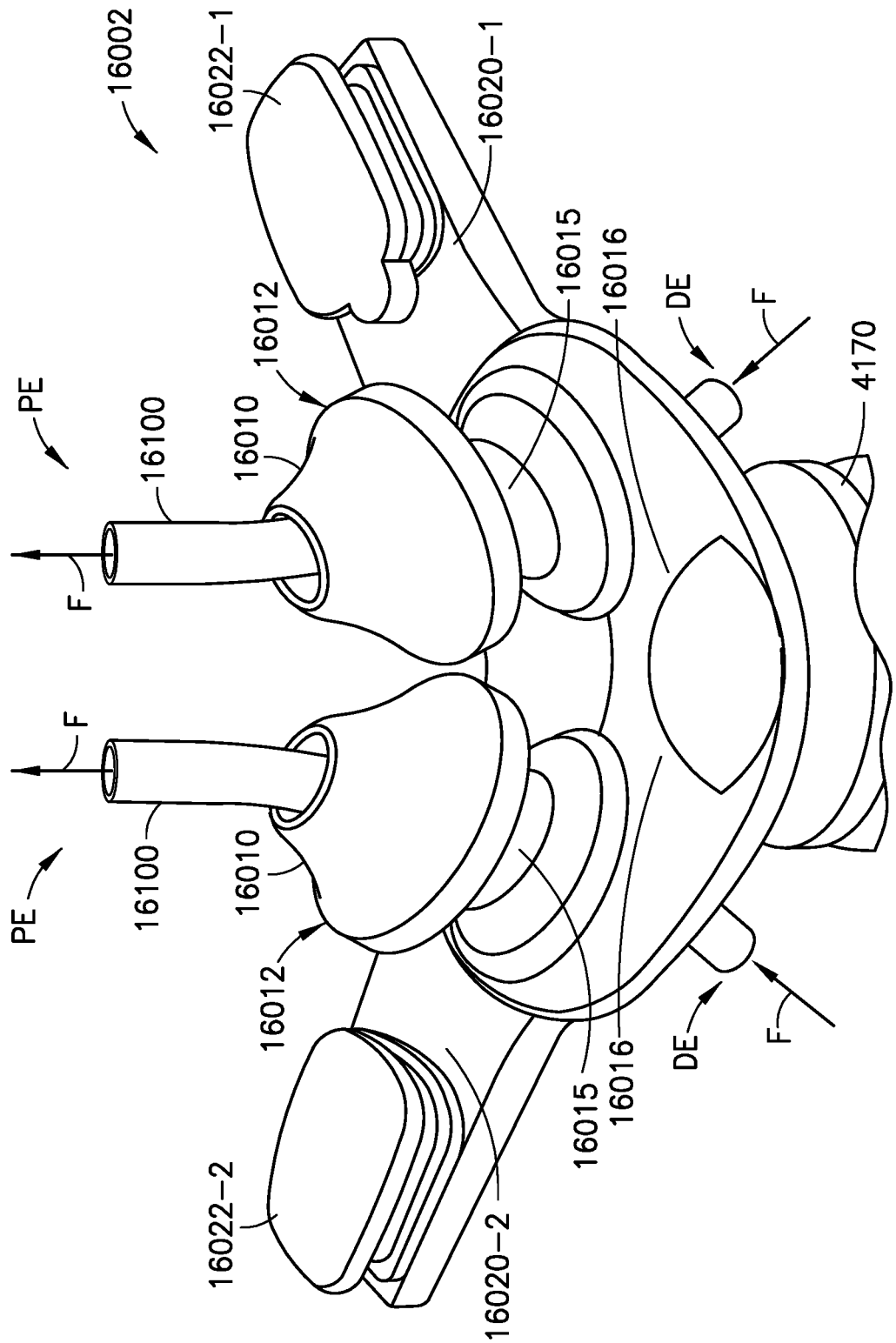
Figure 16:
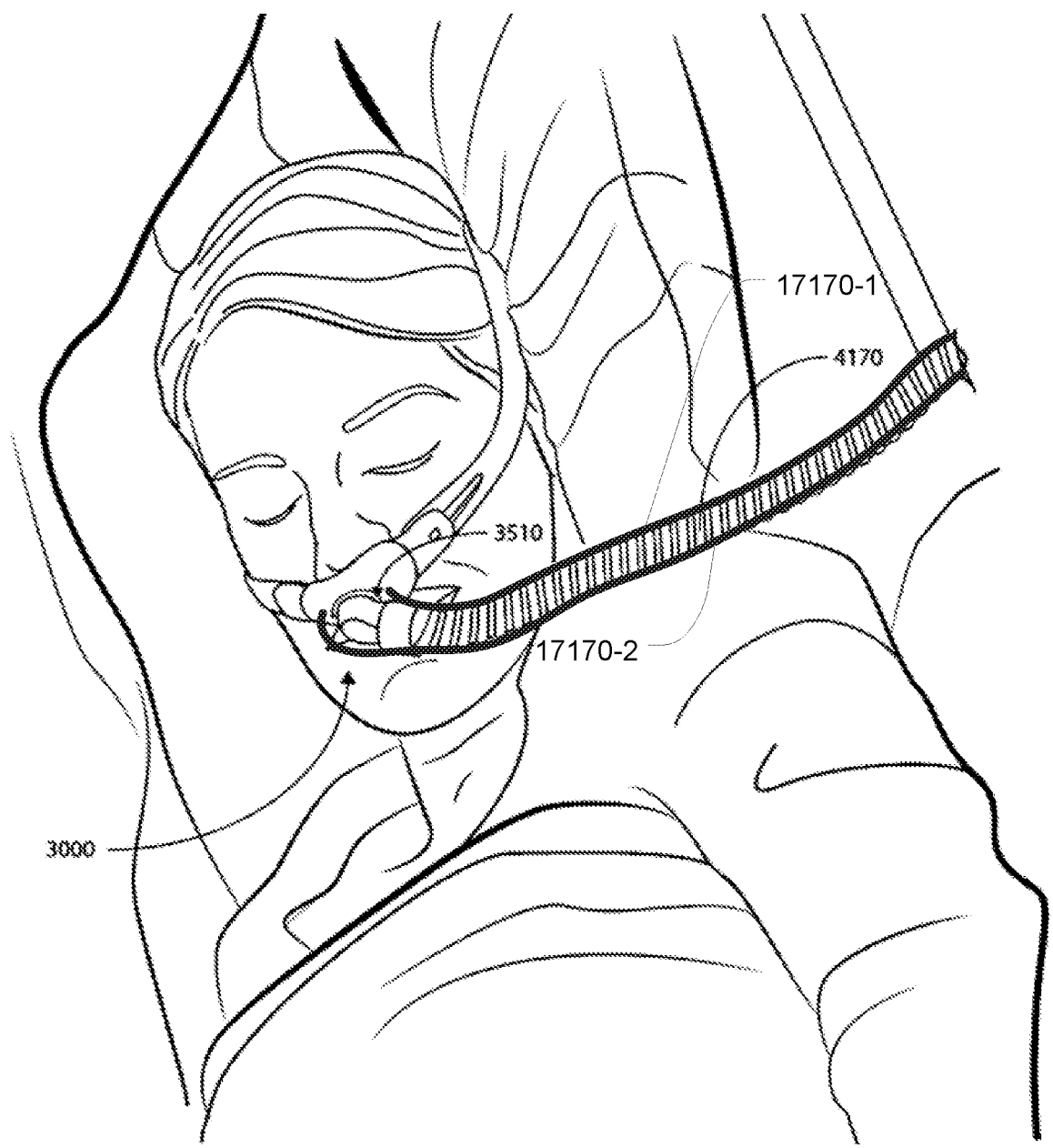
Figure 17A:
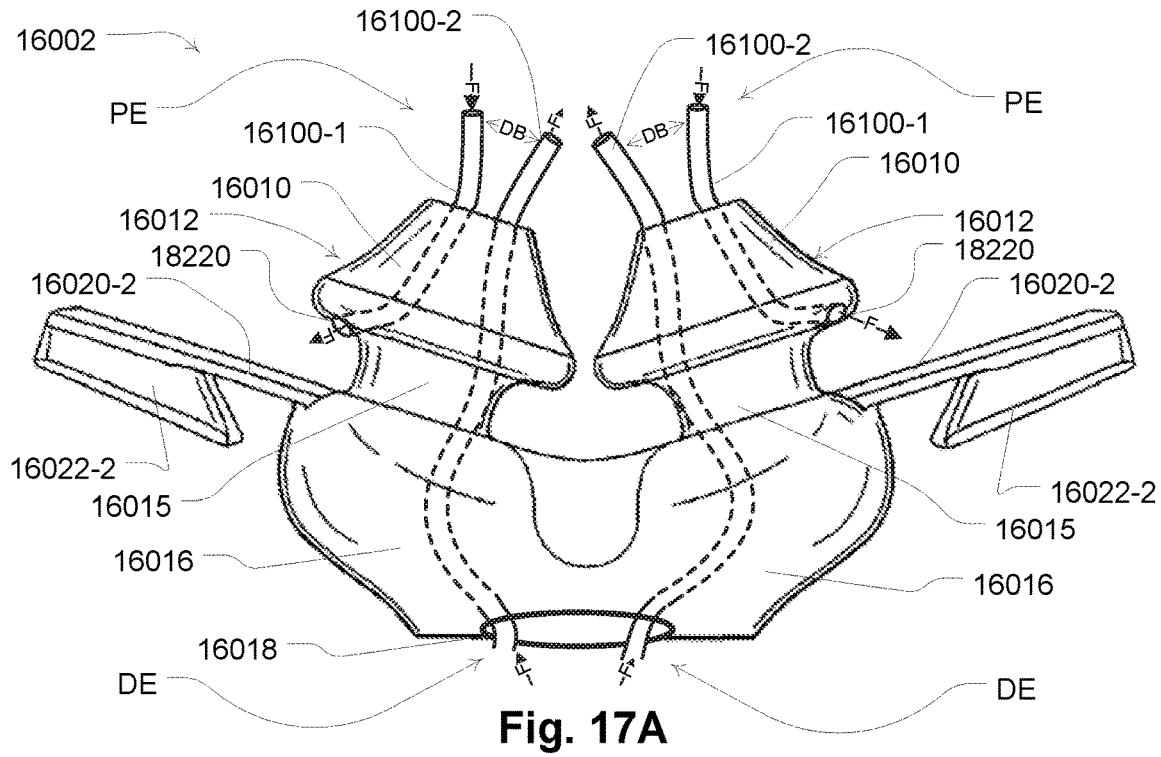
Figure 17B:
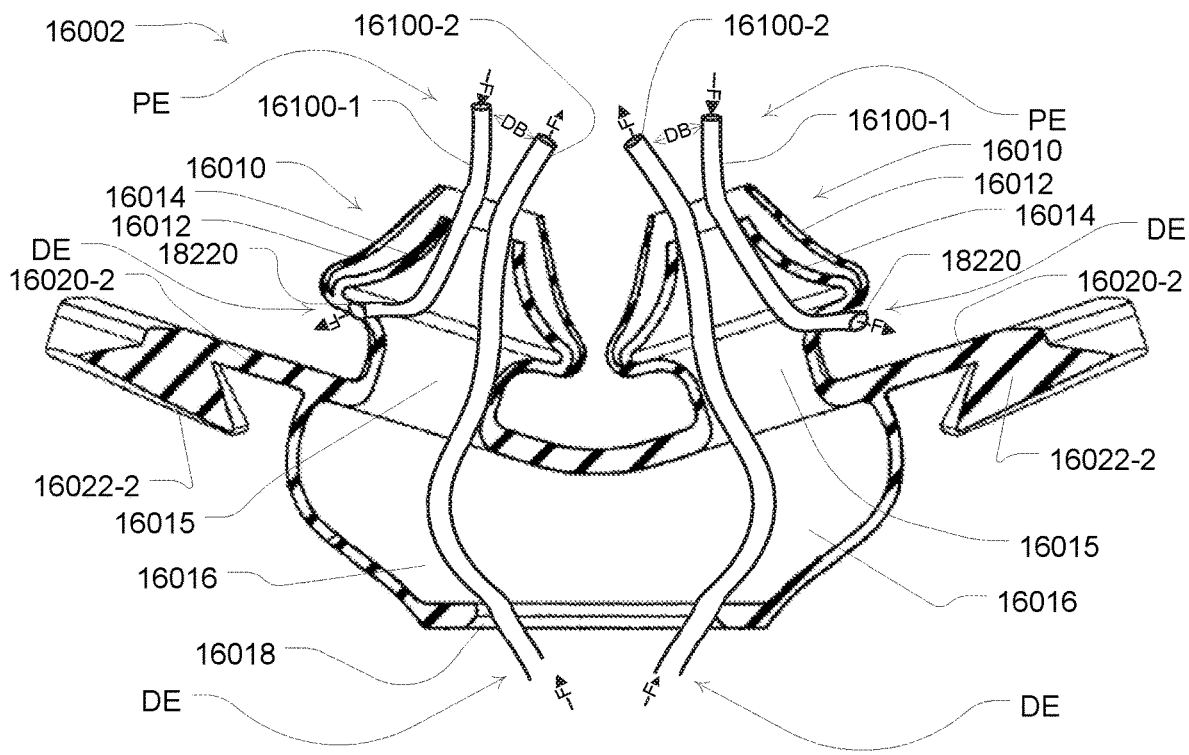
Figure 18:
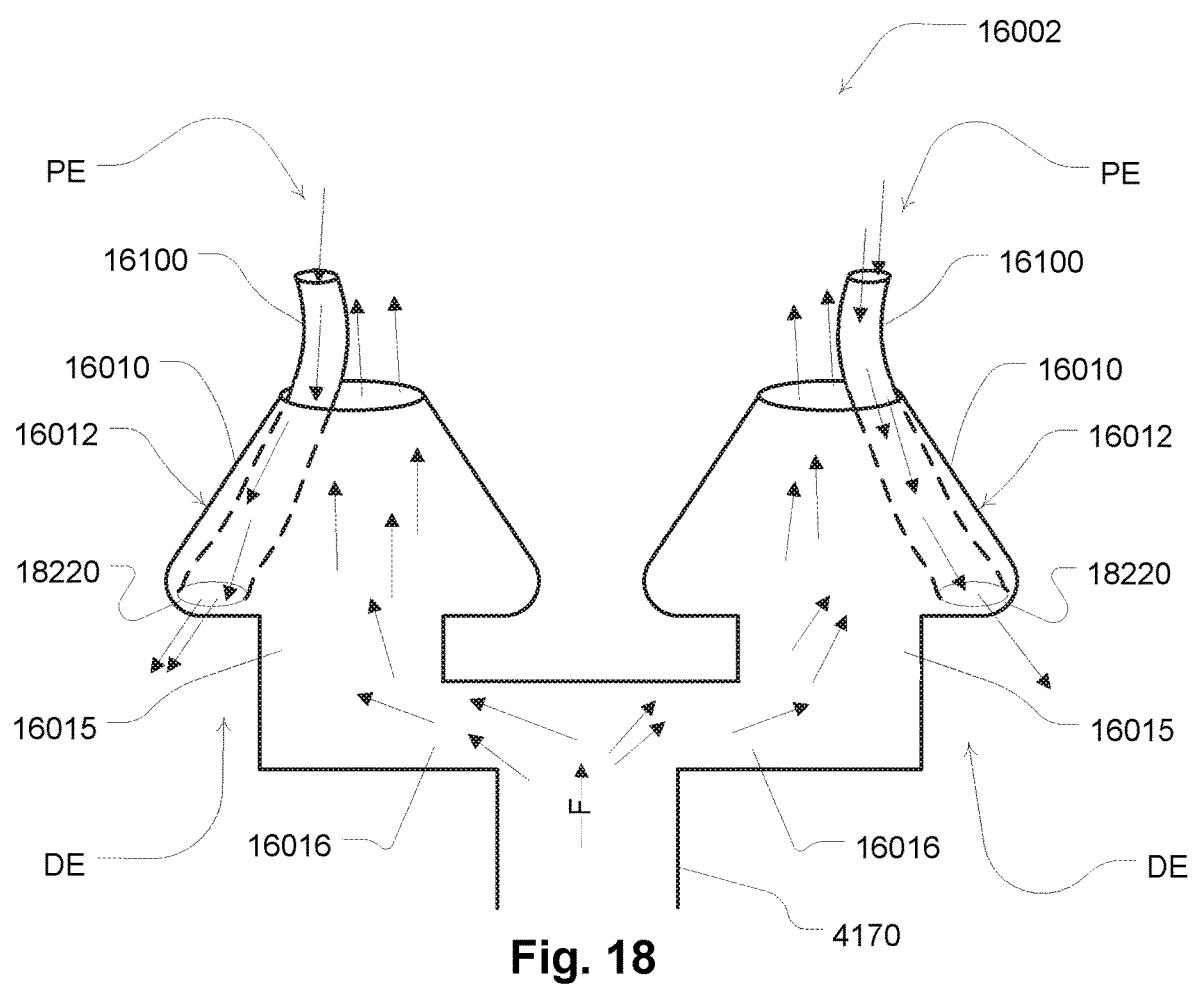
Figure 19A:
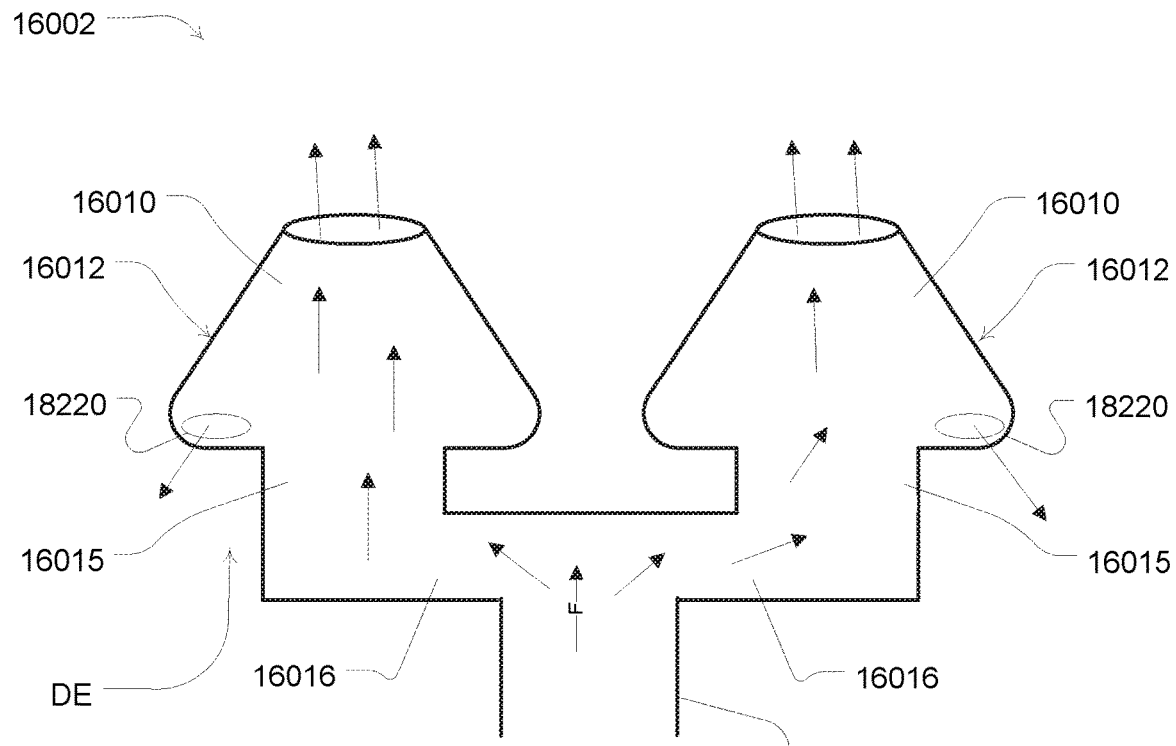
Figure 19B:
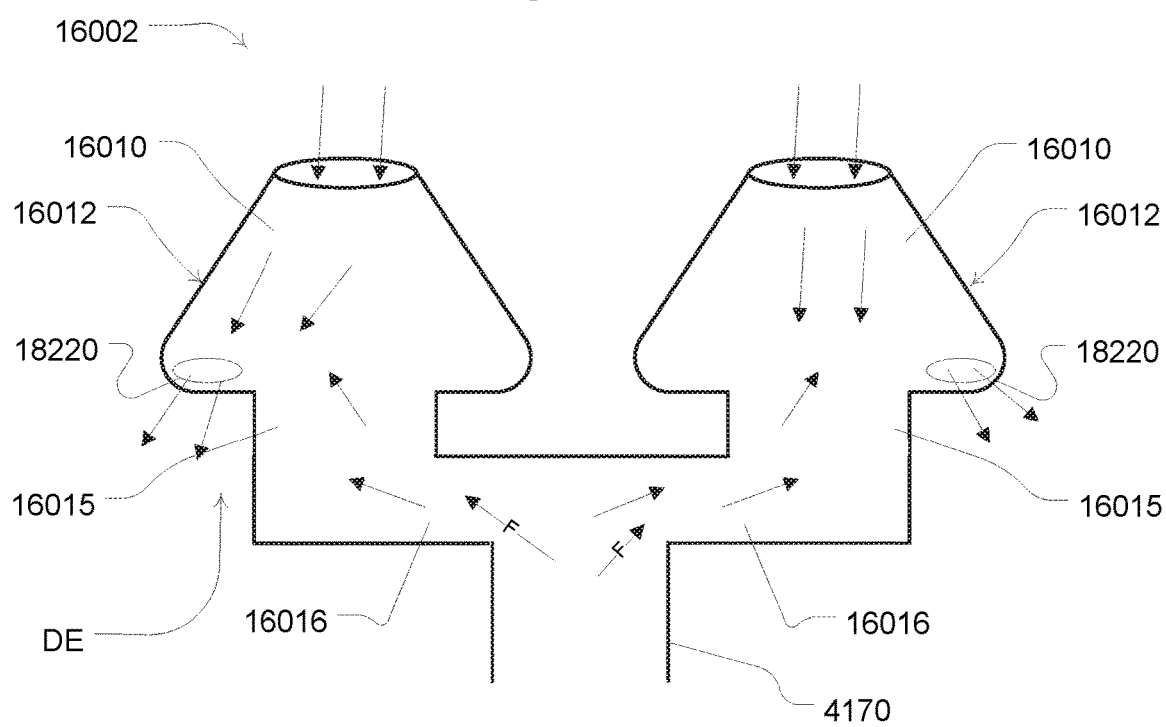
Figure 21:
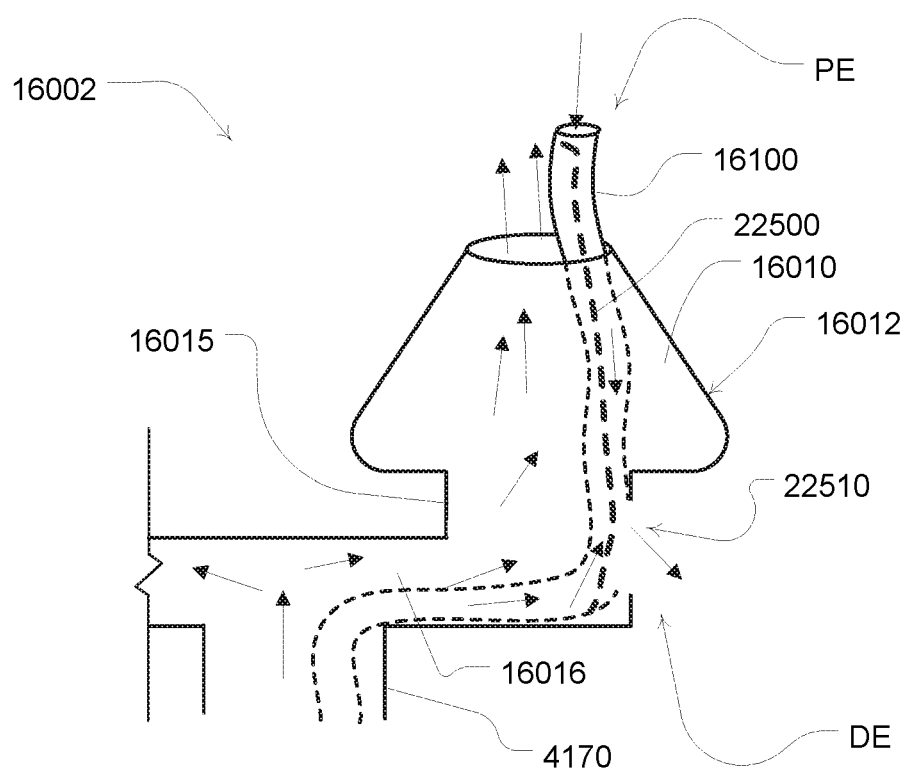
Figure 22:
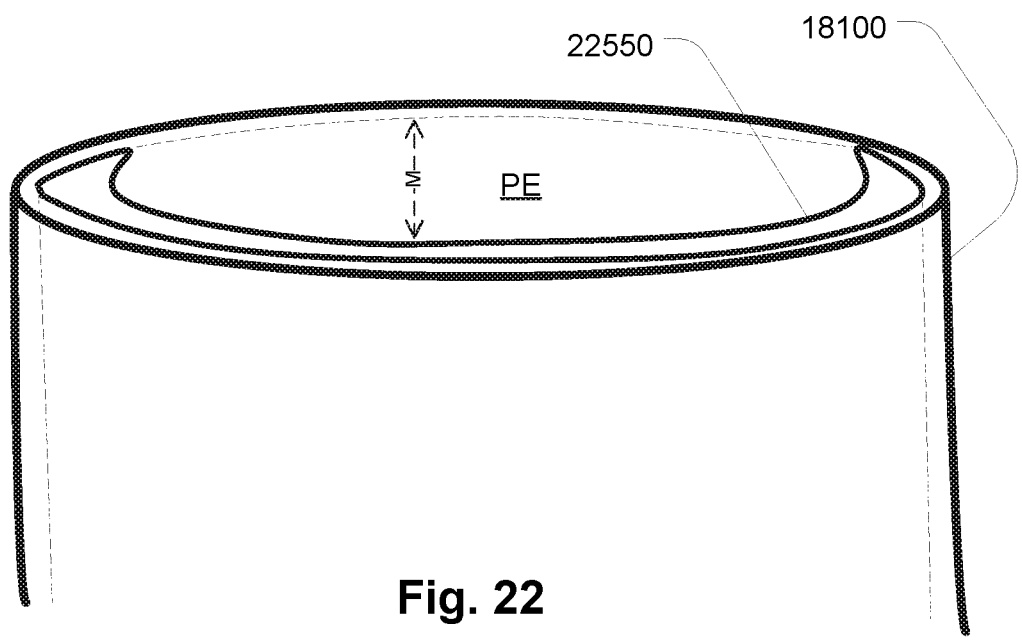
Figure 23A:
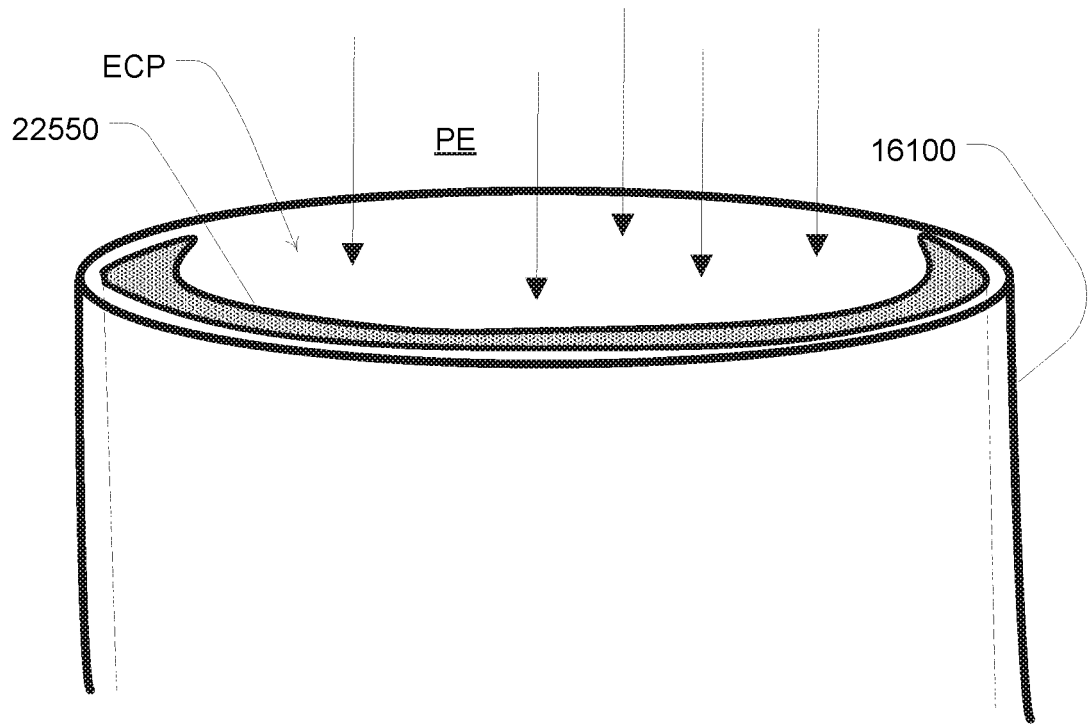
Figure 23B:
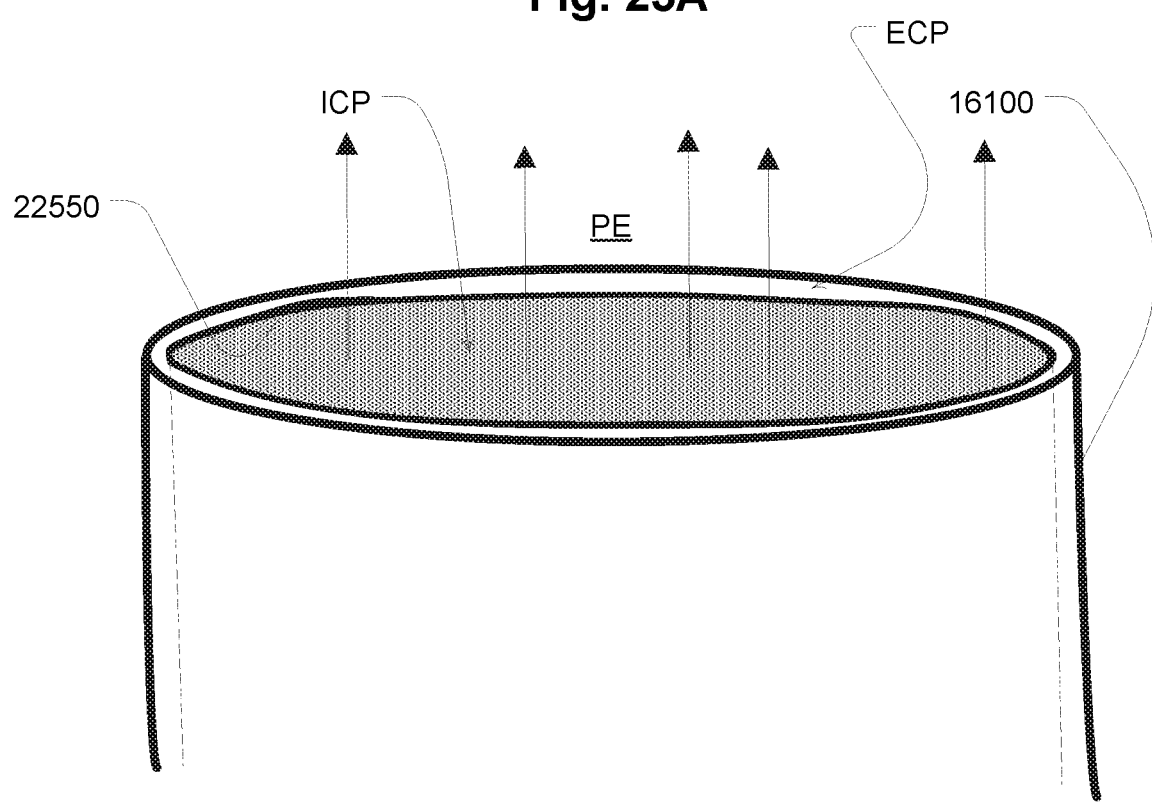
Figure 24:
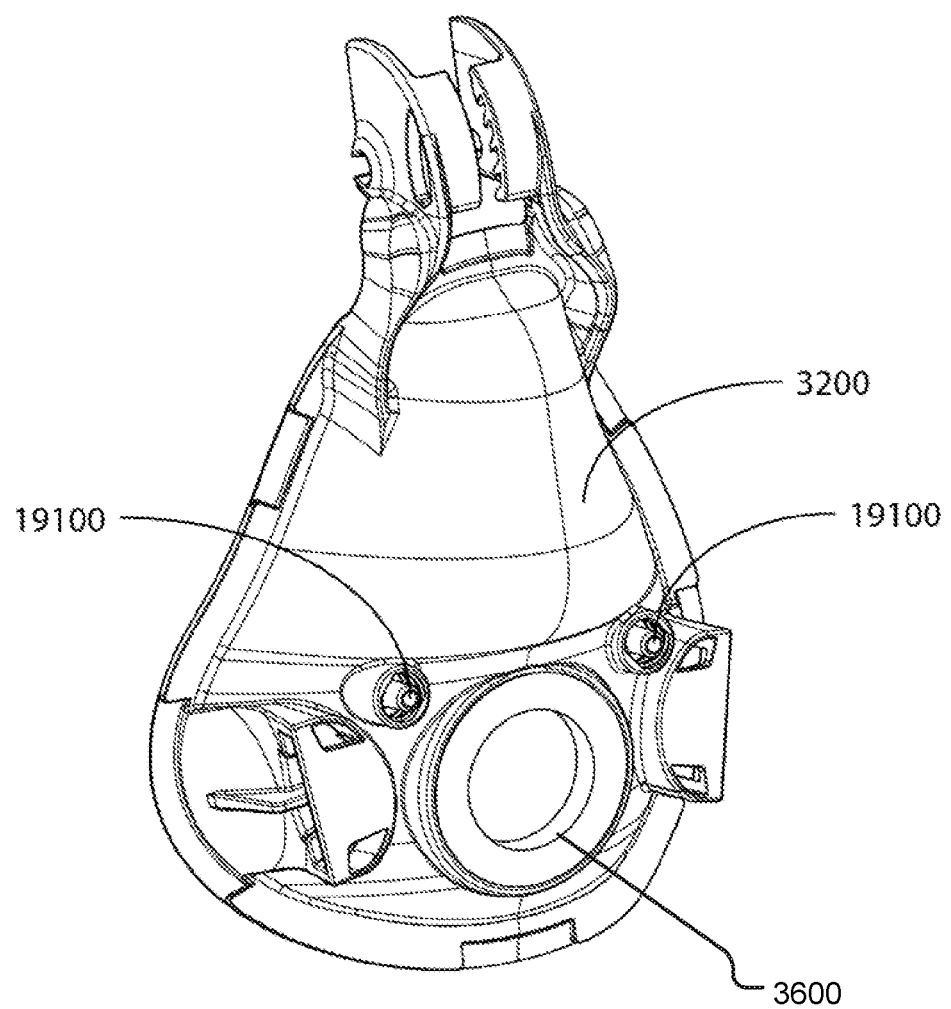
Figure 25A:
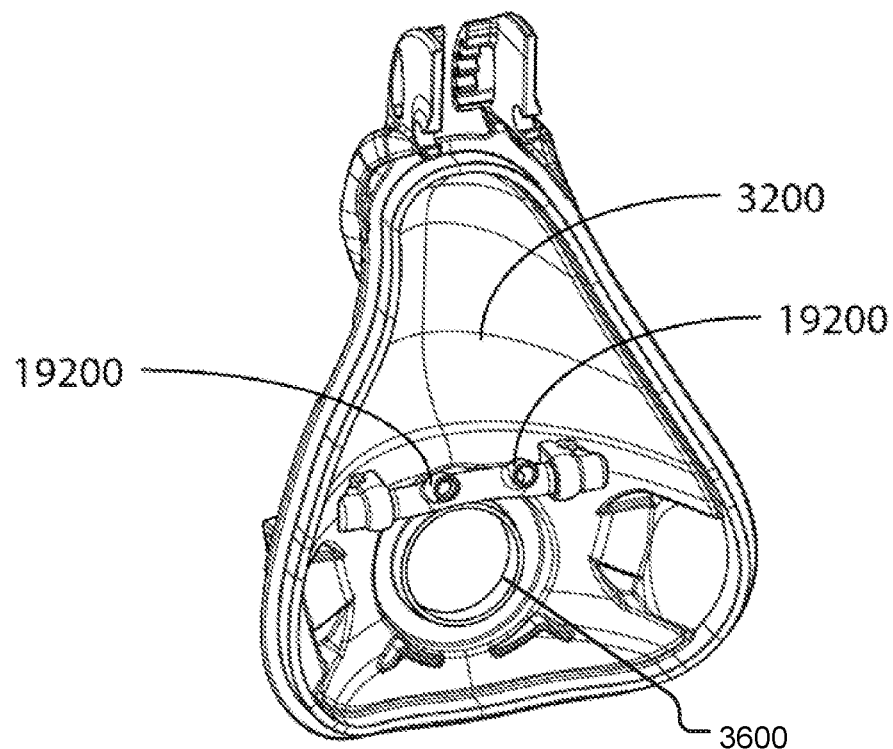
Figure 25B:
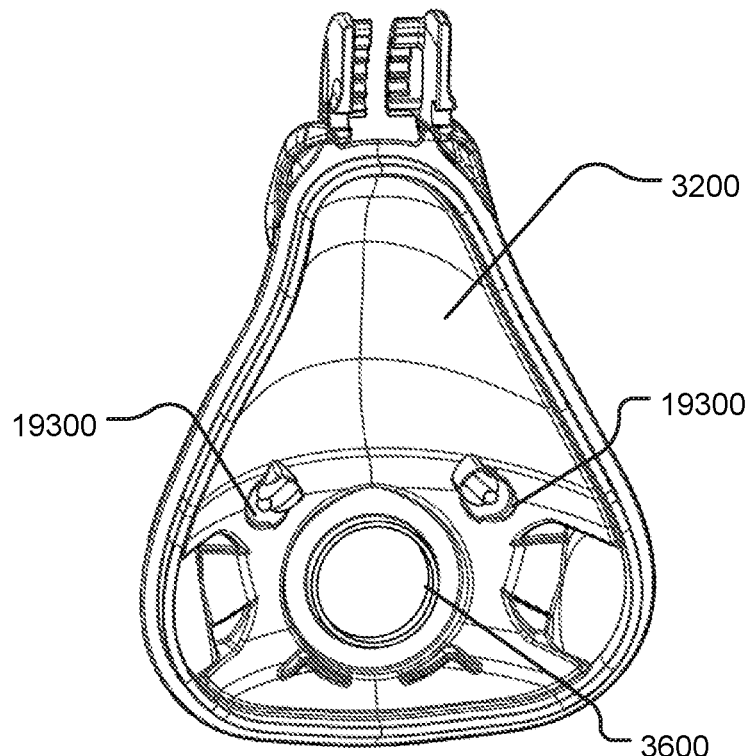

FIG. 6 shows a conventional nasal cannula;

FIG. 7 shows the nasal cannula of FIG. 6 in use with a mask;

FIG. 8 is an illustration of a nasal cannula with a coupler extension;

FIGS. 9A, 9B, 9C and 9D illustrate various cross sectional profiles for coupler extensions of the present technology taken along line A-A of FIG. 8;

FIG. 10A is an illustration of a nasal cannula with a coupler extension in use with a mask;

FIG. 10B is an illustration of a nasal cannula with a coupler extension in use with a mask showing a seat portion;

FIG. 11 is another illustration of a nasal cannula with a coupler extension having a seat ridge, the figure also includes a cross sectional view of the coupler extension taken along line A-A;

FIG. 12 is another illustration of a nasal cannula with a coupler extension FIG. 11 in use with a mask;

FIG. 13 is an illustration of another version of a nasal cannula with a coupler extension in use with a mask;

FIG. 14A is a plan view and a front elevation view of another example coupler extension for a nasal cannula of the present technology;

FIG. 14B is a front elevation view of another coupler extension for a nasal cannula;

FIG. 14C is a front elevation view of another coupler extension for a nasal cannula;

FIG. 15A is an illustration nasal interface of the present technology with nasal projections;

FIG. 15B is an illustration of another nasal interface with nasal projections;

FIG. 16 shows the nasal interface of FIG. 15A in use by a patient;

FIG. 17A and 17B show elevation and cross sectional views respectively of a further example nasal interface;

FIG. 18 is an illustration of a further nasal interface with a pillow vent;

FIG. 19A and 19B are illustrations of a further nasal interface with pillow vents in showing inspiratory flow and expiratory flow respectively;

FIG. 20A and 20B are illustrations of a further nasal interface with vents showing expiratory and inspiratory operations respectively;

FIG. 20C and 20D are illustrations of a further nasal interface with vents showing expiratory and inspiratory operations respectively;

FIG. 20E and 20F are illustrations of a further nasal interface with vents showing expiratory and inspiratory operations respectively;

FIG. 21 is an illustration of a nasal pillow with a further example nasal projection;

FIG. 22 is an illustration of a valve membrane of the example nasal projection of FIG. 21;

FIGS. 23A and 23B show expiratory and inspiratory operations respectively of the valve membrane of the example nasal projection of FIG. 21;

FIG. 24 illustrates an external side view of a mask frame with interface ports for coupling with supply conduits;

FIG. 25A shows a plenum chamber or patient side of a mask frame for some versions of the present technology;

FIG. 25B shows another plenum chamber or patient side of a mask frame of another version of the present technology;

6.6 Combination Therapy System

Figure 26:
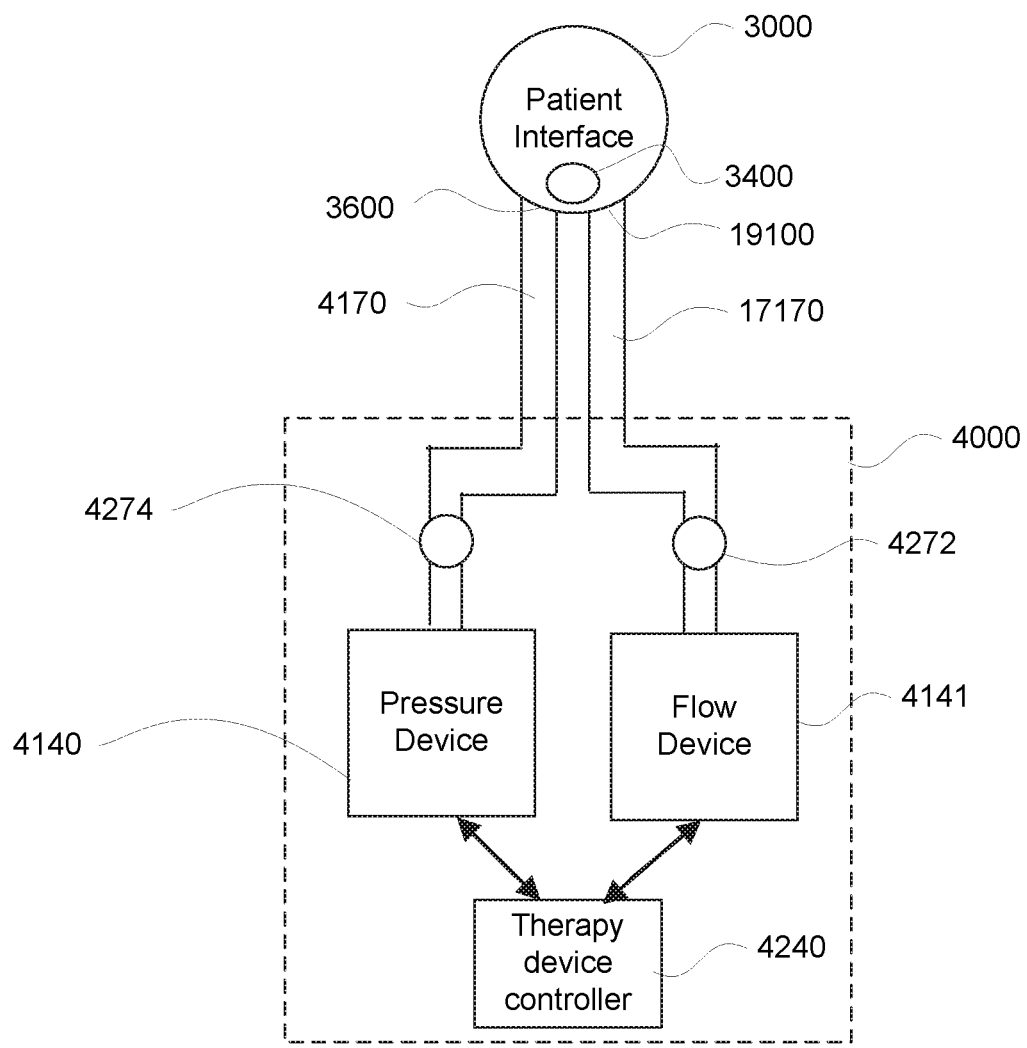
Figure 27:
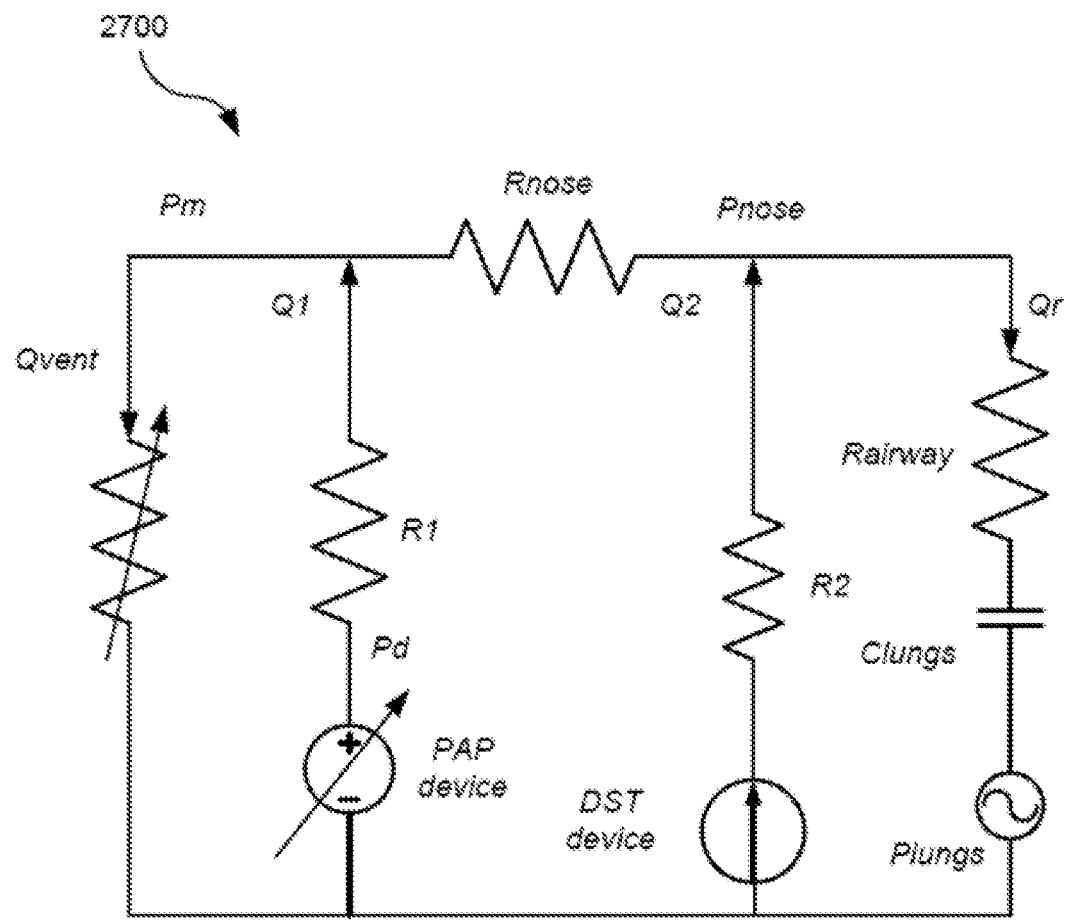
Figure 28:
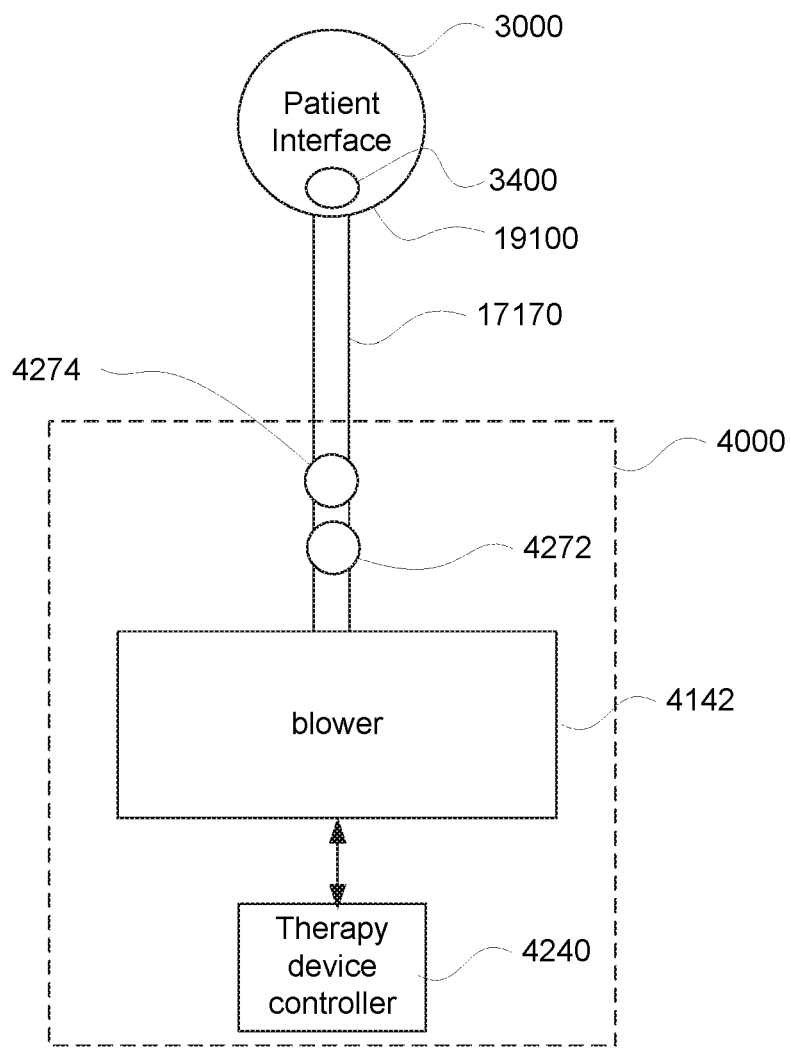
Figure 29:
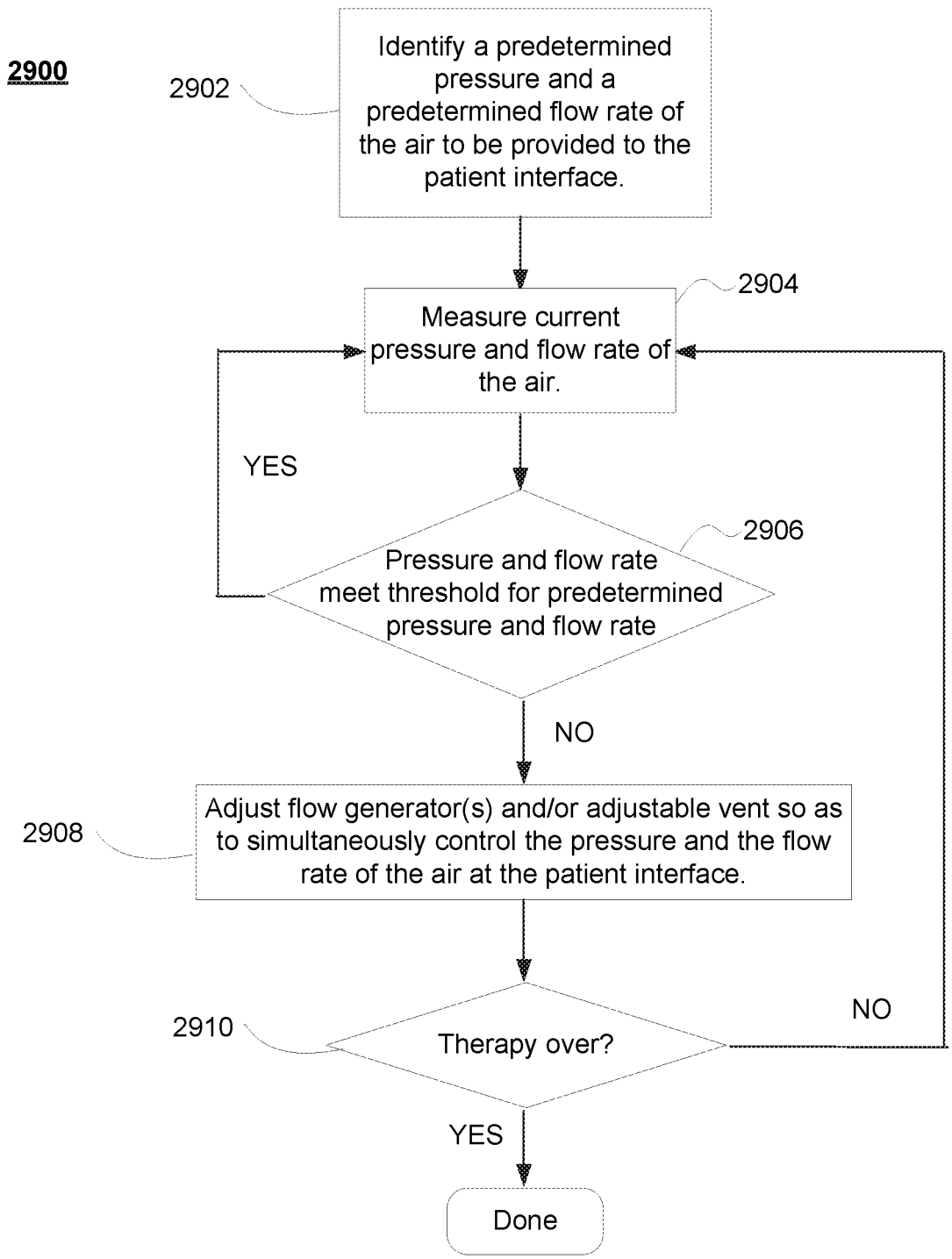
Figure 30:
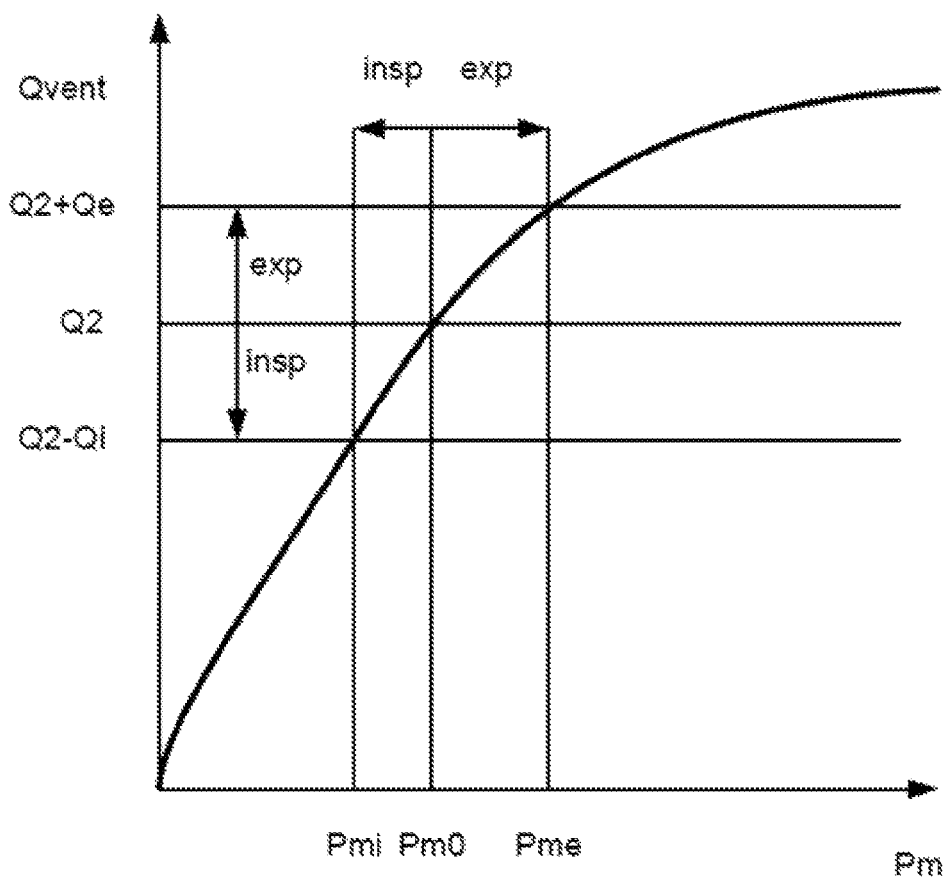
Figure 31:
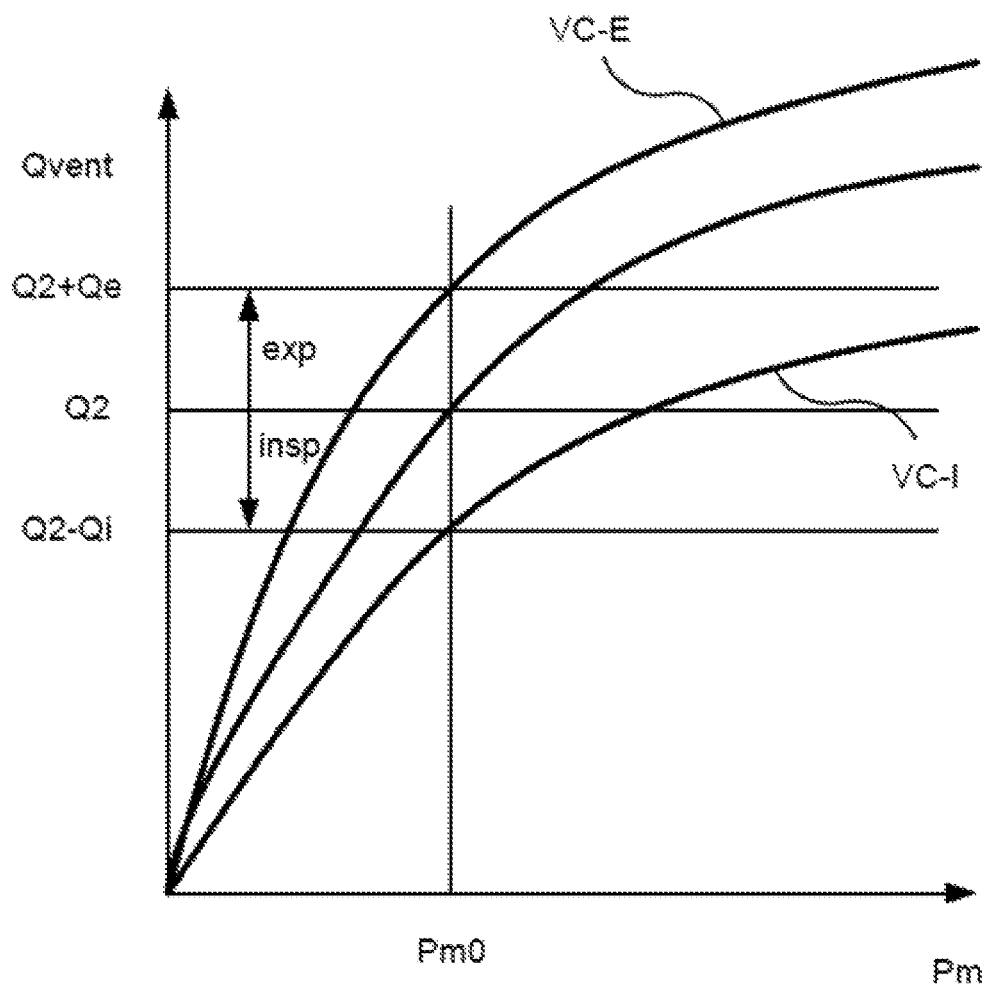
Figure 32:
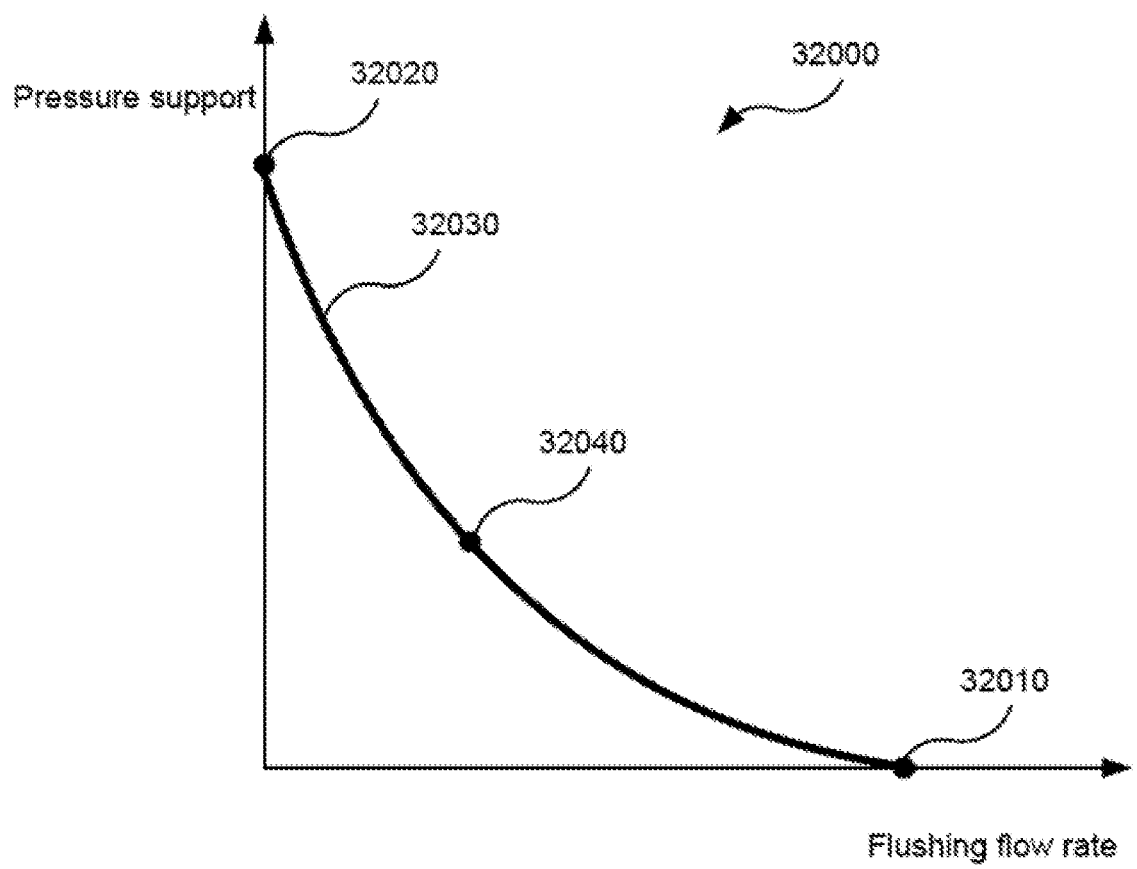
Figure 33:
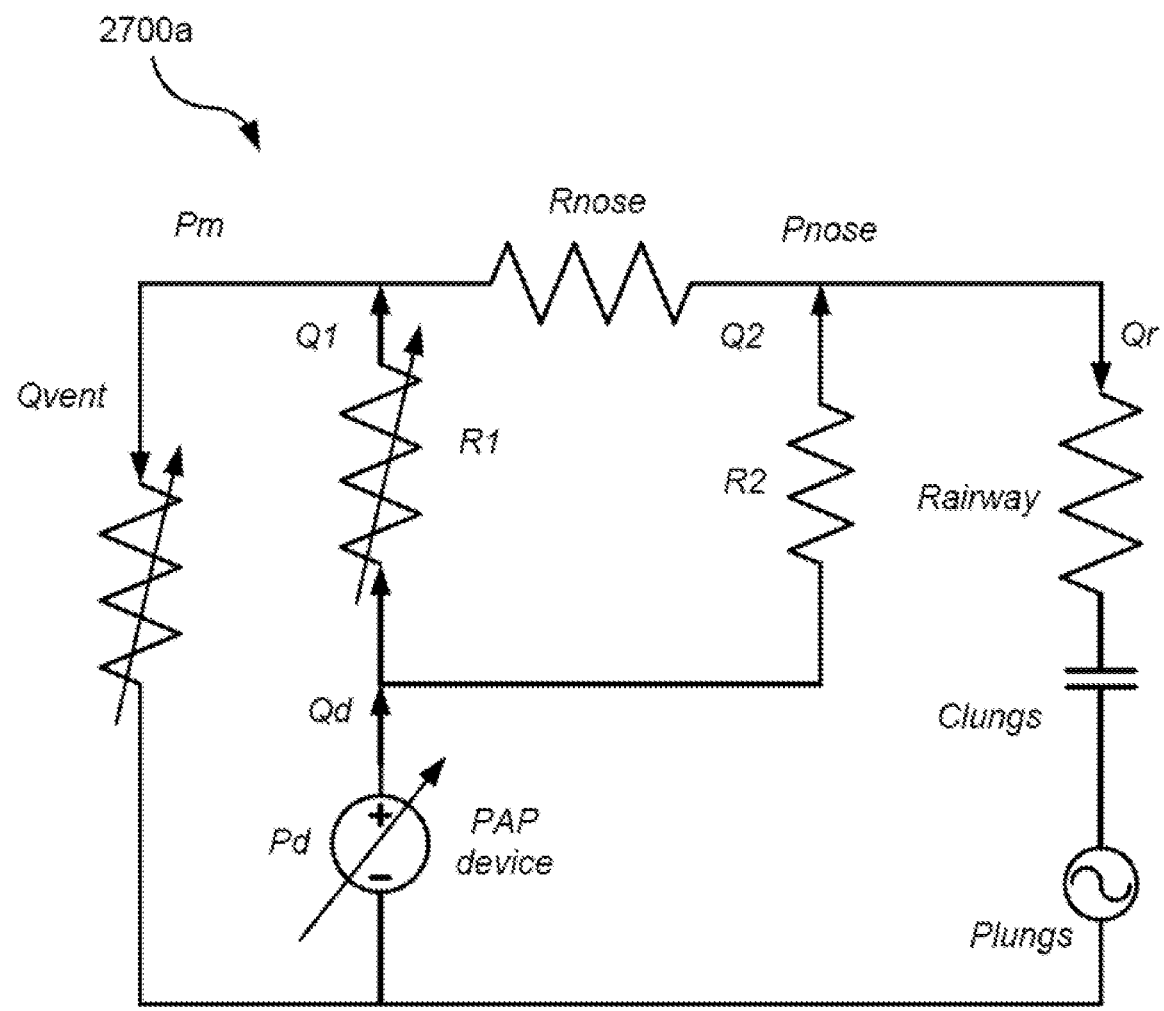

FIG. 26 is an example schematic diagram of a combination therapy system in accordance with some versions of the present technology;

FIG. 27 shows an electrical circuit model representing the flow of air in a combination therapy system in accordance with some versions of the present technology;

FIG. 28 is another example schematic diagram of a combination therapy system in accordance with some versions of the present technology;

FIG. 29 is an example control methodology diagram for a combination therapy in accordance with some versions of the present technology;

FIG. 30 is a graph illustrating the relationship between interface pressure and vent flow in one implementation of the present technology;

FIG. 31 is a graph illustrating the relationship between interface pressure and vent flow in one implementation of the present technology;

FIG. 32 is a graph illustrating the additive or complementary nature of combination therapy according to the present technology; and FIG. 33 shows an electrical circuit model representing the flow of air in a combination therapy system in accordance with another implementation of the present technology.

7 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

7.1 Therapy

In one form, the present technology comprises a control method for treating a respiratory disorder comprising controlling positive pressure to the entrance of the airways of a patient 1000 so as to provide pressure therapy as well as controlling the flow rate of air to the patient, so as to provide deadspace therapy, so as to allow for anatomical and/or apparatus deadspace flushing.

7.2 Treatment Systems

In one form, the present technology comprises an apparatus for treating a respiratory disorder. The apparatus may comprise a CT device 4000 for supplying pressurised air to the patient 1000 via an air circuit 4170 to a patient interface 3000.

7.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, a decoupling structure 3500, a connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

An alternative non-invasive patient interface is an oronasal interface (full-face mask) that seals around both the nose and the mouth of the patient 1000.

7.4 Combination Therapy (CT) Device

An example CT device 4000 in accordance with one aspect of the present technology may comprise mechanical and pneumatic components 4100, electrical components 4200 and may be programmed to execute one or more therapy algorithms. The CT device preferably has an external housing 4010, preferably formed in two parts, an upper portion 4012 and a lower portion 4014. Furthermore, the external housing 4010 may include one or more panel(s) 4015. Preferably the CT device 4000 comprises a chassis 4016 that supports one or more internal components of the CT device 4000. In one form one, or a plurality of, pneumatic block(s) 4020 (e.g., two) is supported by, or formed as part of the chassis 4016. The CT device 4000 may include a handle 4018.

The CT device 4000 may have one or more pneumatic paths depending on the types of patient interface coupled with the device. A pneumatic path of the CT device 4000 may comprise an inlet air filter 4112, an inlet muffler 4122, a pressure device 4140 capable of supplying air at positive pressure (such as a blower 4142) and a flow device 4141 capable of supplying air at a desired or target flow rate (e.g., a blower or oxygen supply line etc.), one or more pneumatic blocks 4020 and an outlet muffler 4124. One or more transducers 4270, such as pressure sensors or pressure transducers 4274 and flow rate sensors or flow transducers 4272 may be included in the pneumatic path(s). Each pneumatic block 4020 may comprise a portion of the pneumatic path that is located within the external housing 4010 and may house either pressure device 4140 or flow device 4141.

The CT device 4000 may have an electrical power supply 4210, one or more input devices 4220, a central controller 4230, a therapy device controller 4240, a pressure device 4140, flow device 4141, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the CT device 4000 may include more than one PCBA 4202.

The CT device 4000 may be configured to control provision of any of the pressure and/or flow therapies described throughout this specification.

7.4.1 CT Device Mechanical & Pneumatic Components 4100

7.4.1.1 Air Filter(s) 4110

A CT device in accordance with one form of the present technology may include an air filter 4110, or a plurality of air filters 4110 for each pneumatic path.

In one form, an inlet air filter 4112 is located at the beginning of the pneumatic path upstream of a pressure device 4140. See FIG. 4B.

In one form, an outlet air filter 4114, for example an antibacterial filter, is located between an outlet of the pneumatic block 4020 and a patient interface 3000. See FIG. 4B.

7.4.1.2 Muffler(s) 4120

In one form of the present technology, an inlet muffler 4122 is located in the pneumatic path upstream of a pressure device 4140. See FIG. 4B.

In one form of the present technology, an outlet muffler 4124 is located in the pneumatic path between the pressure device 4140 and a patient interface 3000. See FIG. 4B.

7.4.1.3 Pressure Device 4140 and Flow Device 4141

In one form of the present technology, CT device 4000 may contain two flow generators, such as a pressure device 4140 and a flow device 4141 (see FIG. 4C). Pressure device 4140 may provide a supply of air at positive pressure to a first portion of the patient interface 3000, and flow device 4141 may provide a flow of air to a second portion of patient interface 3000. Each flow generator may include a controllable blower 4142. For example the blower 4142 may include a brushless DC motor 4144 with one or more impellers housed in a volute. The blower may be preferably capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may include a blower as described in any one of the following patents or patent applications the contents of which are incorporated herein in their entirety: U.S. Pat. Nos. 7,866,944; 8,638,014; 8,636,479; and PCT patent application publication number WO 2013/020167.

The pressure device 4140 and flow device 4141 may operate under the control of the therapy device controller 4240. Alternatively, the pressure device 4140 and the flow device 4141 may operate under the control of separate controllers.

In other forms, a pressure device 4140 or flow device 4141 may be a piston-driven pump, a pressure regulator connected to a high pressure source (e.g. compressed air reservoir) or bellows.

7.4.1.4 Transducer(s) 4270

Transducers may be internal of the device, or external of the CT device. External transducers may be located for example on or form part of the air circuit, e.g. the patient interface. External transducers may be in the form of non-contact sensors such as a Doppler radar movement sensor that transmit or transfer data to the CT device.

In one form of the present technology, one or more transducers 4270 are located upstream and/or downstream of the pressure device 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

7.4.1.4.1 Flow Transducer 4272

A flow transducer 4272 in accordance with the present technology may be based on a differential pressure transducer, for example, an SDP600 Series differential pressure transducer from SENSIRION.

In use, a signal representing a flow rate from the flow transducer 4272 is received by the central controller 4230.

7.4.1.4.2 Pressure Transducer 4274

A pressure transducer 4274 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4274, is received by the central controller 4230.

7.4.1.4.3 Motor Speed Transducer 4276

In one form of the present technology a motor speed transducer 4276 is used to determine a rotational velocity of the motor 4144 and/or the blower 4142. A motor speed signal from the motor speed transducer 4276 is preferably provided to the therapy device controller 4240. The motor speed transducer 4276 may, for example, be a speed sensor, such as a Hall effect sensor.

7.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

7.4.1.6 Air Circuit 4170

An air circuit 4170 in accordance with an aspect of the present technology is a conduit or a tube constructed and arranged in use to allow a flow of air to travel between two components such as the pneumatic block 4020 and the patient interface 3000.

In particular, the air circuit may be in fluid connection with the outlet of the pneumatic block and the patient interface. The air circuit may be referred to as air delivery tube. In some cases there may be separate limbs of the circuit for inhalation and exhalation and/or for multiple patient interfaces. In other cases a single limb is used.

7.4.1.7 Oxygen Delivery 4180

In one form of the present technology, supplemental oxygen 4180 is delivered to one or more points in the pneumatic path, such as upstream of the pneumatic block 4020, to the air circuit 4170 and/or to the patient interface 3000, such as via the nasal projections or prongs of a cannula.

7.4.2 CT Device Electrical Components 4200

7.4.2.1 Power Supply 4210

A power supply 4210 may be located internal or external of the external housing 4010 of the CT device 4000.

In one form of the present technology power supply 4210 provides electrical power to the CT device 4000 only. In another form of the present technology, power supply 4210 provides electrical power to both CT device 4000 and humidifier 5000.

7.4.2.2 Input Devices 4220

In one form of the present technology, a CT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

7.4.2.3 Central Controller 4230

In one form of the present technology, the central controller 4230 is one or a plurality of processors suitable to control a CT device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein such as the one or more algorithms. In some cases, the central controller 4230 may be integrated with a CT device 4000. However, in some forms of the present technology the central controller 4230 may be implemented discretely from the flow generation components of the CT device 4000, such as for purpose of performing any of the methodologies described herein without directly controlling delivery of a respiratory treatment. For example, the central controller 4230 may perform any of the methodologies described herein for purposes of determining control settings for a ventilator or other respiratory related events by analysis of stored data such as from any of the sensors described herein.

7.4.2.4 Clock 4232

Preferably CT device 4000 includes a clock 4232 that is connected to the central controller 4230.

7.4.2.5 Therapy Device Controller 4240

In one form of the present technology, therapy device controller 4240 is a pressure control module 4330 that forms part of the algorithms executed by the central controller 4230. The therapy device controller 4240 may be a flow control module that forms part of the algorithms executed by the central controller 4230. In some examples it may be both a pressure control and flow control module.

In one form of the present technology, therapy device controller 4240 may be one or more dedicated motor control integrated circuits. For example, in one form a MC33035 brushless DC motor controller, manufactured by ONSEMI is used.

7.4.2.6 Protection Circuits 4250

Preferably a CT device 4000 in accordance with the present technology comprises one or more protection circuits 4250.

The one or more protection circuits 4250 in accordance with the present technology may comprise an electrical protection circuit, a temperature and/or pressure safety circuit.

7.4.2.7 Memory 4260

In accordance with one form of the present technology the CT device 4000 includes memory 4260, preferably non-volatile memory. In some forms, memory 4260 may include battery powered static RAM. In some forms, memory 4260 may include volatile RAM.

Preferably memory 4260 is located on the PCBA 4202. Memory 4260 may be in the form of EEPROM, or NAND flash.

Additionally or alternatively, CT device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms.

7.4.2.8 Data communication systems 4280

In one preferred form of the present technology, a data communication interface 4280 is provided, and is connected to the central controller 4230. Data communication interface 4280 is preferably connectable to remote external communication network 4282 and/or a local external communication network 4284. Preferably remote external communication network 4282 is connectable to remote external device 4286. Preferably local external communication network 4284 is connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

7.4.2.9 Output devices including optional display, alarms

An output device 4290 in accordance with the present technology may take the form of one or more of a visual, audio and haptic unit. A visual display may be a Liquid Crystal Display (LCD) or Light Emitting Diode (LED) display.

7.4.2.9.1 Display driver 4292

A display driver 4292 receives as an input the characters, symbols, or images intended for display on the display 4294, and converts them to commands that cause the display 4294 to display those characters, symbols, or images.

7.4.2.9.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

7.5 Humidifier

In one form of the present technology there is provided a humidifier 5000 as shown in FIG. 5 to change the absolute humidity of air for delivery to a patient relative to ambient air. Typically, the humidifier 5000 is used to increase the absolute humidity and increase the temperature of the flow of air relative to ambient air before delivery to the patient's airways.

7.6 Combination Therapy Applications

As previously described, the patient interface 3000 and CT device 4000 permit an application of various positive airway pressure (PAP) therapies, such as CPAP or bi-level PAP therapy or ventilation, or any other pressure therapy mentioned in this specification. In addition, the disclosed system may provide flow therapies, including deadspace therapies, such as high flow therapy ("RFT"). In HFT, air may be delivered to the nasal passages at a high flow rate, such as in the range of about 10 to about 35 litres/minute. A combination of these therapies may be provided to the patient using the disclosed technology, such as through providing a patient with a combination of pressure therapy (e.g., CPAP) and deadspace therapy (e.g., HFT). The combined flow and pressure therapies may be supplied by a common apparatus, such as CT device 4000, or by separate apparatuses. In addition, changes in a patient's therapy may be applied with no or minimal changes to the configuration of patient interface on the patient.

For example, the CT device 4000 previously described may be coupled via a delivery conduit (air circuit 4170) to the full-face mask 8008 (see e.g., FIG. 7) or via a delivery conduit (air circuit 4170) to the base portion 16016 of the patient interface 16002 (see FIG. 15A), so as to control pressure delivered to the mask or the chamber of each naris pillow. In this way, a pressure therapy can be controlled by a pressure control loop of a controller 4230 of the CT device 4000 so as to control a measure of interface pressure to meet a predetermined target pressure. The measure of interface pressure may be determined for example by a pressure sensor. Such target pressures may be modified over time, such as in synchrony with detected patient's respiration (e.g., Bi-level therapy or Pressure Support) or expected patient respiration (timed backup breath). The seal of the mask or the naris pillows will permit the pressure to be controlled at the entrance to the patient's respiratory system.

In addition to the delivery of a controlled pressure to patient interface 3000, a controlled flow of air may also be provided to the patient via patient interface 3000. For example, supplemental oxygen may be supplied by the one or more prongs 7004a, 7004b of the nasal cannula of FIGS. 6 and 7, or one or more of the nasal projections 16100 of FIG. 15 or 17. By way of further example, HFT may be supplied to the one or more prongs 9004a, 9004b of the nasal cannula of, for example, FIG. 6, 7 or 8, or the nasal projections 16100 of the patient interface of FIG. 15 or 17 such as by a flow generator configured to provide HFT. In such a case, an additional flow generator or oxygen flow source may be coupled by a projection conduit 17170 to the nasal projection or may be coupled by one or more lumens 9012 to the prongs 9004. Optionally, the flow of gas to the prongs or nasal projections may be controlled by a flow control loop of a controller. For example, the flow can be controlled by a flow control loop of a controller of the flow generator or supplemental gas source so as to control a measure of flow rate of air to meet a predetermined target flow rate. The measure of flow rate may be determined for example by a flow rate sensor. The prongs of the cannula and/or nasal projections can permit a supply of air, such as at high flow rates, within the patient's nasal passages.

In an alternative implementation, the controlled flow of air may be delivered to the mouth via an oral interface such as that described in PCT Publication no. WO 2013/163685, the entire contents of which are herein incorporated by reference. The oral interface may be positioned within a full-face mask such as the mask 8008, or beneath a nasal mask such as the mask 3000.

FIG. 26 illustrates a block diagram of an example CT device 4000 by which a controlled pressure and flow rate of air may be provided to a patient via patient interface 3000. As described above in connection with FIG. 4C, pressure device 4140 may be controlled by therapy device controller 4240. The pressurized air from pressure device 4140 may be transmitted to patient interface 3000 via one or more pneumatic paths, such as air circuit 4170, which connects with patient interface 3000 at connection port 3600. A pressure sensor 4274 may be configured to measure the pressure of the air associated with the air circuit 4170. A flow rate sensor (not shown) may be configured to measure the flow rate of the air through air circuit 4170. In addition to pressure device 4140, flow device 4141 may provide a flow of air to patient interface 3000 via one or more pneumatic paths, such as projection conduit 17170. Projection conduit 17170 may connect to patient interface 3000 at one or more secondary ports 19100. A flow rate sensor 4272 may be configured to measure the flow rate of the air through projection conduit 17170. As set forth above, flow device 4141 may also be controlled by therapy device controller 4240. Patient interface 3000 may also include a vent 3400 to allow air to flow out of patient interface 3000 to atmosphere.

The flow rate of air that is provided to the patient at patient interface 3000 will depend on the characteristics of vent 3400, which may be adjustable, as well as the pressure at patient interface 3000. For example, the flow rate of air out of vent 3400 may correspond with the pressure at patient interface 3000. This correspondence may be quadratic in nature, in which the square of the flow rate out of vent 3400 may approximately correspond to the air pressure in patient interface 3000. Accordingly, the flow rate measured at flow rate sensor 4272 will correspond to both the flow of air into the patient's airways as well as the flow of air through vent 3400. In addition, the flow rate may also vary based on the configuration of other components, such as the configuration of projection conduit 17170. Accordingly, in order to provide the patient with a desired flow rate, therapy device controller 4240 may calculate what the flow rate to the patient will be based on the parameters of the system's various components. For example, therapy device controller 4240 may access data from pressure sensor 4274 so as to calculate the flow rate out of vent 3400. Therapy device controller 4240 may then compensate the flow rate measured at flow rate sensor 4272 by the calculated flow rate out of vent 3400, so as to determine the effective flow rate of air being provided to the patient. In addition, by controlling both the pressure and the flow rate of air into patient interface 3000, CT device 4000 may control the deadspace flushing flow rate out of vent 3400.

In controlling the output of pressure device 4140 and flow device 4141, therapy device controller 4240 may simultaneously control the pressure and the flow rate of the air being provided to the patient via patient interface 3000. In this way, the disclosed system may provide the patient with a combination of respiratory therapies. For example, therapy device controller 4240 may control pressure device 4140 and flow device 4141 so that a patient is provided with CPAP therapy by having a constant pressure at patient interface 3000, while also providing HFT at a constant flow rate via projection conduit 17170. Therapy device controller 4240 may be configured so that the pressure and flow rate of air are considered to be constant if the measured pressure and the measured flow rate each remain within some predetermined threshold range.

In addition, therapy device controller 4240 may vary the pressure and/or the flow rate of the air in accordance with a predetermined therapy. For example, the pressure device 4140 and flow device 4141 may be controlled so as to provide a bi-level pressure therapy or a CPAP therapy with expiratory pressure relief in which the pressure of the air at patient interface 3000 increases during a first period of time corresponding to the patient's inspiration and decreases during a second period of time corresponding to the patient's expiration. During these periods of time the flow rate of the air may also be controlled so that the flow rate varies by some predetermined amount in correspondence with the patient's inspiration and expiration. In another example, the flow rate of the air may be held constant while the pressure at patient interface 3000 is varied.

Alternatively, the pressure may be held constant (e.g., CPAP), while the flow rate is varied. Pressure device 4140 and flow device 4141 may also be simultaneously controlled so that the pressure and flow rate of the air are both continuously varying over some period of time in accordance with a therapy that calls for some predetermined, but varying, pressure and flow rate.

In another example, pressure device 4140 and flow device 4141 may also be simultaneously controlled so as to provide for auto-titrating CPAP therapy (e.g., APAP) along with HFT. For example, a treatment pressure may be increased upon detection of one or more Sleep Disordered Breathing events. The flow rate of the HFT may be maintained relatively constant or similarly adjusted based on such detections. Accordingly, a deadspace therapy that would be otherwise compromised by OSA can be made more effective through a pressure therapy, such as APAP, that opens the patient's upper airways.

In yet another example, pressure device 4140 and flow device 4141 may be controlled in a manner that allows for the patient to reach some target amount of ventilation, such as by controlling pressure to provide pressure support therapy. For example, the pressure device 4140 of the disclosed CT system may implement adaptive servo-ventilation (ASV) therapy in combination with the high flow therapies described herein. Thus, the pressure may oscillate synchronously with patient's breathing cycle or with timed machine generated breaths to enforce a target ventilation. Similarly, the flow rate may be controlled to remain constant or it may be controlled to vary such as as a function of the patient's detected breathing cycle or as a function of the target ventilation.

By combining pressure and flow therapies, the disclosed system may provide the patient with a more effective overall therapy. For example, the effectiveness of an HFT therapy is diminished if the upper airway of the patient is closed. The patient's airway may be opened through the use of various pressure therapies, such as a PAP treatment pressure (e.g., APAP or CPAP). Therefore, HFT therapy may be made to be more effective by being combined with a pressure therapy.

Pressure support or ventilation therapy reduces the work required from the patient for breathing by providing mechanical pressure support and may allow for greater recovery of alveolar deadspace, as airways to the lungs are opened by the pressure support. Flow therapy, such as HFT, also reduces the work of breathing and allows for greater recovery of anatomical deadspace by flushing carbon dioxide rich areas of the patient's airways with air. A combination of pressure therapy and flow therapy may also assist a patient in achieving sufficient positive end-expiratory pressure (PEEP). In this way, a combination of a flow therapy and a pressure therapy may allow a patient who experiences insufficient minute ventilation or alveolar ventilation to receive a greater volume of gas exchange within the patient's lungs through the removal of anatomical and alveolar deadspace and the increase in tidal volume that is being provided to the patient's lungs. In addition, simultaneous HFT may also allow pressure support therapy to be administered at a lower level of pressure support, thereby improving the acceptability of the pressure support therapy. For example, excessive levels of pressure support can induce lung injury. As another example, using pressure support to force air through bronchitis lung produces high flow velocity in the bronchial flow paths, which can cause discomfort and even further inflammation. As another example, pressure support therapy results in a cyclic acoustic noise pattern whose volume increases with the level of pressure support.

Accordingly, a combination of one or more pressure therapies with one or more flow therapies, as described herein, may be additive or complementary. For example, FIG. 32 contains a graph 32000 illustrating the possible effects of combination therapy on a hypercapnic patient (one with elevated $PCO_2$). The horizontal axis represents the flushing flow rate of the combination therapy and the vertical axis represents a pressure support of a combination therapy in which the pressure therapy is a bi-level therapy. The point 32010 represents a therapy in which the pressure support is zero but the flushing flow rate is high, e.g. 100 litres per minute. In such a case, the therapy can be considered as essentially just a deadspace therapy. The point 32020 represents a therapy in which the pressure support is high, e.g. 20 $cmH_2O$, but the flushing flow rate is zero. In such a case, the therapy can be considered as essentially just a pressure support therapy. The points 32010 and 32020 represent forms of therapy which are equally effective by some measure, e.g. reducing the $PCO_2$ by 15%. Both however are "extreme" forms, i.e. involve high flushing flow rate and zero pressure support, or high pressure support and zero flushing flow rate respectively. All points along the curve 32030 may represent combination therapies that are as effective as the extreme therapies represented by the points 32010 and 32020, but are more moderate in both pressure support and flushing flow rate than either of those extreme therapies. The present technology allows any point on the curve 32030, e.g. the point 32040, representing a combination therapy with moderate pressure support and flushing flow rate, to be chosen for a patient depending on the preferences and characteristics of the patient, without altering the effectiveness of the combination therapy. The curve 32030 may be referred to as a curve of equal efficacy. In essence, the combination therapy may have a synergistic effect depending on settings that can provide treatment as effective as either one of the individual therapies but at reduced levels so as to unexpectedly reduce the potential for negative consequences that may be associated with higher levels of each individual therapy.

Accordingly, in some versions, controller(s) of apparatus for generating such combination therapy may be configured with such a curve (e.g., data values or a programmed function in a memory representing such a curve) to regulate a synergistic control of the therapies. For example, if a condition is detected by the controller, a change in the combination therapy may be made by automatically varying the setting of each control parameter (e.g., target pressure and target flow rate) so that they are restricted to the curve. By way of further example, if a change is made to the setting of a control parameter for one therapy (either automatically or manually), the control parameter for the other therapy may be set or recommended by the controller according to such a curve to complement the change to the first control parameter. Thus, the controller(s) may be configured to vary a target pressure and/or a target flow rate so as to restrict them to a predetermined curve of equal efficacy.

In accordance with the presently disclosed technology, the combination of a pressure therapy and a flow therapy may take a number of different forms. For example, a constant pressure (e.g., CPAP) may be used in combination with either a variable or a constant flow rate. In another example, the pressure therapy may provide a semi-fixed pressure that is adjusted in accordance with a patient's detected breathing events (e.g., obstructive apnea, hypopnea, etc.). In particular, the pressure therapy (e.g. APAP) may be provided in accordance with an AutoSet™ pressure that is automatically set by the pressure controller to a minimum pressure needed to keep the patient's airways open. In yet another example, a variable pressure therapy (e.g., Expiratory Pressure Relief (EPR) or bi-level pressure, or servo-ventilation bi-level (pressure support) modes such as ASV, ASV Auto or iVAPS) may be used in combination with a fixed or a variable flow rate. A variable pressure and variable flow rate may vary based on characteristics of the patient's breathing, thereby facilitating the breathing process.

The control of the flow of air between CT device 4000 and the patient may be modelled as an electrical circuit 2700, as shown in FIG. 27. The positive airway pressure (PAP) device shown may be pressure device 4140 described above, while the deadspace therapy (DST) device may be flow device 4141. The PAP device and the DST device may be incorporated into a single housing such as the housing 4010 of a CT device 4000, or may exist as separate units.

As shown in FIG. 27, air flows from the output of the PAP device at a flow rate Q1, and air flows from the output of the DST device at a flow rate Q2. The resistance R1 represents the resistance of air flow that may exist in the pneumatic path from the output of the PAP device to the plenum chamber 3200 of the patient interface 3000. For example, R1 may include the resistance of air flow along air circuit 4170. The resistance R2 represents the resistance of air flow that may exist in the pneumatic path from the output of the DST device to the end of the prongs or projections. For example, R2 may include the resistance of air flow along projection conduit 17170. The resistance Rnose represents the resistance of air flow from the end of the prongs or projections within the patient's nose back out the nares to the plenum chamber 3200 of the patient interface 3000. The flow whose flow rate is represented by Q2 is a flushing flow for both anatomical and mechanical deadspace (i.e. deadspace due to the patient interface), so Q2 is referred to as the flushing flow rate.

The pressure of the air at the output of the PAP device is represented as Pd. The pressure of the air at the end of the prongs or projections within the patient's nose is represented as Pnose. The pressure Pm represents the air pressure within the plenum chamber 3200 of the patient interface 3000. Air may flow out of the patient interface 3000 through a fixed or adjustable vent, such as vent 3400. The flow rate through the vent is represented as Qvent. The vent flow rate Qvent may correspond to the interface pressure Pm. Accordingly, Qvent may be represented as a function of Pm through the notation Qvent(Pm). The flow rate of air to the patient (the respiratory flow rate) is represented by Qr, with the resistance of air flow through the patient's airways being represented by Rairway. Air will flow in and out of the patient's lungs serving as an alternating pressure source during the patient's breathing cycle. Plungs is therefore shown as an alternating pressure source, with Clungs representing the elastic response of the patient's lungs to the air flow being provided at the patient interface.

From the topology of the model 2700, it may be shown that the sum of the PAP and DST flow rates Q1 and Q2 is equal to the sum of the respiratory flow rate Qr and the vent flow rate Qvent:

$$Q1+Q2=Qvent(Pm)+Qr$$

Because the average respiratory flow rate Qr over many breathing cycles is zero, the average or DC component of the vent flow rate Qvent, which may be referred to as the "bias flow rate", is the sum of the average or DC components of Q1 and Q2.

The PAP and DST devices of the model 2700 may be controlled so as to manage both the pressure and flow rate of air in the system, which may be achieved by control changes of the flow generators of the PAP and/or DST devices, and optionally in conjunction with controlling mechanical variations of the opening size of the vent. In general, the interface pressure Pm and the deadspace flushing flow rate Q2 may be controlled independently by respective control of the PAP and DST devices. In particular, the PAP device may maintain a given interface pressure Pm by setting its own output pressure Pd to compensate for the known pressure drop through the resistance R1 at any given flow rate Q1. However, in order to maintain this control it is beneficial to maintain a positive flow rate Q1 from the PAP device, to ensure the device pressure Pd is greater than the interface pressure Pm. To keep Q1 positive, the flushing flow rate Q2 may be controlled so that throughout the patient's breathing cycle the following is true:

$$Q2<Qvent(Pm)+Qr$$

During expiration, the respiratory flow rate Qr is negative, so by controlling Q2 to be less than Qvent minus the peak expiratory flow rate Qe(peak), Q1 may be kept positive throughout the breathing cycle. In other words, the maximum flushing flow rate Q2(max) is Qvent(Pm)−Qe(peak). Since in general a lower pressure Pm means a lower vent flow rate Qvent, a lower pressure Pm means a lower ceiling on the flushing flow rate Q2. As long as the flushing flow rate is less than Q2(max), the positive flow Q1 from the PAP device makes up the difference between Q2 and Qvent+Qr. Q1 therefore oscillates around a steady state value of Qvent−Q2 in synchrony with the breathing cycle, rising during inspiration and falling during expiration.

In this way, the desired flushing of deadspace, such as the flushing of carbon dioxide from the patient's anatomical deadspace, may be accomplished through control of the vent pressure / flow characteristic. For example, for a given interface pressure Pm, an adjustment to the vent to allow a higher vent flow rate Qvent(Pm) allows a higher deadspace flushing flow rate Q2.

The vent flow rate, Qvent, may approximate a quadratic relationship with the patient interface pressure Pm, such that:

$$Pm=(A*Qvent^2)+(B*Qvent)$$

The terms "A" and "B" are values that may be based on one or more parameters of the vent. These parameters may be adjusted so as to alter the relationship between Qvent and Pm such as when the opening size of an active proximal valve (APV) serving as the vent 3400 is controlled to change. An example APV is disclosed in PCT Publication no. WO 2010/141983, the entire disclosure of which is incorporated herein by reference.

For example, in some cases, changing treatment may require changing of venting characteristics associated with the patient interface. Thus, in some cases, such as when a pressure therapy is being provided with the naris pillows and a CT device, it may thereafter become desirable to initiate a flow therapy with the nasal projections, such as providing a flow of supplemental oxygen or high flow therapy. This change in treatment, which may be processor activated in the case of a common apparatus or manually initiated such as in the case of multiple supply devices, may require an adjustment to a venting characteristic of the patient interface. For example, a manual vent may be opened or opened more so as to compensate for the increased flow of gas to the patient's nares. Alternatively, in the case of an adjustable vent, a processor may control opening of the vent or opening it more upon activation of the additional flow to the nasal projections. Similar vent control may be initiated upon application of a mask over a cannula such as in the illustration of FIGS. 7, 10, 12 and 13. In the case of termination of such an additional therapy, the venting characteristics may be changed again, such as by manually closing or reducing a vent size or by controlling with a controller a closing or reduction in the vent size of an automatic/electromechanical vent (e.g., an active proximal valve).

The therapy device controller 4240 may control the device pressure Pd of the pressure device 4140 to deliver a desired or target interface pressure Pm such as for controlling a generally constant (with respect to breathing cycle) pressure therapy, without needing to know the flushing flow rate Q2 being delivered by the flow device 4141. In such a case, the therapy device controller 4240 may use conventional methods of leak estimation and compensation. Under such an approach, the therapy device controller 4240 may effectively treat the flushing flow as a large, constant, negative leak flow that may be estimated and compensated for such as when estimating patient flow and/or adjusting pressure to counter undesired pressure swings induced by patient respiration. Similarly, to deliver a bi-level pressure therapy, the therapy device controller 4240 may control the device pressure Pd of the pressure device 4140 to synchronise the mask pressure Pm with the patient's breathing cycle without needing to know the flushing flow rate Q2. Under such an approach, the therapy device controller 4240 may use conventional leak estimation and compensation methods to estimate the respiratory flow rate Qr, effectively treating the flushing flow as a large, constant, negative leak flow. The therapy device controller may then apply conventional triggering and cycling processing to the respiratory flow rate Qr to determine when to switch the desired interface pressure Pm from inspiration to expiration and back.

However, it may be advantageous for the therapy device controller 4240 to account explicitly for the flushing flow rate Q2 for either or both of controlling the interface pressure Pm and estimating the respiratory flow rate Qr for triggering and cycling purposes.

Likewise, it may be advantageous for the therapy device controller 4240 to use the sensed device pressure Pd from the pressure sensor 4274 in order to compute the interface pressure Pm and hence the maximum flushing flow rate Q2 (max), namely Qvent(Pm)-Qe(peak), to ensure the flushing flow rate does not exceed this upper limit.

In implementations in which the pressure device 4140 and the flow device 4141 are under the control of a common therapy device controller 4240, as in FIG. 26, the controller 4240 is aware of all the system variables such as the device pressure Pd and the flushing flow rate Q2 (such as with sensed values for the variables), and can therefore control the pressure device 4140, the flow device 4141, and optionally an adjustable vent 3400 to deliver a desired interface pressure Pm and flushing flow rate Q2 in accordance with the above description.

However, in implementations in which the pressure device 4140 and the flow device 4141 are under the control of separate controllers, the pressure device controller may obtain the flushing flow rate Q2, either by direct communication with the flow rate transducer 4272, or through communication with the flow device controller. Likewise, the flow device controller may obtain the device pressure Pd either by direct communication with the pressure transducer 4274, or through communication with the pressure device controller.

7.6.1 Single Flow Generator Examples

In some implementations, a single flow generator may be used to supply both the flushing flow rate of gas through one or more of the nasal projections or prongs and the air pressure within the patient interface 3000. In one such implementation, the air circuit 4170 is not used, the connection port 3600 is blocked, and projection conduit 17170 may be connected to the output of a single blower 4142, as shown in FIG. 28. In such an implementation, which may be modelled by the circuit model 2700 without the PAP device or the resistance R1, the flow rate Q1 is identically zero, so for any given venting characteristic Qvent(Pm), the vent flow rate Qvent will oscillate in synchrony with the breathing cycle around the flushing flow rate Q2, rising to Q2+Qe at peak expiration, and falling to Q2−Qi at peak inspiration, as illustrated in FIG. 30. The interface pressure Pm will also oscillate along the venting characteristic around a steady state pressure Pm0 such that Qvent(Pm0) equals the flushing flow rate Q2, falling during inspiration to a trough pressure Pmi and rising during expiration to a peak pressure Pme. Such oscillation in interface pressure may not be desirable and may be minimised by adjusting the venting characteristic in synchrony with the patient's breathing cycle. For example, as illustrated in FIG. 31, to maintain a constant interface pressure Pm0 at a given flushing flow rate Q2, the parameters of the venting characteristic may be continually adjusted in synchrony with the patient's breathing cycle so that the venting characteristic follows the curve VC-E during expiration, causing Qvent(Pm0) to rise to Q2+Qe and follows the curve VC-I during inspiration, causing Qvent(Pm0) to fall to Q2−Qi.

Similar continuous adjustments to the venting characteristic may also be made to maintain a constant interface pressure Pm throughout the breathing cycle in an implementation with no DST device, so that Q2 is identically zero. In such an implementation, for any given PAP device pressure Pd, resistance R1, venting characteristic Qvent(Pm), and respiratory flow rate Qr, the interface pressure Pm satisfies the equation $$\frac{Pd - Pm}{R1} = Qvent(Pm) + Qr$$

Continual adjustments to the venting characteristic, or to the device pressure Pd, in synchrony with the breathing cycle allow Pm to be maintained at its steady state value (i.e. its value when Qr is zero) as Qr varies over the breathing cycle.

Accordingly, in such single-flow-generator implementations, the interface pressure Pm and flushing flow rate Q2 may be simultaneously and independently controlled by varying one or more parameters of the vent 3400 so that a predetermined pressure and predetermined flushing flow rate are maintained at patient interface 3000 throughout the breathing cycle. Further, this configuration allows for control of both Pm and Q2 to arbitrary patterns with respect to time and the patient's respiration. For example, a bi-level pressure waveform for Pm where the inspiratory pressure is higher than the expiratory pressure while Q2 is also controlled to vary based on aspects of the patient's breathing. Other examples include Pm of pressure therapy modes of CPAP, APAP, APAP with EPR, ASV, ST, and iVAPS combined with a Q2 of flow therapy modes such as fixed flow rate, flow rate varying on the patient's state of inspiration or expiration, or other ventilation parameters such as relative hyperventilation or hypoventilation with respect to the ventilation mean.

In another single flow generator implementation in which there is no separate DST device, the output of the PAP device is connected to both the air circuit 4170 and the projection conduit 17170. Such an implementation may be modelled by the electrical circuit model 2700a illustrated in FIG. 33. Independent control of the interface pressure Pm and the flushing flow rate Q2 to their respective target values throughout the breathing cycle may be enabled by adjusting the vent characteristic in synchrony with the breathing cycle as described above. Alternatively, or additionally, independent control of the interface pressure Pm and the flushing flow rate Q2 to their respective target values throughout the breathing cycle may be enabled by adjusting the device pressure Pd in synchrony with the breathing cycle. Alternatively, or additionally, the resistance of the air circuit 4170 may be made variable, e.g. by adding a variable resistance (e.g., a proportional valve) in the air circuit 4170. Independent control of the interface pressure Pm and the flushing flow rate Q2 to their respective target values throughout the breathing cycle may be enabled by adjusting the resistance of the variable resistance in the air circuit 4170 in synchrony with the breathing cycle.

7.6.2 Nasal Interface Examples

Various flow path strategies may be implemented to wash out exhaled carbon dioxide given such different therapies and the different configurations of the nasal interface when controlled in conjunction with any of the aforementioned pressure control regimes. These may be considered with reference to the flow arrows F of the figures. In the example of FIG. 15A, either an inspiratory flow (i.e., cyclical supply activation) or a continuous flow may be supplied toward the patient nasal cavity via both of the nasal projections 16100 that may be inhaled by the patient during inspiration. The distal ends (DE) of the nasal projections may be coupled with further supply conduits such as that illustrated in FIG. 16. Expiratory gases may be exhausted from the patient nasal cavities into the passage of the naris pillows and out through any one or more of the optional base vent 16220 and/or pillow vent(s) 18220. The control of a continuous exhaust flow via such vents during both inspiration and expiration can assist in ensuring washout of expiratory gases from the nasal cavities.

In the example of FIG. 15B, either an inspiratory flow (i.e., cyclical supply activation) or a continuous flow is supplied toward the patient nasal cavity via one of the nasal projections 16100 that may be inhaled by the patient during inspiration. In this example, although not shown in FIG. 15B, the distal end (DE) of the nasal projection on the left of the drawing may be coupled to a further supply conduit and a gas source. This flow supply nasal projection is shown on the left side of FIG. 15B but may alternatively be on the right. Expiratory gases may then be exhausted from the patient nasal cavities via the other nasal projection 16100 (e.g., shown on the right of the figure). In this case, the distal end of one nasal projection may omit a further conduit and serve as a pillow vent at the proximity of the naris pillow 16010. The control of a continuous exhaust flow via such a vent during both inspiration and expiration can assist in ensuring washout of expiratory gases from the nasal cavities.

In the example of FIGS. 17A and 17B, the presence of dual nasal projections permits venting and supply via the nasal projections in each naris. Thus, either an inspiratory flow (i.e., cyclical supply activation) or a continuous flow is supplied toward the patient nasal cavity via one of the nasal projections 16100-2 of each naris pillow that may be inhaled by the patient during inspiration. In this example, although not shown in FIG. 17B, the distal end DE of one nasal projection of each naris pillow may be coupled to a further supply conduit and a gas source. Expiratory gases may then be exhausted from the patient nasal cavities via the other nasal projection 16100-1 of each naris. In this case, the distal end of one nasal projection of each naris may omit a further conduit and serve as a pillow vent 18220 at the proximity of the naris pillow 16010. The control of a continuous exhaust flow via such vents during both inspiration and expiration can assist in improving washout of expiratory gases (such as carbon dioxide) from the nasal cavities.

In some cases, the washout flow path may be implemented with a unitary nasal projection in each naris pillow. Such an example may be considered in relation to FIG. 18. In this example, a gas supply nasal projection is omitted. The unitary nasal projection 16100 in each naris pillow may then serve as a nasal projection vent, such as by venting as a pillow vent. Thus, either an inspiratory flow (i.e., cyclical supply activation) or a continuous flow is supplied toward the patient nasal cavity via each naris pillow so that it may be inhaled by the patient during inspiration. In this example, the distal end of the unitary nasal projection 16100 may omit a further conduit and serve as a pillow vent 18220 at the proximity of the naris pillow 16010. The control of a continuous exhaust flow via such vents during both inspiration and expiration can assist in ensuring washout of expiratory gases from the nasal cavities.

In some cases, the washout flow path may be implemented without nasal projections. Such an example may be considered in relation to the nasal pillows of FIGS. 19A and 19B. In this example, each naris pillow may have a pillow vent for venting expiratory gases during expiration (See FIG. 19B). The pillow vent may be open during inspiration and expiration or only open during expiration. Either an inspiratory flow (i.e., cyclical supply activation) or a continuous flow is supplied toward the patient nasal cavity via each naris pillow 16010 so that it may be inhaled by the patient during inspiration (See FIG. 19A). The control of a continuous exhaust flow via such vents during both inspiration and expiration can assist in ensuring washout of expiratory gases from the nasal cavities. However, in the absence of the nasal projection there is a marginal increase in the deadspace.

In the example of FIGS. 20A and 20B, vents at the neck or base of each naris pillow may be activated by an optional vent valve 21410. These naris pillows may optionally include any of the nasal projections previously described. In this version, the vent valve may be activated by rising pressure associated with the patient's expiratory cycle so as to permit cyclical venting at the patient's naris pillow. Thus, as illustrated in FIG. 20A, during expiration, expiratory gases open the vent valve to expel expiratory air to atmosphere. At this time, the flow path from the air circuit 4170 to the naris pillow may be blocked. As illustrated in FIG. 20B, during inspiration, supply gas from the flow generator or CT device may close the vent valve. At this time, the flow path from the air circuit 4170 to the naris pillow may be open.

In another example of FIGS. 20C and 20D, such valves 21410 may be configured so that only some of the pillow vents 18220 are closed at any one time. In this arrangement, the valves 21410 may be configured so that one pillow vent is opened, while the other is closed. Referring now to FIG. 20C, the pillow vent to the left of the figure is open, while the pillow vent to the right is closed, and thus expiratory flow from the patient exits through the open pillow vent. During inhalation, as shown in FIG. 20D, the flow generator or CT device delivers a flow of supply gas, which is delivered to the patient while the pillow vent to the left remains open, thereby continuously washing out gases which has the effect of reducing dead space. An alternative arrangement is shown in FIGS. 20E and 20F, wherein the pillow vent to the left is closed and the pillow vent to the right is open. In one form, the valves 21410 may be arranged so that they are switchable from a first arrangement, for example shown in FIGS. 20C and 20D to a second arrangement for example shown in FIGS. 20E and 20F. For example, in the case of an electromagnetic operation of the valves, they may be set to the desired operation by a controller. For example, they may be alternated on a predetermined or pre-set time cycle. Optionally, the valves may be manually operated and may be manually switched at a desired time.

One advantage of switching from the first to the second arrangement and thus alternating between the left and right nasal passages as described above may be that it may improve the patient's comfort level. For instance, the patient using the patient interface as shown in FIGS. 20C-20D may experience discomfort from drying out of the patient's right (left on the figure) nasal passage, which may be alleviated by changing the configuration of the patient interface to that shown in FIGS. 20E-20F.

Optionally, such a valve may be extended into a nasal projection (e.g. shown in FIG. 21) such that the nasal projection may serve as both supply and exhaust conduit. In such a case, the nasal projection may include a valve membrane 22500 that divides the conduit. The valve membrane 22550 may be flexible and extend along the nasal projection 16100 from or near the proximal end toward a vent portion 22510 of the nasal projection. The vent portion may be proximate to or serve as a pillow vent 18220. The valve membrane 22550 of the nasal projection may be responsive to inspiratory and expiratory flow such that it may move (See Arrow M of FIG. 22) dynamically across the channel of the nasal projection as illustrated in FIGS. 22, 23A and 23B. The valve membrane may then dynamically reconfigure the nasal projection as an inspiratory conduit and expiratory conduit on either side of the membrane. For example, as shown in FIG. 23A, responsive to patient expiration, movement of the valve membrane 22550 across the proximal end of the nasal projection enlarges an expiratory channel portion ECP of the projection that leads to the vent portion 22510. This movement thereby reduces an inspiratory channel portion ICP of the nasal projection that leads to a supply gas source or flow generator. Similarly, as shown in FIG. 23B, responsive to patient inspiration, return movement of the valve membrane 22550 across the proximal end of the nasal projection reduces an expiratory channel portion ECP of the projection that leads to the vent portion 22510. This movement thereby expands an inspiratory channel portion ICP of the nasal projection that leads to a supply gas source or flow generator.

Nasal interfaces such as the nasal mask 3000 or the pillows interface 16002 have an advantage over oro-nasal interfaces in that they more easily permit the patient to speak and eat while receiving combination therapy. In addition, when the patient opens his or her mouth incidentally, for example during sleep, the open mouth acts as an aperture through which leak may occur. Whether mouth opening is incidental or purposeful to speak or eat, it would be helpful for the control of combination therapy to detect such an occurrence. Mouth leak may be continuous or "valve-like", occurring intermittently when mouth pressure rises during exhalation. Both kinds of mouth leak may be detected by estimating and analysing the respiratory flow rate Qr, for example using the methods described in PCT Patent Publication no. WO 2012/012835, the entire contents of which are herein incorporated by cross-reference. If a continuous mouth leak is detected by the controller, the target interface pressure Pm may be reduced by the controller, e.g. to zero, for the duration of the mouth opening, to reduce what is often the unpleasant sensation of air rushing out the mouth and to enable the patient to eat or speak more comfortably. However, the controller may optionally continue to control delivery of the deadspace therapy throughout any of the detected mouth leak events.

In a further implementation, an intentional flow of air out the mouth may be enabled and controlled by a specially designed oral appliance to be worn by the patient during therapy, e.g. during sleep. Such a mouth flow may act as an alternative or supplementary path to ambient for the flushing flow entering the nasal cavity. The effect of the oral appliance may be modelled in the electrical circuit model 2700 of FIG. 27 by a further resistive element between the nose and ambient, i.e. in parallel with the airway path on the far right of the model 2700. The presence of this element, and the mouth flow rate Qmouth through it, effectively adds Qmouth to the ceiling Q2(max) on the flushing flow rate Q2 for any given interface pressure Pm.

7.6.3 Oro-Nasal Interface Examples

In another form, an oro-nasal (full-face) mask may comprise one more flow directors configured to deliver a flow of gas towards the nares of the user. The flow directors may be connected to, and receive the flow of gas from a supplemental gas source such as an oxygen source or a flow generator suitable for HFT. For example, the patient interface may comprise one or more secondary ports 19100 as shown in FIG. 24 connectable to the supplemental gas source such as via a supply conduit.

One example of the flow directors may be one or more tubes 19200 coupled to one or more secondary ports 19100 and located outside of a naris of a patient to direct the flow of gas as shown in FIG. 25A. The one or more tubes 19200 may be a separable component which can be engaged with the frame of the patient interface (e.g. mask) as shown in FIG. 25A, where the tubes 19200 are engaged within the plenum chamber 3200. In some forms, the one or more tubes 19200 may be integrally formed with another portion of the patient interface such as the plenum chamber 3200. The one or more tubes 19200 may be movably configured relative to the rest of the patient interface, such as pivotably coupled to the mask as shown in FIG. 25A, to be able to adjust the direction of the flow of gas.

A flow director may further comprise a locating feature to allow the flow director to remain in place once it has been adjusted, for example by frictional engagement with the plenum chamber 3200. Although the arrangement shown in FIG. 25A shows two such tubes that are fluidly connected to each other, as well as to the secondary ports 19100, it will be understood that any number of ports and tubes may be used, as well as any combination of connections therebetween, analogously with the above descriptions of nasal projections. In another example, each tube 19200 may be independently connected to the plenum chamber 3200 using hollow spherical joints (not shown) which allow a flow of gas therethrough, while also allowing movements of the tube relative to the rest of the patient interface. Such a connection may thereby allow a flow of gas to travel between a secondary port 19100 and the tube 19200.

In some cases, a flow director may be in a form of a flow directing surface 19300 coupled to a secondary port 19100. For instance, each flow directing surface shown in FIG. 25B may comprise a curved surface shaped to direct the flow of gas from the supplemental gas source using the Coanda effect, whereby the flow "attaches" or conforms to the curved surface and follows its profile. In some forms, the flow directing surface 19300 may be movably configured, for example by being rotatably coupled to the plenum chamber 3200.

According to another aspect, a flow director or a nasal projection may comprise a flow element, such as a honeycomb grid (not shown), to reduce turbulence of the flow, whereby the flow director produces a more laminar flow than otherwise. Such an arrangement may be particularly advantageous when used in conjunction with a flow director, as a laminar flow may be more focussed in comparison to a turbulent flow as it exits out of an orifice. Accordingly, use of a flow element may assist in delivering a greater proportion of the flow of gas to the naris of the patient, whereas without a flow element, more of the flow of gas may be lost to the interior of the mask and possibly washed out through a vent.

7.6.4 Example Flow/Pressure Control Methodology

FIG. 29 shows a flow diagram 2900 in accordance with an aspect of the disclosed systems and methods. Each block of flow diagram 2900 may be performed by one or more controllers of a single device, such as CT device 4000, or by controllers of multiple devices. Various blocks may be performed simultaneously or in a different order than shown. In addition, operations or blocks may be added or removed from the flow diagram and still be in accordance with aspects of the disclosed technology.

In block 2902, a controller may identify a predetermined pressure and a predetermined flow rate of the air to be provided to a patient interface. As described above, the predetermined pressure and/or the predetermined flow rate may be constant or variable for a given period of time, and may be selected based on a desired therapy or combination of therapies to be provided to the patient. For example, a bi-level pressure therapy may be selected for which the predetermined pressure of the air is to be adjusted based on the patient's inspiration and expiration, while the predetermined flow rate may be maintained at a constant level in accordance with a selected form of HFT. In block 2904, a controller may receive a measurement of the current pressure and the current flow rate, as measured by a pressure sensor and a flow rate sensor, respectively. A controller may compare the measured pressure and flow rate with the predetermined pressure and the predetermined flow rate, respectively (block 2906). The comparison may include determining whether the measured pressure and flow rate are at or within an acceptable range with respect to the predetermined pressure and the predetermined flow rate. If the measured pressure and flow rate correspond to the predetermined pressure and flow rate, the controller may return to block 2904.

If the measured pressure or flow rate does not correspond to the predetermined pressure or flow rate, the controller may adjust the output of one or more flow generators and/or may adjust one or more parameters of an adjustable vent in a manner described above (block 2908). For example, the system may include two flow generators, such as pressure device 4140 and a flow device 4141 described above. If the measured pressure does not correspond to the predetermined pressure, the controller may adjust the output of either one or both of the flow generators, so as to bring the measured pressure into correspondence with the predetermined pressure. The adjustment to the output of one or both of the flow generators may be performed so that the measured flow rate continues to correspond with the predetermined flow rate. In this way, the pressure and flow rate are simultaneously controlled. The controller may return to block 2904 until the selected therapy session is terminated or the device is no longer in use (block 2910).

7.6.5 Titration of Combination Therapy

The optimal parameters (e.g., pressure and flow rate) of combination therapy, in particular the balance between the two therapies, i.e. the position on the curve 32030, in combination therapy will vary from patient to patient. The process of choosing the therapy parameters for a patient is known as titration. In general the parameters may be chosen or varied based on the patient's condition as well as respiratory parameters such as minute ventilation, respiratory rate, expiratory flow shape, lung mechanics, deadspace, and expired $CO_2$. For example, patients with severe NMD need a predominance of pressure support to assist in the work of breathing, whereas emphysemic patients may benefit proportionally more from deadspace therapy. Patients with large lung volume with low pressure support may indicate high deadspace and therefore proportionally more benefit from deadspace therapy. Conversely, high respiratory rate indicating significant respiratory effort may benefit more from pressure support.

One form of pressure support therapy known as iVAPS is based on servo-control of alveolar ventilation by varying pressure support. In iVAPs, the target level of ventilation is an alveolar ventilation computed by subtracting anatomical deadspace ventilation from minute ventilation. The amount of anatomical deadspace for a given patient is a setting that may be provided to the servo-controller or estimated from the patient's height. In combination with deadspace therapy, a controller controlling this form of pressure support therapy may apply a lower value of anatomical deadspace than would be expected for the patient without the deadspace therapy such as by implementing a reduction value applied to the entered or computed anatomical deadspace information so that the controller can compute a target ventilation setting for alveolar ventilation that accounts for the DST. A lower value of deadspace ventilation will result in an alveolar ventilation that is closer to the minute ventilation. Hence the controller with such a calculated ventilation target will control generally lower levels of pressure support.

7.6.6 Cardiac Output Estimation

The Fick technique estimates cardiac output by estimating the response in expired $CO_2$ to a deadspace manoeuvre (typically a step change in deadspace). The flushing flow rate in deadspace therapy can be used to effectively manipulate deadspace, and a measure of ventilation (e.g., minute ventilation or tidal volume) can be used as a proxy for $CO_2$ response, particularly during sleep. Therefore, the Fick technique can be performed in combination therapy by measuring the change in ventilation (e.g., minute ventilation or tidal volume) resulting from a step change in flushing flow rate. For example, a controller may be implemented to calculate or generate a cardiac output estimate by controlling a step change in the flushing flow rate and determining change in a measure of ventilation (e.g., minute ventilation or tidal volume) in relation to the step change in accordance with the Fick technique. Such a process may be automatically initiated (or periodically) by the controller such as during a sleep session, such as when sleep has been detected by the controller. The controller may detect sleep by any known method, such as by any of the automated methods described in International Patent Application no. PCT/

AU2010/000894 (WO/2011/006199) entitled "Detection of Sleep Condition", the entire disclosure of which is incorporated herein by reference.

7.7 Additional Patient Interfaces for Optional Therapies

Some patients have a need for multiple therapies. For example, some patients may require supplemental gas therapy. For example, supplemental oxygen therapy may be delivered to the patient by use of a nasal cannula where prongs of the cannula supply the oxygen at the patient's nares. Unlike nasal CPAP, such a therapy does not typically supply the air at therapeutic pressure(s) so as to treat events of sleep disordered breathing such as obstructive apnea or obstructive hypopneas. Supplemental oxygen therapy may be considered with reference to the illustration of FIG. 6. The traditional nasal cannula 7002 includes nasal prongs 7004A, 7004B which can supply oxygen at the nares of the patient. Such nasal prongs do not generally form a seal with the inner or outer skin surface of the nares. The gas to the nasal prongs may typically be supplied by one or more gas supply lumens 7006a, 7006b that are coupled with the nasal cannula 7002. Such tubes may lead to an oxygen source. Alternatively, in some cases, such a nasal cannula 7002 may provide a high flow therapy to the nares. Such a high flow therapy (HFT) may be that described in U.S. Patent Application Publication No. 2011-0253136 filed as International Application PCT/AU09/00671 on May 28, 2009, the entire disclosure of which is incorporated herein by cross reference. In such a case, the lumen from the nasal cannula leads to a flow generator that generates the air flow for high flow therapy.

During delivery of such supplemental gas therapies with a traditional nasal cannula, it may be desirable to periodically provide a further therapy, such as a pressurized gas therapy or positive airway pressure (PAP) therapy that requires a patient interface to form a pressure seal with the patient's respiratory system. For example, during oxygen therapy with a traditional nasal cannula, it may be desirable to provide a patient with a traditional CPAP therapy when a patient goes to sleep, or traditional pressure support therapy. These additional therapies may require a mask such as a nasal mask or oro-nasal (mouth and nose) mask that may optionally include an adjustable vent. Such an example may be considered with reference to FIG. 7. When the mask 8008 is applied to the patient over the traditional nasal cannula, one or more of the components of the nasal cannula may interfere with the mask's seal forming structure (e.g., cushion 8010) so as to prevent a good seal with the patient. For example, as shown in FIG. 7, the lumens 7006a, 7006b may interfere with a cushion 8010 of the mask. This may result in a substantial cannula induced leak (CIL) at or near the lumen which may prevent the desired therapy pressure levels from being achieved in the mask. Apparatus and therapies described herein may be implemented to address such issues so as to permit simultaneous pressure and flow control.

7.7.1 Modified Nasal Cannula Embodiments

In some implementations of the present technologies, a modified nasal cannula may be implemented to permit its use with changing therapy needs. For example, as illustrated in FIG. 8, the nasal cannula 9002 includes a set of projections (e.g., one or more prongs 9004a, 9004b). Each projection or prong may extend into a naris of a user. The projection serves as a conduit to deliver a flow of gas into the naris of the user. The nasal cannula 9002 will also typically include one or more coupler extensions 9020a, 9020b. The coupler extension may serve as a conduit to conduct a flow of gas from a gas supply line, such as lumen 9012a, 9012b. The coupler extension may be removably coupleable with a base portion 9022 of the nasal cannula 9002 and/or the supply line(s) of the cannula. Alternatively, the coupler extension may be integrated with either or both.

Typically, each coupler extension(s) may be configured with a seat portion 9024a, 9024b. The seat portion may include a contact surface for another patient interface. For example, the seat portion can serve as a contact surface for a typical seal forming structure (e.g., a typical face contact cushion) of a mask so as to permit a seal there between. Thus, the contact surface of the seat portion may form a seal with a cushion of a mask. The coupler extension will also typically include a contact surface for skin/facial contact with a patient to form a seal there between. The seat portion can include a surface adapted to minimize or eliminate a cannula induced leak CIL. In some such cases, it may include a surface with a sealing bevel 9090. The sealing bevel 9090 may promote sealing between the cushion of the mask and a facial contact surface. In this way, it may fill a gap that would otherwise be induced by a traditional nasal cannula structure.

Figures 9A, 9B, 9C, 9D:
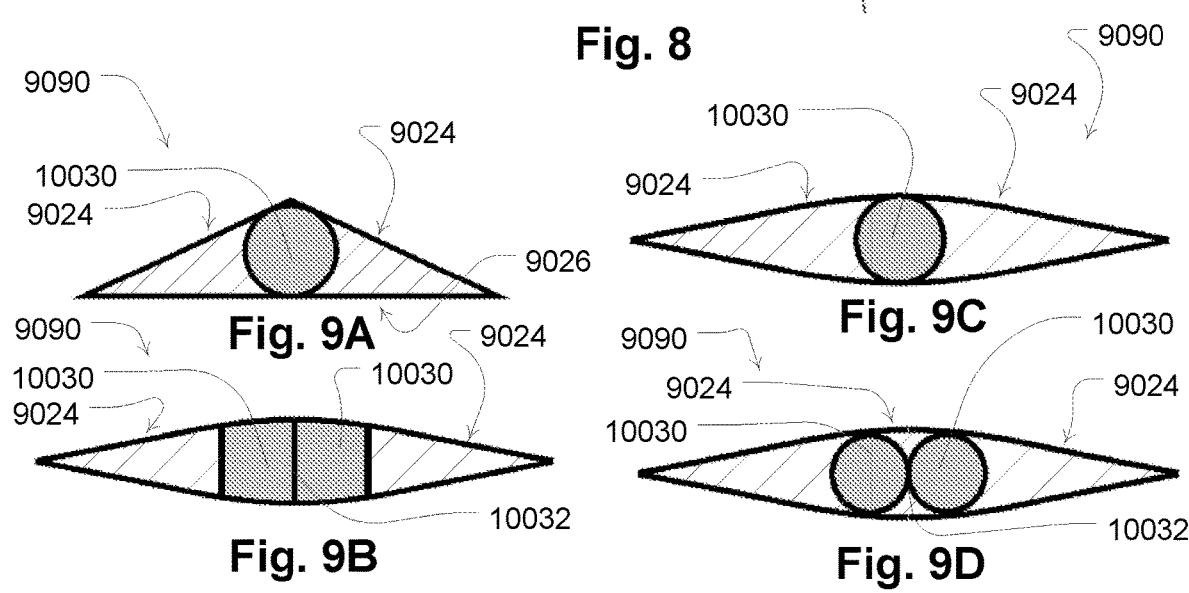

The sealing bevel of the seat portion may be formed with various cross sectional profiles to promote sealing. For example, as illustrated in FIG. 9A, the seat portion 9024 of the coupler extension may have a generally triangular cross sectional profile. It may be a triangle, for example an isosceles triangle, with the mask sealing surface on the sides opposite the base. Thus, the sides opposite the base may be equal or of different lengths. The base 9026 may typically be configured as the patient sealing surface. Other cross sectional profiles may also be implemented. For example, FIGS. 9B, 9C and 9D show a lentil cross sectional profile. Thus, as illustrated, the profile may be larger centrally and the top and bottom surfaces may gradually converge by similar slopes toward the opposing ends of the profile.

In some cases, the coupler extension(s) may serve as a conduit for conducting air between the prongs of the nasal cannula and lumen. For example, as illustrated in FIGS. 9A, 9B, 9C and 9D, the seat portion may include one or more channel conduits 10030. The channel conduits may be employed for directing gas in different gas flow directions with respect to the nasal cannula, to provide gas to different prongs and/or to provide different gases etc. For example, one channel conduit may lead to one prong of the nasal cannula and another channel conduit, if included, may lead to the other prong of the nasal cannula. As shown in FIG. 9A and 9C, a single channel conduit is provided. The single channel conduit is round and may couple with a tube shaped lumen. However, it may be other shapes, e.g., rectangular. This channel conduit may lead to both prongs or one prong when coupled with the nasal cannula. As shown in FIG. 9B and 9D, a double channel conduit is provided. Each channel of the double channel conduit may have a round, oval or other similar profile and may couple with a tube shaped lumen. Each channel double conduit shown in FIG. 9b is rectangular and may be divided by a rib divider structure 10032 centrally located within the coupler extension. Each channel may lead to both prongs or each channel may lead to a different prong when coupled with the nasal cannula. Additional channel conduits may also be provided for example, by providing additional rib dividers.

As shown in FIG. 10A and 10B, when a mask is placed over the nasal cannula, such that the nasal cannula will be contained within the plenum chamber, the mask rests not only on the patient's facial contact areas but also on the seat portion of the nasal cannula. As further illustrated in FIG. 10B, the profile of the seat portion permits a seal between the seal forming structure of the mask so as to reduce gaps. Thus, the seat portion will typically have a length L and width W (see, e.g., FIG. 8 or FIG. 14A) adapted to receive typical mask cushions. The length may be longer than a typical cushion width. The length may be chosen to ensure seal during lateral displacement of the mask. A measurement from 0.5 to 3.0 inches may be a suitable length range. For example, an approximately two inch length may be suitable. The width may vary depending on the height of the channel conduits and typical flexibility characteristics of mask cushion materials so as to ensure a gradual sealing bevel that will avoid gaps.

The coupler extension may be formed by moulding, such as with a flexible material. For example, it may be formed of silicone. Optionally, the outer or end portions may be more rigid than the central section such as by having a solid cross section. The greater rigidity at the ends of the cross section may help with limiting their deformation so as to maintain their shape and avoid creation of gaps between the mask cushion and facial contact areas during use. In some versions of the coupler extension additional materials may be applied such as for improving compliance. For example, a skin contact surface may include a foam layer or soft material for improved comfort.

Although the version of the modified nasal cannula of FIG. 10A includes a single supply line on each side of the cannula (e.g., left side and right side supply lines), additional supply lines may be implemented. For example, as illustrated in FIGS. 11 and 12, two lumens are applied or protrude from each coupler extension. In some such cases, each lumen may be coupled with a different channel conduit of the coupler extension. In such arrangements, the lumens may be split above and/or below an ear to provide a more secure fitment for the patient.

Optionally, the seat portion of any of the cannula described herein may include a mask fitment structure, such as a seat ridge. The ridge can serve as a locating feature to indicate, or control, a relative position of the mask with respect to the seat portion. Such a seat ridge 12040 feature is illustrated in FIGS. 11 and 12. The seat ridge may rise from the surface of the seat portion such as on an outer area or edge of the seat portion (in a direction normal to the sagital plane).

FIG. 13 illustrates another version of the coupler extension of the present technology. In this version, the width of the seat portion includes an expansion area EA that expands the seat portion centrally along its length. Such a variation in the contact surface of the seat portion may assist in improving the seal between the seat portion and a mask cushion and/or the comfort of the seal between the coupler extension and the patient's facial contact area.

In some versions of the present technology a coupler extension 15020 may be formed as an add-on component for a traditional nasal cannula. Such an add-on coupler extension may be considered with reference to FIGS. 14A-14C. The add-on coupler extension 15020 may include one or more groove(s) 15052 for insertion of a supply line such as a lumen of a cannula. Thus, the coupler extension with its seat portion and sealing bevel may be easily applied to or under a lumen of a nasal cannula to reduce gaps when a mask is applied over the lumen of the traditional cannula.

The coupler extension 15020 may also include any of the features of the coupler extensions previously described. For example, as shown in FIGS. 14A, 14B, and 14C it may have various cross sectional profiles such as triangular profile and lentil profiles. In the version of FIG. 14C, two grooves 15052 are provided for insertion of two lumens, such as in the case that the traditional cannula includes two lumens extending out from one or both sides of the cannula. Although the figures have illustrated nasal cannula with two prongs, it will be understood that a nasal cannula of the present technology may be implemented with one or more nasal prongs (e.g., two).

7.7.2 Modified Nasal Pillow Embodiments

In some versions of the present technology, a common patient interface may provide a unitary structure for permitting application of various therapies. Thus, unlike the prior embodiments, the use and periodic application of an additional patient interface for varying therapy may not be necessary. Moreover, features of such a patient interface may be designed to minimize dead space.

One such patient interface example that can be implemented for periodic application of various therapies, for example an oxygen therapy and a PAP therapy, may be considered with reference to FIGS. 15A and 15B. The patient interface 16002 may serve as a nasal interface. Thus, it may include a set of naris pillows (e.g., one or more naris pillow(s) 16010). Each naris pillow may be flexible and may be configured to form a seal with the naris of a patient when worn. The naris pillow may have an outer conical surface 16012 that may engage at a skin periphery of a patient's naris either internal and/or externally of the nostril. Optionally, the naris pillow may also have an inner conical portion 16014 in a nested relationship with the outer conical portion (best seen in FIG. 17B). A gap may exist between the inner conical portion 16014 and the outer conical surface 16012. Each naris pillow may couple by a neck 16015 portion to a common base portion 16016. A passage through the central area of the outer conical portion (and/or inner conical portion), neck and base portion may serve as a flow path to and/or from a flow generator of CT device 4000 via an air circuit 4170. The air circuit 4170 may be coupled to the base portion 16016 of the patient interface at a flange 16018 (best seen in FIG. 17B). Optional base extensions 16020-1, 16020-2 may include connectors 16022-1, 16022-2 for connection of the patient interface with a stabilizing and positioning structure (e.g., straps or other headgear.)

One or both of the naris pillows may also include one or more nasal projections. Each nasal projection 16100 may be a conduit to conduct a flow of gas through the nasal projection. The nasal projection will typically project from the nasal pillow. As illustrated in FIG. 15A and 15B, the nasal projection may be configured to extend beyond the seal of the naris pillow (e.g., beyond the edge of the outer conical portion) so that it may project into or extend into the nasal cavity of a patient when used further than the naris pillow at a proximal end PE. The nasal projection 16100 may emanate from within the flow passage of the naris pillow (e.g., extend out of a conical portion). The nasal projection may optionally adhere to an inside wall of the naris pillow or other internal passage of the patient interface. In some cases, the nasal projection may be integrated with or formed with an inside wall of the naris pillow or other internal passage of the patient interface. Nevertheless, flow passage of the nasal projection will be discrete from the flow passage of the naris pillow. Typically, the length of the extension into a nasal cavity by the nasal projection may be in a range of about 5 mm to 15 mm.

Optionally, as shown in the version of FIGS. 15A and 15B, each nasal projection may extend through a passage of the naris pillow and a passage of the base portion. At a distal end DE of the nasal projection, the nasal projection may be removeably coupled to (or integrated with) a further conduit to a gas supply, such as a flow generator or supplemental gas source (e.g., an oxygen source). Alternatively, at a distal end DE of the nasal projection, the nasal projection may be open to atmosphere, such as to serve as a vent. In some cases, the distal end DE of the nasal projection may have a removable cap so as to close the distal end and thereby prevent flow through the nasal projection. For example, as illustrated in FIG. 16, a projection conduit 17170-1, 17170-2 may optionally be coupled to each of the nasal projections. Optionally, the projection conduits 17170 extend along and are external of the air circuit 4170. However, these projection conduits may extend along and are internal of the air circuit 4170 such as when they extend from the base portion 16016 and through the flange 16018 as illustrated in FIG. 17B.

In some versions of the patient interface 16002, one or more vents may be formed at or from a surface of the patient interface. In other versions, another component (e.g. an adapter or an air circuit 4170) including one or more vents may be fluidly coupled to the patient interface. The vent may serve as a flow passage to vent expired air from the apparatus. Optionally, such a base vent 16220 may be formed on the base portion 16016 as illustrated in FIG. 15A so as to vent from the chamber inside the base portion. In some cases, one or more vents may be formed on the naris pillow, such as on the neck 16015. In some cases, one or more vents may be formed on a part of the outer conical surface 16012 such as to vent from the chamber within the naris pillow portion of the patient interface. In some cases, such a vent may be a fixed opening with a known impedance. In some such cases, the vent may provide a known leak. Optionally, such a vent may be adjustable, such as by a manual manipulation, so as to increase or decrease an opening size of the vent. For example, the vent may be adjusted from fully open, partially open and closed positions, etc. In some cases, the vent may be an electro-mechanical vent that may be controlled by the flow generator so as increase or decrease the size of the vent between various opening and closed positions. Example vents and control thereof may be considered in reference to International Patent Application No. PCT/US2012/055148 filed on Sep. 13, 2012 and PCT Patent Application No. PCT/AU2014/000263 filed on Mar. 14, 2014, the entire disclosures of which are incorporated herein by reference.

By way of example, in the patient interface 16002 of FIGS. 17A and 17B, the nasal interface includes multiple nasal projections 16100 extending from each naris pillow. At least one such nasal projection may serve as a pillow vent 18220 for example, at a bottom portion of the outer conical surface of the naris pillow. In the example, the nasal projections 16100-1 each form a conduit that lead to atmosphere through the naris pillow from the nasal cavity of a patient. With such a nasal projection extending into the nasal cavity, a patient's deadspace can be reduced through a shortened pathway for expired air (carbon dioxide) to be removed from the patient's airways. In some such examples, the additional nasal projections 16100-2 may be coupled with a supplemental gas source such as an oxygen source or a controlled flow of air as discussed in more detail herein. Optionally, such nasal projections of each naris pillow may be formed with a deviating projection (shown in FIG. 17A at arrows DB). Such a deviation such that they are further apart at the proximal end when compared to lower portions can assist with holding the extensions within the nasal cavity during use. Thus, they may gently ply within a nasal cavity on opposing sides of the nasal cavity.

7.8 Glossary

For the purposes of the present technology disclosure, in certain forms of the present technology, one or more of the following definitions may apply. In other forms of the present technology, alternative definitions may apply.

7.8.1 General

Air: In certain forms of the present technology, air may refer to atmospheric air as well as other breathable gases. For instance, air supplied to a patient may be atmospheric air or oxygen, and in other forms of the present technology, air may comprise atmospheric air supplemented with oxygen.

Ambient: In certain forms of the present technology, the term ambient will be taken to mean (i) external of the treatment system or patient, and (ii) immediately surrounding the treatment system or patient.

7.8.2 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

7.8.3 Aspects of PAP Devices

APAP: Automatic Positive Airway Pressure. Positive airway pressure that is continually adjustable between minimum and maximum limits, depending on the presence or absence of indications of SDB events.

Controller: A device, or portion of a device that adjusts an output based on an input. For example one form of controller has a variable that is under control—the control variable—that constitutes the input to the device. The output of the device is a function of the current value of the control variable, and a set point for the variable. A servo-ventilator may include a controller to provide a ventilation therapy. Such a ventilation therapy has ventilation as an input, a target ventilation as the set point, and level of pressure support as an output. Other forms of input may be one or more of oxygen saturation ($SaO_2$), partial pressure of carbon dioxide ($PCO_2$), movement, a signal from a photoplethysmogram, and peak flow. The set point of the controller may be one or more of fixed, variable or learned. For example, the set point in a ventilator may be a long term average of the measured ventilation of a patient. Another ventilator may have a ventilation set point that changes with time. A pressure controller may be configured to control a blower or pump to deliver air at a particular pressure. A flow controller may be configured to control a blower or other gas source to deliver air at a particular flow rate.

Therapy: Therapy in the present context may be one or more of positive pressure therapy, oxygen therapy, carbon dioxide therapy, deadspace therapy, and the administration of a drug.

7.8.4 Terms for Ventilators

Adaptive Servo-Ventilator: A ventilator that has a changeable, rather than fixed target ventilation. The changeable target ventilation may be learned from some characteristic of the patient, for example, a respiratory characteristic of the patient.

Backup rate: A parameter of a ventilator that establishes the minimum respiration rate (typically in number of breaths per minute) that the ventilator will deliver to the patient, if not otherwise triggered.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Pressure support: A number for a ventilation therapy that is indicative of the increase in pressure during ventilator inspiration over that during ventilator expiration, and generally means the difference in pressure between the maximum value during inspiration and the minimum value during expiration (e.g., PS=IPAP-EPAP). In some contexts pressure support means the difference which the ventilator aims to achieve, rather than what it actually achieves.

Servo-ventilator: A ventilator that provides a ventilation therapy for which the device measures patient ventilation, has a target ventilation, and which adjusts the level of pressure support to bring the patient ventilation towards the target ventilation.

Spontaneous/Timed (S/T)—A mode of a ventilator or other device that attempts to detect the initiation of a breath of a spontaneously breathing patient. If however, the device is unable to detect a breath within a predetermined period of time, the device will automatically initiate delivery of the breath.

Triggered: When a ventilator delivers a breath of air to a spontaneously breathing patient, it is said to be triggered to do so at the initiation of the respiratory portion of the breathing cycle by the patient's efforts.

Ventilation: A volumetric measure of gas being exchanged by the patient's respiratory system, such as a tidal volume. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

A ventilation therapy can provide a volume of gas for patient respiration so as to perform some of the work of breathing.

Ventilator: A mechanical device that provides pressure support to a patient to perform some or all of the work of breathing.

7.9 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein may have been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. A method for controlling a supply of air to a patient's airways for a respiratory therapy, the method comprising:
   identifying, by one or more controllers, a predetermined pressure and a predetermined flow rate of the air to be provided to a patient via a patient interface, wherein the patient interface comprises a mask portion that includes a vent;
   limiting, by the one or more controllers, the predetermined flow rate to be less than a maximum flow rate, wherein the maximum flow rate is a vent flow rate minus a peak expiratory flow rate of the patient;
   determining, with a plurality of sensors, a pressure and a flow rate of the air being provided to the patient via the patient interface; and
   controlling, by the one or more controllers, a first flow generator and a second flow generator, each flow generator being configured to provide a flow of the air to the patient interface, so as to simultaneously control the pressure and the flow rate of the air at the patient interface to correspond with the predetermined pressure and the predetermined flow rate, respectively.

2. The method of claim 1, wherein controlling the first flow generator and the second flow generator comprises adjusting output of at least one of the first flow generator and the second flow generator.

3. The method of claim 1, wherein the patient interface comprises a projection portion configured to conduct a flow of the air into a naris of the patient, and wherein the mask portion is configured to apply pressure of the air to the patient.

4. The method of claim 3, wherein the mask portion is a nasal mask.

5. The method of claim 3, wherein the mask portion comprises one or more nasal pillows.

6. The method of claim 4, further comprising:
   detecting a continuous mouth leak, and
   reducing the predetermined pressure upon detecting the continuous mouth leak.

7. The method of claim 3, wherein the first flow generator provides the flow of the air through the projection portion of the patient interface and the second flow generator applies pressure of the air to the mask portion of the patient interface.

8. The method of claim 1, wherein at least one of the predetermined pressure and the predetermined flow rate varies over a period of time corresponding to a breathing cycle of the patient.

9. The method of claim 1, wherein the predetermined flow rate is constant for at least some predetermined period of time and the predetermined pressure is constant during the predetermined period of time.

10. The method of claim 1, wherein simultaneously controlling the pressure and the flow rate further comprises controlling an adjustment of the vent.

11. The method of claim 10, wherein the vent comprises an active proximal valve.

12. The method of claim 1, wherein simultaneously controlling the pressure and the flow rate is performed so as to provide the patient with a positive airway pressure therapy and a deadspace therapy.

13. The method of claim 12, wherein the positive airway pressure therapy is a ventilation therapy.

14. The method of claim 1 further comprising calculating, in a controller of the one or more controllers, a target ventilation based on anatomical deadspace information and a deadspace therapy reduction value.

15. The method of claim 1 further comprising generating, in a controller of the one or more controllers, a cardiac output estimate by controlling a step change in the predetermined flow rate of the air and determining a change in a measure of ventilation in relation to the step change.

16. The method of claim 15 further comprising initiating, by the controller of the one or more controllers, the controlling of the step change in the predetermined flow rate of the air in response to a detection of sleep.

17. The A method for controlling a supply of air to a patient's airways for a respiratory therapy, the method comprising:
   determining, by one or more controllers, the a predetermined pressure and a predetermined flow rate of the air to be provided to a patient via a patient interface so as to restrict the predetermined pressure and the predetermined flow rate to a curve of equal efficacy;
   determining, with a plurality of sensors, a pressure and a flow rate of the air being provided to the patient via the patient interface; and
   controlling, by the one or more controllers, a first flow generator and a second flow generator, each flow generator being configured to provide a flow of the air to the patient interface, so as to simultaneously control the pressure and the flow rate of the air at the patient interface to correspond with the predetermined pressure and the predetermined flow rate, respectively.

18. A system for delivery of a flow of air to a patient's airways comprising:
   a first flow generator and a second flow generator, each configured to provide air to a patient via a patient interface, wherein the patient interface comprises a mask portion that includes a vent; and
   one or more controllers configured to:
      determine a pressure and a flow rate of the air being provided to the patient via the patient interface with a plurality of sensors; and control the first flow generator and the second flow generator so as to simultaneously control the pressure and the flow rate of the air at the patient interface to correspond with a predetermined pressure and a predetermined flow rate, respectively,
wherein the one or more controllers are further configured to limit the predetermined flow rate to be less than a maximum flow rate, and wherein the one or more controllers are configured to determine the maximum flow rate by subtracting a peak expiratory flow rate of the patient from a vent flow rate.

19. The system of claim 18, further comprising the patient interface, wherein the patient interface comprises a projection portion configured to conduct a flow of the air into a naris of the patient, and wherein the mask portion is configured to apply pressure of the air to the patient.

20. The system of claim 19, wherein the mask portion is a nasal mask.

21. The system of claim 19, wherein the mask portion comprises one or more nasal pillows.

22. The system of claim 19, wherein the first flow generator conducts the flow of the air through the projection portion and the second flow generator applies pressure of the air to the mask portion.

23. The system of claim 18, wherein the plurality of sensors comprise a flow rate sensor and a pressure sensor, wherein an output of the first flow generator is measured by the flow rate sensor and an output of the second flow generator is measured by the pressure sensor.

24. The system of claim 18, wherein the one or more controllers are further configured to maintain at least one of the predetermined pressure and the predetermined flow rate at a constant value for at least some period of time.

25. The system of claim 18, wherein the controllers are further configured to vary at least one of the predetermined pressure and the predetermined flow rate over a period of time corresponding to a breathing cycle of the patient.

26. The system of claim 18, wherein the vent is an adjustable vent and wherein the one or more controllers are further configured to control the adjustable vent so as to control the pressure and the flow rate.

27. The system of claim 26, wherein the adjustable vent comprises an active proximal valve.

28. The system of claim 18, wherein the simultaneous control of the pressure and the flow rate of the air provides the patient with a positive airway pressure therapy and a deadspace therapy.

29. The system of claim 28, wherein the positive airway pressure therapy is a ventilation therapy.

30. The system of claim 18, wherein the one or more controllers comprise one controller configured to control the first flow generator and the second flow generator.

31. The system of claim 18, wherein the one or more controllers comprise a first controller configured to control the first flow generator and a second controller configured to control the second flow generator.

32. The system of claim 31, wherein the first controller is configured to obtain the flow rate of the air being provided by the second flow generator.

33. The system of claim 31, wherein the second controller is configured to obtain the pressure of the air being provided by the first flow generator.

34. The system of claim 18 wherein a controller of the one or more controllers is configured to compute a target ventilation based on anatomical deadspace information and a deadspace therapy reduction value.

35. The system of claim 18 wherein a controller of the one or more controllers is configured to generate a cardiac output estimate by controlling a step change in the predetermined flow rate of the air and determining a change in a measure of ventilation in relation to the step change.

36. The system of claim 35 wherein the controller of the one or more controllers is configured to initiate control of the step change in the predetermined flow rate of the air in response to a detection of sleep.

37. A system for delivery of a flow of air to a patient's airways comprising:
a first flow generator and a second flow generator, each configured to provide air to a patient via a patient interface; and
one or more controllers configured to:
determine a predetermined pressure and a predetermined flow rate so as to restrict the predetermined pressure and the predetermined flow rate to a curve of equal efficacy;
determine a pressure and a flow rate of the air being provided to the patient via the patient interface with a plurality of sensors; and
control the first flow generator and the second flow generator so as to simultaneously control the pressure and the flow rate of the air at the patient interface to correspond with the predetermined pressure and the predetermined flow rate, respectively.

* * * * *